(12) United States Patent
Cutshall et al.

(10) Patent No.: US 9,783,521 B2
(45) Date of Patent: Oct. 10, 2017

(54) PDE10 INHIBITORS AND RELATED COMPOSITIONS AND METHODS

(71) Applicant: Omeros Corporation, Seattle, WA (US)

(72) Inventors: Neil S. Cutshall, Snohomish, WA (US); Jennifer Lynn Gage, Kenmore, WA (US); Thomas Neil Wheeler, Raleigh, NC (US)

(73) Assignee: Omeros Corporation, Seattle, WA (US)

(*) Notice: Subject to any disclaimer, the term of this patent is extended or adjusted under 35 U.S.C. 154(b) by 220 days.

(21) Appl. No.: 13/742,199

(22) Filed: Jan. 15, 2013

(65) Prior Publication Data

US 2014/0038951 A1 Feb. 6, 2014

Related U.S. Application Data

(62) Division of application No. 12/535,598, filed on Aug. 4, 2009, now Pat. No. 8,377,930.

(Continued)

(51) Int. Cl.

| | | |
|---|---|---|
| *A61K 31/15* | (2006.01) | |
| *A61P 25/18* | (2006.01) | |
| *A61P 25/16* | (2006.01) | |
| *A61P 25/28* | (2006.01) | |
| *A61P 25/14* | (2006.01) | |
| *C07D 401/04* | (2006.01) | |
| *A61K 31/357* | (2006.01) | |
| *A61K 31/36* | (2006.01) | |
| *A61K 31/40* | (2006.01) | |
| *A61K 31/41* | (2006.01) | |
| *A61K 31/415* | (2006.01) | |
| *A61K 31/4184* | (2006.01) | |
| *A61K 31/4196* | (2006.01) | |
| *A61K 31/425* | (2006.01) | |
| *A61K 31/47* | (2006.01) | |
| *A61K 31/5375* | (2006.01) | |
| *A61K 31/54* | (2006.01) | |
| *C07C 251/86* | (2006.01) | |
| *C07C 251/88* | (2006.01) | |
| *C07C 255/66* | (2006.01) | |
| *C07D 213/56* | (2006.01) | |
| *C07D 213/74* | (2006.01) | |
| *C07D 215/14* | (2006.01) | |
| *C07D 231/12* | (2006.01) | |
| *C07D 235/16* | (2006.01) | |
| *C07D 249/04* | (2006.01) | |

(Continued)

(52) U.S. Cl.
CPC .......... *C07D 401/04* (2013.01); *A61K 31/15* (2013.01); *A61K 31/357* (2013.01); *A61K 31/36* (2013.01); *A61K 31/40* (2013.01); *A61K 31/41* (2013.01); *A61K 31/415* (2013.01); *A61K 31/4184* (2013.01); *A61K 31/4196* (2013.01); *A61K 31/425* (2013.01); *A61K 31/47* (2013.01); *A61K 31/5375* (2013.01); *A61K 31/54* (2013.01); *C07C 243/32* (2013.01); *C07C 251/80* (2013.01); *C07C 251/86* (2013.01); *C07C 251/88* (2013.01); *C07C 255/66* (2013.01); *C07D 213/56* (2013.01); *C07D 213/74* (2013.01); *C07D 215/14* (2013.01); *C07D 231/12* (2013.01); *C07D 235/16* (2013.01); *C07D 249/04* (2013.01); *C07D 249/08* (2013.01); *C07D 257/06* (2013.01); *C07D 265/36* (2013.01); *C07D 275/02* (2013.01); *C07D 295/135* (2013.01); *C07D 295/155* (2013.01); *C07D 317/62* (2013.01); *C07D 319/18* (2013.01); *C07D 333/60* (2013.01); *C07C 2601/08* (2017.05)

(58) Field of Classification Search
CPC ...................................................... A61K 31/15
See application file for complete search history.

(56) References Cited

U.S. PATENT DOCUMENTS

| | | |
|---|---|---|
| 5,693,652 A | 12/1997 | Takase et al. |
| 7,786,139 B2 | 8/2010 | Bergmann et al. |

(Continued)

FOREIGN PATENT DOCUMENTS

| | | |
|---|---|---|
| AU | 16134/88 A | 11/1988 |
| JP | 64-063561 A | 3/1989 |

(Continued)

OTHER PUBLICATIONS

Asthana et al., "α-Phenoxy-& Thiophenoxyphenylacetic Acid Derivatives as Hypoglycaemic Agents," *Indian Journal of Chemistry* 8:1086-1095, Dec. 1970.

(Continued)

*Primary Examiner* — Sahar Javanmard
(74) *Attorney, Agent, or Firm* — Seed IP Law Group LLP

(57) ABSTRACT

Compounds that inhibit PDE10 are disclosed that have utility in the treatment of a variety of conditions, including (but not limited to) psychotic, anxiety, movement disorders and/or neurological disorders such as Parkinson's disease, Huntington's disease, Alzheimer's disease, encephalitis, phobias, epilepsy, aphasia, Bell's palsy, cerebral palsy, sleep disorders, pain, Tourette's syndrome, schizophrenia, delusional disorders, drug-induced psychosis and panic and obsessive-compulsive disorders. Pharmaceutically acceptable salts, stereoisomers, solvates and prodrugs of the compounds are also provided. Also disclosed are compositions containing a compound in combination with a pharmaceutically acceptable carrier, as well as methods relating to the use thereof for inhibiting PDE10 in a warm-blooded animal in need of the same.

33 Claims, 10 Drawing Sheets

Related U.S. Application Data

(60) Provisional application No. 61/218,311, filed on Jun. 18, 2009, provisional application No. 61/118,088, filed on Nov. 26, 2008, provisional application No. 61/086,406, filed on Aug. 5, 2008.

(51) Int. Cl.

| | | |
|---|---|---|
| C07D 249/08 | (2006.01) | |
| C07D 257/06 | (2006.01) | |
| C07D 265/36 | (2006.01) | |
| C07D 275/02 | (2006.01) | |
| C07D 295/155 | (2006.01) | |
| C07D 317/62 | (2006.01) | |
| C07D 319/18 | (2006.01) | |
| C07D 333/60 | (2006.01) | |
| C07C 243/32 | (2006.01) | |
| C07C 251/80 | (2006.01) | |
| C07D 295/135 | (2006.01) | |

(56) References Cited

U.S. PATENT DOCUMENTS

| | | |
|---|---|---|
| 8,278,327 B2 | 10/2012 | Begmann et al. |
| 8,343,970 B2 | 1/2013 | Cutshall et al. |
| 8,377,930 B2 | 2/2013 | Cutshall et al. |
| 2003/0032579 A1 | 2/2003 | Lebel et al. |
| 2004/0254182 A1 | 12/2004 | Mulvihill et al. |
| 2007/0060646 A1 | 3/2007 | Gericke et al. |
| 2008/0300240 A1 | 12/2008 | Bergmann et al. |
| 2009/0163545 A1 | 6/2009 | Goldfarb |

FOREIGN PATENT DOCUMENTS

| | | |
|---|---|---|
| WO | WO 01/41807 A2 | 6/2001 |
| WO | WO 01/54481 A2 | 8/2001 |
| WO | WO 2004/033413 A2 | 4/2004 |
| WO | WO 2005/070419 A1 | 8/2005 |
| WO | WO 2005/084651 A2 | 9/2005 |
| WO | WO 2005/094796 A2 | 10/2005 |
| WO | WO 2005/094829 A1 | 10/2005 |
| WO | WO 2006/121684 A2 | 11/2006 |
| WO | WO 2008/064342 A2 | 5/2008 |
| WO | WO 2009/086303 A2 | 7/2009 |
| WO | WO 2009/143178 A2 | 11/2009 |
| WO | WO 2010/017236 A1 | 2/2010 |
| WO | WO 2011/112828 A1 | 9/2011 |

OTHER PUBLICATIONS

Carpino et al., "Thermolysis of 7-(Acylamino)-7-azabenzonorbornadienes and 1-(Acylamino)aziridines. Generation and Trapping of Monosubstituted Azamines," *J. Org. Chem.* 53(26):6047-6053, 1988.

Fujishige et al., "Cloning and Characterization of a Novel Human Phosphodiesterase That Hydrolyzes Both cAMP and cGMP (PDE10A)," *The Journal of Biological Chemistry*, 274(26):18438-18445, Jun. 25, 1999.

Geita et al., "The Mechamism of the Beckmann Rearrangement. Transformations of 2-Acyl-1,3-Indanedione Oximes," Institute of Organic Synthesis Academy of Sciences of the Latvian SSR:1346-1350. Translated from *Zhurnal Organicheskoi Khimii* 13 (7), 1461-1465, Jul. 1977.

Gilchrist et al., "Formation of Pyridazino[6, 1-c] [1,4]oxazin-8(7H)—ones by Intramolecular Cycloaddition of Azoalkenes," *J. Chem. Soc. Perkin Trans. I*:2517-2522, 1987.

Hüller et al., "Zur Pharmakologie einer Serie neuer Benzilsäurederivate," *Acta biol. med. germ.* 10:357-374, 1963 (+ English abstract).

Ivanova et al., "Derivatives of Acid Chlorides of N-Acylimidocarbonic Acids," Institute of Organic Chemistry, Academy of Science of the Ukrainian SSR:2228-2232. Translated from *Zhurnal Organicheskioi Khimii* 1(12):2186-2191, Dec. 1965.

Klosa, J., "Synthese neuer basischer Amide von α-Alkoxydiphenylessigsäuren," *Journal für praktische Chemie* 31:14-19, 1966 (+ English abstract).

Klosa, J., "Synthese von α-Alkoxy-benzilsäurehydraziden" *Journal für praktische Chemie* 31:20-33, 1966 (+ English abstract).

Loughney et al., "Isolation and characterization of PDE10A, a novel human 3', 5'-cyclic nucleotide phosphodiesterase," *Gene* 234:109-117, 1999.

Lugnier, C., "Cyclic nucleotide phosphodiesterase (PDE) superfamily: A new target for the development of specific therapeutic agents," *Pharmacology & Therapeutics* 109:366-398, 2006.

Maroulis et al., "The Thermal Isomerization of 1-(α-Aroyloxybenzylideneamino)-4,5-di-methyl-1,2,3-triazoles (Isoimides) to the Corresponding Imides," *J. Heterocyclic Chem.* 21:1653-1656, Nov.-Dec. 1984.

Monge et al., "The Reaction of 2-Indolecarbohydrazones With Ethoxycarbonyl Chloride. New Synthesis of 2,3-Dihydro-2-oxo-1,3,4-oxadiazoles and 1,2,3,4-Tetrahydro-4-oxo-5H-pyridazino[4,5-b]indoles," *J. Heterocyclic Chem.* 21:397-400, Mar.-Apr. 1984.

Nicolaescu et al., "Contribution À L'Étude De La Réaction Des Acides Phénylglycoliques Avec Les Thiophénols VI. Les Spectres D'Absorption En Infrarouge De Quelques Esters Et Hydrazides Des Acides α-Phénylsulfonyl-Phénylacétiques," Analele Ştiinţifice Ale Universităţii ,, Al. I. Cuza Din Iaşi (Serie Nouă) Secţiunea , c: Chimie 17(1):49-52, 1971 (+ English abstract).

Pandeya et al., "Design of semicarbazones and their bio-isosteric analogues as potential anticonvulsants," *Pharmazie* 56(2):121-124, 2001.

Singh et al., "Reaction of Open-Chain Conjugated Nitrones With Lead Tetraacetate and Acetic Anhydride," *Tetrahedron Letters* 29:2711-2714, 1973.

Soderling et al., "Isolation and characterization of a dual-substrate phosphodiesterase gene family: PDE10A," *Proc. Natl. Acad. Sci. USA* 96:7071-7076, Jun. 1999.

Soderling et al., "Regulation of cAMP and cGMP signaling: new phosphodiesterases and new functions," *Current Opinion in Cell Biology* 12:174-179, 2000.

Stephanidou-Stephanatou et al., "Oxidation of Arylacetylhydrazones of Carbonyl Compounds with Lead Tetraacetate," *J. Heterocyclic Chem.* 19:705-711, Jul.-Aug. 1982.

Thompson et al., "Multiple Cyclic Nucleotide Phosphodiesterase Activities from Rat Brain," *Biochemistry* 10(2):311-316, 1971.

Yurzhenko et al., "Tetraphenyldiglycolic acid and its heterocyclic derivatives," *Dopovidi Akademii Nauk Ukrains'koi RSR, Seriya B: Geologiya, Geofizika, Khimiya to Biologiya*: 30(8):743-746, 1968 (+ English abstract).

Office Action for U.S. Appl. No. 12/535,598, dated Dec. 8, 2011 (10 pages).

Office Action for U.S. Appl. No. 12/535,598, dated Mar. 7, 2012 (17 pages).

Notice of Allowance and Fee(s) Due for U.S. Appl. No. 12/535,598, dated Oct. 15, 2012 (9 pages).

International Search Report and Written Opinion for PCT International Application No. PCT/US2009/052754, mailed Oct. 15, 2009 (9 pages).

International Preliminary Report on Patentability for PCT International Application No. PCT/US2009/052754, dated Feb. 8, 2011 (7 pages).

Supplementary European Search Report for EP Application No. 09805466, mailed Aug. 24, 2011 (7 pages).

Fujishige et al., "Striatum- and testis-specific phosphodiesterase PDE10A—Isolation and characterization of a rat PDE10A,"*Eur. J. Biochem* 266:1118-1127, 1999.

Kotera et al., "Characterization and Phosphorylation of PDE10A2, a Novel Alternative Splice Variant of Human Phosphodiesterase That Hydrolyzes cAMP and cGMP," *Biochemical and Biophysical Research Communications* 261:551-557, 1999.

Kehler et al., "The potential therapeutic use of phosphodiesterase 10 inhibitors," *Expert Opinion Ther. Patents* 17(2):147-158, 2007.

PDE10 INHIBITORS AND RELATED COMPOSITIONS AND METHODS

CROSS-REFERENCE TO RELATED APPLICATIONS

This application is a divisional of U.S. patent application Ser. No. 12/535,598, filed Aug. 4, 2009, now pending, which claims the benefit under 35 U.S.C. §119(e) of U.S. Provisional Patent Application No. 61/086,406, filed Aug. 5, 2008, U.S. Provisional Patent Application No. 61/118,088, filed Nov. 26, 2008, and U.S. Provisional Patent Application No. 61/218,311, filed Jun. 18, 2009, which applications are incorporated herein by reference in their entireties.

BACKGROUND

Technical Field

This invention relates generally to compounds having activity as PDE10 inhibitors, and to compositions containing the same, as well as to methods of treating various disorders by administration of such compounds to a warm-blooded animal in need thereof.

Description of the Related Art

Cyclic nucleotide phosphodiesterases (PDEs) are represented by a large superfamily of enzymes. PDEs are known to possess a modular architecture, with a conserved catalytic domain proximal to the carboxyl terminus, and regulatory domains or motifs often near the amino terminus. The PDE superfamily currently includes more than twenty different genes subgrouped into eleven PDE families (Lugnier, C., "Cyclic nucleotide phosphodiesterase (PDE) superfamily: a new target for the development of specific therapeutic agents." Pharmacol Ther. 2006 March; 109(3):366-98).

A recently described PDE, PDE10, was reported simultaneously by three independent groups (Fujishige et al., "Cloning and characterization of a novel human phosphodiesterase that hydrolyzes both cAMP and cGMP (PDE10A)," *J Biol Chem* 1999, 274:18438-18445; Loughney et al., "Isolation and characterization of PDE10A, a novel human 3′,5′-cyclic nucleotide phosphodiesterase," *Gene* 1999, 234:109-117; Soderling et al., "Isolation and characterization of a dual-substrate phosphodiesterase gene family: PDE10A," *Proc Natl Acad Sci USA* 1999, 96:7071-7076). PDE10 has the capacity to hydrolyze both cAMP and cGMP; however, the $K_m$ for cAMP is approximately 0.05 μM, whereas the $K_M$ for cGMP is 3 μM. In addition, the $V_{max}$ for cAMP hydrolysis is fivefold lower than for cGMP. Because of these kinetics, cGMP hydrolysis by PDE10 is potently inhibited by cAMP in vitro, suggesting that PDE10 may function as a cAMP-inhibited cGMP phosphodiesterase in vivo. Unlike PDE8 or PDE9, PDE10 is inhibited by IBMX with an $IC_{50}$ (50% inhibitory concentration) of 2.6 μM. (See Soderling and Beavo, "Regulation of cAMP and cGMIP signaling: new phosphodiesterases and new functions," *Current Opinion in Cell Biology*, 2000, 12:174-179.)

PDE10 contains two amino-terminal domains that are similar to the cGMP-binding domains of PDE2, PDE5 and PDE6, which are domains conserved across a wide variety of proteins. Because of the wide conservation of this domain, it is now referred to as the GAF domain (for the GAF proteins: cGMP binding phosphodiesterases; the cynobacterial *Anabaena* adenylyl cyclase; and the *Escherichia coli* transcriptional regulator fhlA). Although in PDE2, PDE5 and PDE6 the GAF domains bind cGMP, this is probably not the primary function of this domain in all cases (e.g., *E. coli* are not thought to synthesize cGMP). Interestingly, in vitro binding studies of PDE10 indicate the dissociation constant ($K_d$) for cGMP binding is well above 9 μM. As in vivo concentrations of cGMP are not thought to reach such high levels in most cells, it seems likely that either the affinity of PDE10 for cGMP is increased by regulation, or that the primary function of the GAF domain in PDE10 may be for something other than cGMP binding.

Inhibitors of the PDE family of enzymes have widely been sought for a broad indication of therapeutic uses. Reported therapeutic uses of PDE inhibitors include allergies, obtrusive lung disease, hypertension, renal carcinoma, angina, congestive heart failure, depression and erectile dysfunction (WO 01/41807 A2). Other inhibitors of PDE have been disclosed for treatment of ischemic heart conditions (U.S. Pat. No. 5,693,652). More specifically, inhibitors of PDE10 have been disclosed for treatment of certain neurological and psychiatric disorders including, Parkinson's disease, Huntington's disease, schizophrenia, delusional disorders, drug-induced psychosis and panic and obsessive-compulsive disorders (U.S. Patent Application No. 2003/0032579). PDE10 has been shown to be present at high levels in neurons in areas of the brain that are closely associated with many neurological and psychiatric disorders. By inhibiting PDE10 activity, levels of cAMP and cGMP are increased within neurons, and the ability of these neurons to function properly is thereby improved. Thus, inhibition of PDE10 is believed to be useful in the treatment of a wide variety of conditions or disorders that would benefit from increasing levels of cAMP and cGMP within neurons, including those neurological, psychotic, anxiety and/or movement disorders mentioned above.

While advances have been made with regard to inhibition of PDE10, there remains a need in the field for inhibitors of PDE 10, as well as the need to treat various conditions and/or disorders that would benefit from the same.

BRIEF SUMMARY

In brief, this invention is generally directed to compounds that have activity as PDE10 inhibitors, as well as to methods for their preparation and use, and to pharmaceutical compositions containing the same.

In one embodiment, the compounds have the following general structure (I):

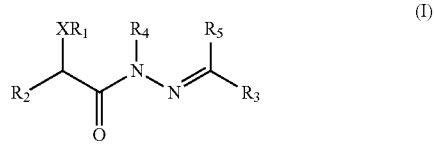

(I)

including pharmaceutically acceptable salts, stereoisomers, solvates and prodrugs thereof, wherein X, $R_1$, $R_2$, $R_3$, $R_4$ and $R_5$ are as defined below.

In another embodiment, the compounds have the following general structure (IV):

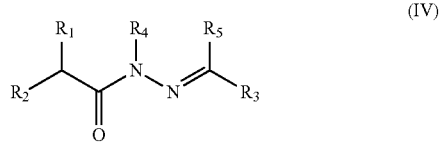

(IV)

including pharmaceutically acceptable salts, stereoisomers, solvates and prodrugs thereof, wherein $R_1$, $R_2$, $R_3$, $R_4$ and $R_5$ are as defined below.

The compounds of this invention have utility over a wide range of therapeutic applications, and may be used to treat a wide variety of conditions or disorders that would benefit from increasing levels of cAMP and cGMP, especially within neurons, including (but not limited to) neurological disorders, such as psychotic disorders, anxiety disorders, movement disorders and/or neurological disorders such as Parkinson's disease, Huntington's disease, Alzheimer's disease, encephalitis, phobias, epilepsy, aphasia, Bell's palsy, cerebral palsy, sleep disorders, pain, Tourette's syndrome, schizophrenia, delusional disorders, bipolar disorders, post-traumatic stress disorders, drug-induced psychosis, panic disorders, obsessive-compulsive disorders, attention-deficit disorders, disruptive behavior disorders, autism, depression, dementia, cognitive disorders, epilepsy, insomnias and multiple sclerosis.

The methods of this invention include administering an effective amount of a compound of the foregoing structures, typically in the form of a pharmaceutical composition, to a mammal in need thereof, including a human. Thus, in a further embodiment, pharmaceutical compositions are disclosed containing one or more compounds of the foregoing structures in combination with a pharmaceutically acceptable carrier or diluent.

These and other aspects of the invention will be apparent upon reference to the following detailed description. To this end, various references are set forth herein which describe in more detail certain background information, procedures, compounds and/or compositions, and are each hereby incorporated by reference in their entirety.

DETAILED DESCRIPTION

Figure 1:
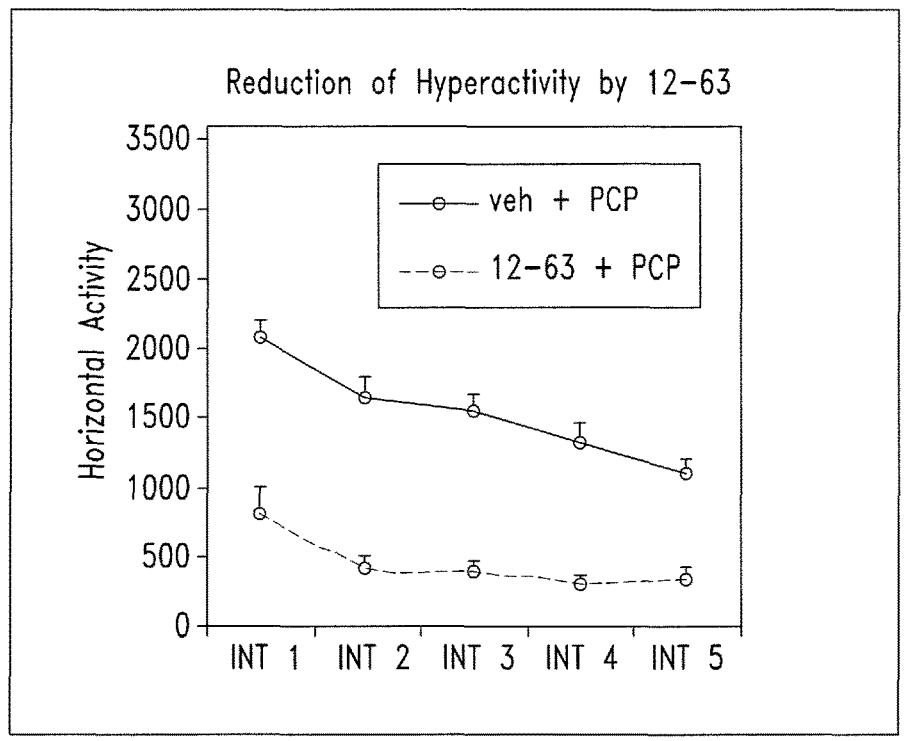
FIG. 1 illustrates that Compound 12-63 of the present invention (as identified in Table 1 of Example 12) significantly reduces hyperactivity of mice in a psychostimulant (PCP)-induced model of psychosis as compared to vehicle control.

As mentioned above, the present invention is directed generally to compounds useful as PDE10 inhibitors, as well as to methods for their preparation and use, and to pharmaceutical compositions containing the same.

In one embodiment, the PDE10 inhibitors have the following structure (I):

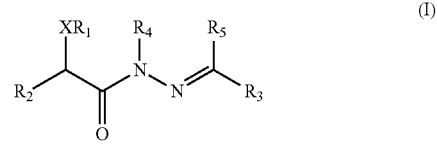

or a pharmaceutically acceptable salt, stereoisomer, solvate or prodrug thereof, wherein:

X is —O— or —S—;

$R_1$ is $C_{1-6}$alkyl, $C_{1-6}$haloalkyl, $C_{1-6}$aralkyl, aryl, —$(CH_2)_nO(CH_2)_mCH_3$ or —$(CH_2)_nN(CH_3)_2$;

$R_2$ and $R_3$ are the same or different and independently substituted or unsubstituted heterocyclyl, or substituted or unsubstituted aryl;

$R_4$ and $R_5$ are the same or different and independently hydrogen, $C_{1-6}$alkyl or $C_{1-6}$haloalkyl;

n is 1, 2, 3, 4, 5 or 6; and m is 0, 1, 2, 3, 4, 5 or 6.

In another embodiment, the PDE10 inhibitors have the following structure (IV):

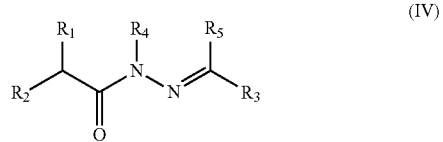

or a pharmaceutically acceptable salt, stereoisomer, solvate or prodrug thereof, wherein:

$R_1$ is hydrogen, $C_{1-6}$alkyl, $C_{1-6}$haloalkyl, $C_{1-6}$aralkyl, aryl, —$(CH_2)_nO(CH_2)_mCH_3$ or —$(CH_2)_nN(CH_3)_2$;

$R_2$ is substituted or unsubstituted aryl;

$R_3$ is substituted or unsubstituted heterocyclyl, or substituted or unsubstituted aryl; and $R_4$ and $R_5$ are the same or different and independently hydrogen, $C_{1-6}$alkyl or $C_{1-6}$haloalkyl;

n is 1, 2, 3, 4, 5 or 6; and m is 0, 1, 2, 3, 4, 5 or 6.

As used herein, the above terms have the following meaning:

"Amino" refers to the —$NH_2$ radical.

"Cyano" refers to the —CN radical.

"Hydroxy" or "hydroxyl" refers to the —OH radical.

"Imino" refers to the =NH substituent.

"Nitro" refers to the —$NO_2$ radical.

"Oxo" refers to the =O substituent.

"Thioxo" refers to the =S substituent.

"$C_{1-6}$alkyl" means a straight chain or branched, noncyclic or cyclic, unsaturated or saturated aliphatic hydrocarbon radical containing from 1 to 6 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, and the like; while unsaturated cyclic alkyls include cyclopentenyl and cyclohexenyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

"$C_{1-6}$alkylene" or "$C_{1-6}$alkylene chain" refers to a straight or branched divalent hydrocarbon chain linking the rest of the molecule to a radical group, consisting solely of carbon and hydrogen, which is saturated or unsaturated (i.e., contains one or more double and/or triple bonds), and having from one to six carbon atoms, e.g., methylene, ethylene, propylene, n-butylene, ethenylene, propenylene, n-butenylene, propynylene, n-butynylene, and the like. The alkylene chain is attached to the rest of the molecule through a single or double bond and to the radical group through a single or double bond. The points of attachment of the alkylene chain to the rest of the molecule and to the radical group can be through one carbon or any two carbons within the chain.

"$C_{1-6}$alkoxy" refers to a radical of the formula —$OR_a$ where $R_a$ is an alkyl radical as defined above, for example, methoxy, ethoxy and the like.

"Aryl" means a hydrocarbon ring system radical comprising hydrogen, 6 to 18 carbon atoms and at least one aromatic ring. The aryl radical may be a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene.

"$C_{1-6}$aralkyl" means a radical of the formula —$R_b$-$R_c$ where $R_b$ is an alkylene chain as defined above and $R_c$ is one or more aryl radicals as defined above, for example, benzyl, diphenylmethyl and the like.

"Cycloalkyl" or "carbocyclic ring" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1]heptanyl, and the like.

"Halo" or "halogen" refers to bromo, chloro, fluoro or iodo.

"$C_{1-6}$haloalkyl" refers to a $C_{1-6}$alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like.

"Heterocycle" or "heterocyclyl" means a 4- to 7-membered monocyclic, or 7- to 10-membered bicyclic, heterocyclic ring which is either saturated, unsaturated or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. An aromatic heterocycle is referred to herein as a "heteroaryl", and includes (but is not limited to) furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, oxadiazolyl, thiadiazolyl, benzisoxazolyl, triazolyl, tetrazolyl, indazolyl and quinazolinyl. In addition to the heteroaryls listed above, heterocycles also include morpholinyl, pyrrolidinonyl, pyrrolidinyl, piperidinyl, piperazinyl, and the like. In addition, heterocycles also include benzothiophen-2-yl, 2,3-dihydrobenzo-1,4-dioxin-6-yl, benzo-1,3-dioxol-5-yl and the like.

The term "substituted" as used herein (for example, in the context of a substituted heterocyclyl or substituted aryl) means that at least one hydrogen atom is replaced with a substituent. "Substituents" within the context of this invention include halogen, hydroxy, oxo, cyano, nitro, imino, thioxo, amino, alkylamino, dialkylamino, alkyl, alkoxy, alkylthio, haloalkyl, aryl, aralkyl, heteroaryl, heteroarylalkyl, heterocycle and heterocyclealkyl, as well as —$NR_aR_b$, —$NR_aC(=O)R_b$, —$NR_aC(=O)NR_aNR_b$, —$NR_aC(=O)OR_b$—$NR_aSO_2R_b$, —$C(=O)R_a$, —$C(=O)OR_a$, —$C(=O)NR_aR_b$, —$OC(=O)NR_aR_b$, —$OR_a$, —$SR_a$, —$SOR_a$, —$S(=O)_2R_a$, —$OS(=O)_2R_a$, —$S(=O)_2OR_a$, =$NSO_2R_a$ and —$SO_2NR_aR_b$. In the foregoing, $R_a$ and $R_b$ in this context may be the same or different and independently hydrogen, alkyl, haloalkyl, cycloalkyl, aryl, aralkyl, heterocyclyl. In addition, the foregoing substituents may be further substituted with one or more of the above substituents.

In further embodiments of structure (I), X is —O— and the compound has the following structure (II):

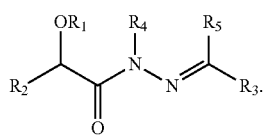

(II)

In more specific embodiments of structure (II):
$R_1$ is $C_{1-6}$alkyl, $C_{1-6}$haloalkyl, $C_{1-6}$aralkyl, aryl, —$(CH_2)_nO(CH_2)_mCH_3$ or —$(CH_2)_nN(CH_3)_2$;
$R_2$ is substituted or unsubstituted heterocyclyl, substituted phenyl, or substituted or unsubstituted naphthyl;
$R_3$ is substituted or unsubstituted heterocyclyl, or substituted or unsubstituted aryl; and
$R_4$ and $R_5$ are the same or different and independently hydrogen, $C_{1-6}$alkyl or $C_{1-6}$haloalkyl;
n is 1, 2, 3, 4, 5 or 6; and
m is 0, 1, 2, 3, 4, 5 or 6.

In further more specific embodiments of structure (II), $R_4$ and $R_5$ are the same or different and independently hydrogen or $C_{1-6}$alkyl (such as, for example, hydrogen), $R_1$ is $C_{1-6}$alkyl (such as, for example, methyl, ethyl or isopropyl), $R_3$ is substituted phenyl (such as, for example, 3,4,5-trimethoxyphenyl or 4-bromo-3,5-dimethoxyphenyl) and/or $R_2$ is substituted or unsubstituted phenyl (such as, for example, 4-morpholinophenyl or 4-(1H-pyrazol-1-yl)phenyl), substituted or unsubstituted naphthyl, or substituted or unsubstituted heteroaryl.

In other further embodiments of structure (I), X is —S— and the compound has the following structure (III):

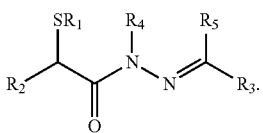

(III)

In more specific embodiments of structure (III):
$R_1$ is $C_{1-6}$alkyl, $C_{1-6}$haloalkyl, —$(CH_2)_nO(CH_2)_mCH_3$ or —$(CH_2)_nN(CH_3)_2$;

$R_2$ and $R_3$ are the same or different and independently substituted or unsubstituted heterocyclyl, or substituted or unsubstituted aryl; and
$R_4$ and $R_5$ are the same or different and independently hydrogen, $C_{1-6}$alkyl or $C_{1-6}$haloalkyl;
n is 1, 2, 3, 4, 5 or 6; and
m is 0, 1, 2, 3, 4, 5 or 6.

In further more specific embodiments of structure (III), $R_4$ and $R_5$ are the same or different and independently hydrogen or $C_{1-6}$alkyl (such as, for example, hydrogen), $R_1$ is $C_{1-6}$alkyl (such as, for example, methyl, ethyl or isopropyl), $R_3$ is substituted phenyl (such as, for example, 3,4,5-trimethoxyphenyl or 4-bromo-3,5-dimethoxyphenyl) and/or $R_2$ is substituted or unsubstituted phenyl (such as, for example, 4-morpholinophenyl or 4-(1H-pyrazol-1-yl)phenyl), substituted or unsubstituted naphthyl, or substituted or unsubstituted heteroaryl.

In more specific embodiments of structure (IV):
$R_1$ is hydrogen, $C_{1-6}$alkyl, $C_{1-6}$haloalkyl, $C_{1-6}$aralkyl, aryl, —$(CH_2)_nO(CH_2)_mCH_3$ or —$(CH_2)_nN(CH_3)_2$;
$R_2$ is

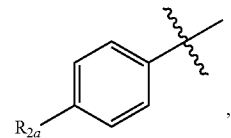

wherein
$R_{2a}$ is —$N(R_{2b}R_{2c})$ or a heterocyclic ring containing at least one N ring atom, and
$R_{2b}$ and $R_{2c}$ are the same or different and independently hydrogen, $C_{1-6}$alkyl, $C_{1-6}$haloalkyl, $C_{1-6}$aralkyl or aryl;
$R_3$ is

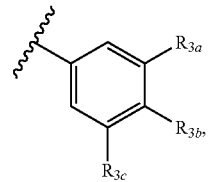

wherein
$R_{3a}$ is —$C_{1-6}$alkoxy,
$R_{3b}$ is halogen, and
$R_{3c}$ is —$C_{1-6}$alkoxy;
$R_4$ and $R_5$ are the same or different and independently hydrogen, $C_{1-6}$alkyl or $C_{1-6}$haloalkyl;
n is 1, 2, 3, 4, 5 or 6; and
m is 0, 1, 2, 3, 4, 5 or 6.

In other more specific embodiments of structure (IV):
$R_1$ is hydrogen, $C_{1-6}$alkyl, $C_{1-6}$haloalkyl, $C_{1-6}$aralkyl, aryl, —$(CH_2)_nO(CH_2)_mCH_3$ or —$(CH_2)_nN(CH_3)_2$;
$R_2$ is

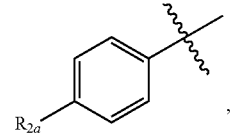

wherein
R$_{2a}$ is —N(R$_{2b}$R$_{2c}$) or a heterocyclic ring containing at least one N ring atom, provided that R$_{2a}$ is not 1H-tetrazol-1-yl, and
R$_{2b}$ and R$_{2c}$ are the same or different and independently hydrogen, C$_{1-6}$alkyl, C$_{1-6}$haloalkyl, C$_{1-6}$aralkyl or aryl;
R$_3$ is

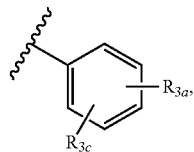

wherein
R$_{3a}$ is —C$_{1-6}$alkoxy, and
R$_{3c}$ is —C$_{1-6}$alkoxy;
R$_4$ and R$_5$ are the same or different and independently hydrogen, C$_{1-6}$alkyl or C$_{1-6}$haloalkyl;
n is 1, 2, 3, 4, 5 or 6; and
m is 0, 1, 2, 3, 4, 5 or 6.

In other more specific embodiments of structure (IV), R$_4$ and R$_5$ are hydrogen or C$_{1-6}$alkyl (such as, for example, hydrogen), R$_1$ is hydrogen or C$_{1-6}$alkyl (such as, for example, methyl, ethyl, isopropyl or cyclopropyl), R$_3$ is substituted phenyl (such as, for example, 3,4,5-trimethoxyphenyl or 4-bromo-3,5-dimethoxyphenyl) and/or R$_2$ is substituted or unsubstituted phenyl (such as, for example, 4-morpholinophenyl or 4-(1H-pyrazol-1-yl)phenyl) or substituted or unsubstituted naphthyl.

The compounds of the present invention may be prepared by known organic synthesis techniques, including the methods described in more detail in the Examples, or in some instances may be obtained from commercially available sources. In general, the compounds of structures (I) and (IV) above may be made by the following reaction schemes, wherein all substituents are as defined above unless indicated otherwise.

Reaction Scheme 1

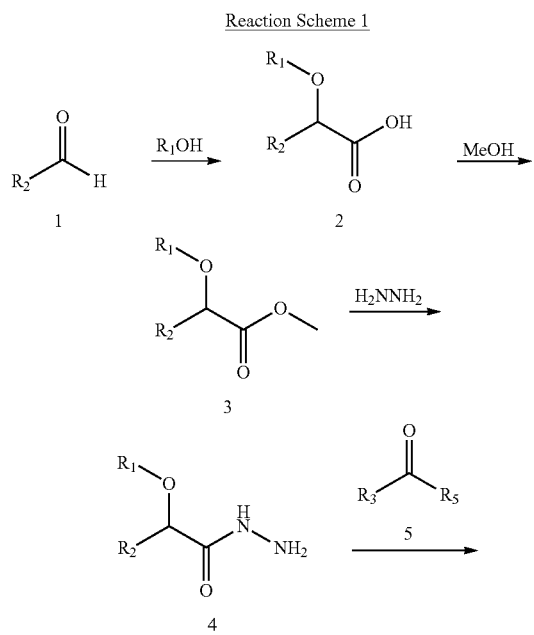

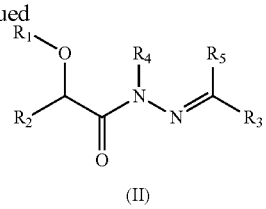

(II)

Compounds of formula 1 can be obtained commercially or synthesized through standard literature methods. Compounds of formula 1 can be reacted with a variety of alcohols using the method disclosed in U.S. Pat. No. 7,129,238 (which is incorporated herein by reference in its entirety) to provide compounds of formula 2. Compounds of formula 2 can be heated with a variety of alcohols under acidic conditions to provide compounds of formula 3. Compounds of formula 3 can then be heated to reflux in the presence of hydrazine hydrate in an alcoholic solvent to provide compounds of formula 4. Compounds of formula 4 can be reacted with aldehydes or ketones of formula 5 to provide compounds of structure (II).

Reaction Scheme 2

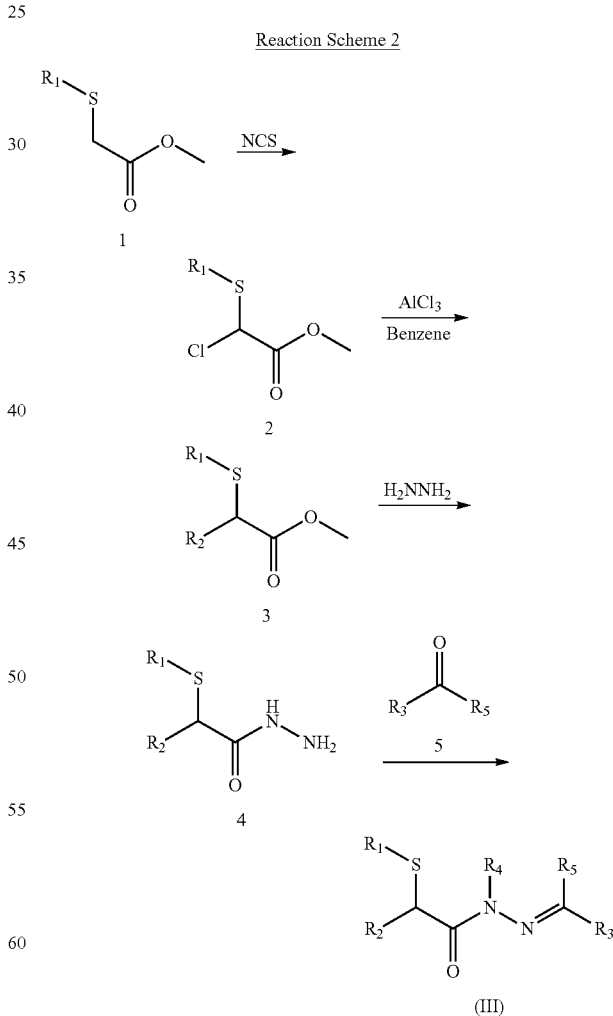

(III)

Compounds of formula 1 can be obtained commercially or synthesized through standard literature methods. Compounds of formula 1 can be reacted with a variety of halogenating reagents such as NCS to provide compounds of formula 2. Compounds of formula 2 can be reacted with aromatic compounds under Friedel-Crafts conditions to provide compounds of formula 3. Compounds of formula 3 can then be heated to reflux in the presence of hydrazine hydrate in an alcoholic solvent to provide compounds of formula 4. Compounds of formula 4 can be reacted with aldehydes or ketones of formula 5 to provide compounds of structure (III).

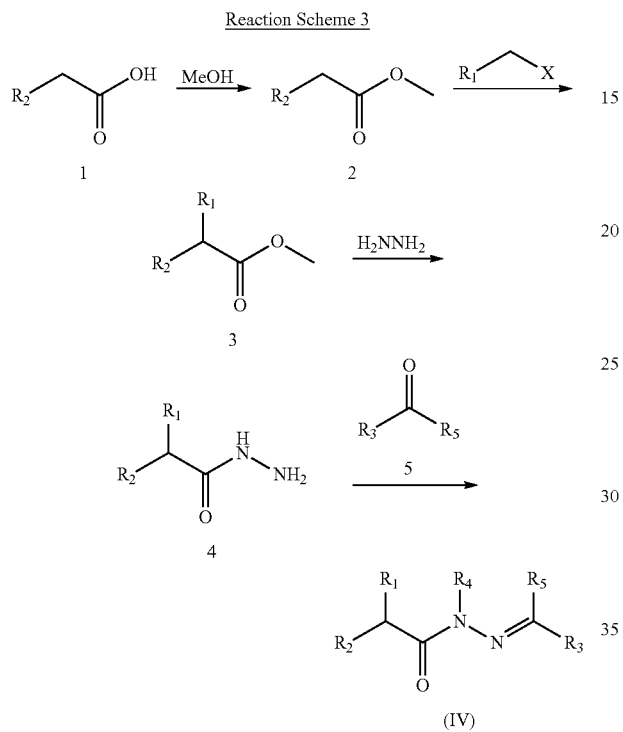

Reaction Scheme 3

Compounds of formula 1 can be obtained commercially or synthesized through standard literature methods. Compounds of formula 1 can be reacted with a variety of alcohols under acidic conditions to provide compounds of formula 2. Compounds of formula 2 can be treated with a variety of bases and alkylating reagents to provide compounds of formula 3. Compounds of formula 3 can then be heated to reflux in the presence of hydrazine hydrate in an alcoholic solvent to provide compounds of formula 4. Compounds of formula 4 can be reacted with aldehydes or ketones of formula 5 to provide compounds of structure (IV).

The compounds of the present invention may generally be utilized as the free acid or free base. Alternatively, the compounds of this invention may be used in the form of acid or base addition salts. Acid addition salts of the free amino compounds of the present invention may be prepared by methods well known in the art, and may be formed from organic and inorganic acids. Suitable organic acids include maleic, fumaric, benzoic, ascorbic, succinic, methanesulfonic, acetic, trifluoroacetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids. Base addition salts included those salts that form with the carboxylate anion and include salts formed with organic and inorganic cations such as those chosen from the alkali and alkaline earth metals (for example, lithium, sodium, potassium, magnesium, barium and calcium), as well as the ammonium ion and substituted derivatives thereof (for example, dibenzylammonium, benzylammonium, 2-hydroxyethylammonium, and the like). Thus, the term "pharmaceutically acceptable salt" of structures (I) through (IV) is intended to encompass any and all acceptable salt forms.

In addition, prodrugs are also included within the context of this invention. Prodrugs are any covalently bonded carriers that release a compound of structures (I) through (IV) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol and amine functional groups of the compounds of structures (I) through (IV). Further, in the case of a carboxylic acid (—COOH), esters may be employed, such as methyl esters, ethyl esters, and the like.

In addition, prodrugs having the following structures (I-A), (I-B), (IV-A) and (IV-B) are included within the scope of this invention:

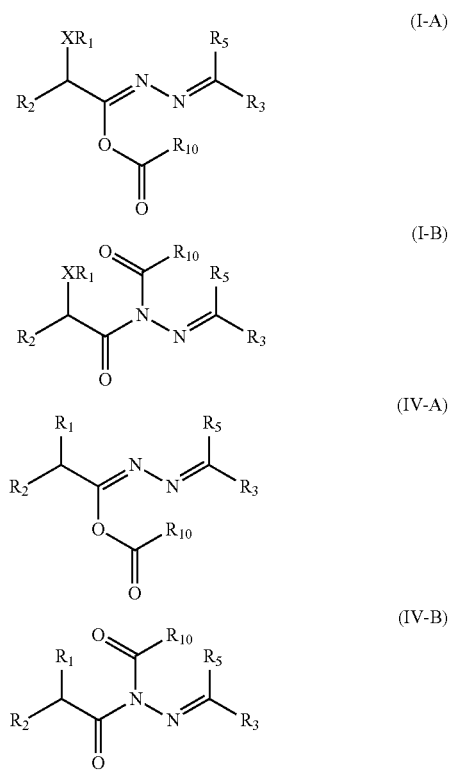

wherein $R_{10}$ is $C_{1-6}$alkyl, aryl, —$OC_{1-6}$alkyl, —O-aryl or —$NC_{1-6}$alkyl. Enolic prodrugs of structure (I-A) and (IV-A) may be prepared by treating a compound of structure (I) or structure (IV), respectively, with a base, such as triethylamine, in a solvent, such as dichloromethane, followed by the addition of an electrophile, such as acetyl chloride. N-acylated prodrugs of structure (I-B) and (IV-B) may be prepared via thermal rearrangement by heating a prodrug of structure (I-A) or (IV-A), respectively, in a solvent, such as toluene. See, e.g., Carpino et al., *J. Org. Chem.*, 53, 6047-6053 (1988); Geita et al., *Zhurnal Organicheskoi Khimii*, 13(7), 1461-1465 (1977) (translation available from *Institute of Organic Synthesis, Academy of Sciences of the Latvian SSR*, 1346-1350); Maroulis et al., *J. Heterocyclic Chem.*, 21, 1653-1656 (1984); Monge et al., *J. Heterocyclic Chem.*, 21, 397-400 (1984); and Singh et al., *Tetrahedron Letters*, 29, 2711-2714 (1973).

With regard to stereoisomers, the compounds of structures (I) through (IV) may have chiral centers and may occur as racemates, racemic mixtures and as individual enantiomers or diastereomers. All such isomeric forms are included within the present invention, including mixtures thereof. Furthermore, some of the crystalline forms of the compounds of structures (I) through (IV) may exist as polymorphs, which are included in the present invention. In addition, some of the compounds of structures (I) through (IV) may also form solvates with water or other organic solvents. Such solvates are similarly included within the scope of this invention.

In another embodiment of the invention, pharmaceutical compositions containing one or more compounds of structures (I) through (IV) are disclosed. For the purposes of administration, the compounds of the present invention may be formulated as pharmaceutical compositions. Pharmaceutical compositions of the present invention comprise one or more compounds of the present invention and a pharmaceutically acceptable carrier and/or diluent. The PDE10 inhibitor is present in the composition in an amount which is effective to treat a particular disorder—that is, in an amount sufficient to achieve desired PDE10 inhibition, and preferably with acceptable toxicity to the warm-blooded animal. Typically, the pharmaceutical compositions of the present invention may include a PDE100 inhibitor in an amount from 0.1 mg to 250 mg per dosage depending upon the route of administration, and more typically from 1 mg to 60 mg. Appropriate concentrations and dosages can be readily determined by one skilled in the art.

In general terms, a typical daily dosage might range from about 1 µg/kg to 100 mg/kg, preferably 0.01-100 mg/kg, more preferably 0.1-70 mg/kg, depending on the type and severity of the disease whether, for example, by one or more separate administrations. For repeated administrations over several days or longer, depending on the condition, the treatment is sustained until a desired suppression of disease symptoms occurs. However, other dosage regimens may be useful. The progress of this therapy can be monitored by standard techniques and assays. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Pharmaceutically acceptable carrier and/or diluents are familiar to those skilled in the art. For compositions formulated as liquid solutions, acceptable carriers and/or diluents include saline and sterile water, and may optionally include antioxidants, buffers, bacteriostats and other common additives. The compositions can also be formulated as pills, capsules, granules, or tablets which contain, in addition to a PDE10 inhibitor, diluents, dispersing and surface active agents, binders, and lubricants. One skilled in this art may further formulate the PDE10 inhibitor in an appropriate manner, and in accordance with accepted practices, such as those disclosed in *Remington's Pharmaceutical Sciences*, Gennaro, Ed., Mack Publishing Co., Easton, Pa. 1990.

In another embodiment, the present invention provides a method for treating diseases such as (but not limited to) psychotic disorders, anxiety disorders, movement disorders and/or neurological disorders such as Parkinson's disease, Huntington's disease, Alzheimer's disease, encephalitis, phobias, epilepsy, aphasia, Bell's palsy, cerebral palsy, sleep disorders, pain, Tourette's syndrome, schizophrenia, delusional disorders, bipolar disorders, post-traumatic stress disorders, drug-induced psychosis, panic disorders, obsessive-compulsive disorders, attention-deficit disorders, disruptive behavior disorders, autism, depression, dementia, cognitive disorders, epilepsy, insomnias and multiple sclerosis as discussed above. Such methods include administering of a compound of the present invention to a warm-blooded animal in an amount sufficient to treat the condition. In this context, "treat" includes prophylactic administration. Such methods include systemic administration of a PDE10 inhibitor of this invention, preferably in the form of a pharmaceutical composition as discussed above. As used herein, systemic administration includes oral and parenteral methods of administration, including subcutaneous, intramuscular, intracranial, intraorbital, ophthalmic, intraventricular, intracapsular, intraarticular, intraspinal, intracisternal, intraperitoneal, intranasal, aerosol, intravenous, intradermal, inhalational, transdermal, transmucosal, and rectal administration.

For oral administration, suitable pharmaceutical compositions of PDE10 inhibitors include powders, granules, pills, tablets, and capsules as well as liquids, syrups, suspensions, and emulsions. These compositions may also include flavorants, preservatives, suspending, thickening and emulsifying agents, and other pharmaceutically acceptable additives and excipients. For parenteral administration, the compounds of the present invention can be prepared in aqueous injection solutions which may contain, in addition to the PDE10 inhibitor, buffers, antioxidants, bacteriostats, and other additives and excipients commonly employed in such solutions. Compositions of the present invention may be carried in a delivery system to provide for sustained release or enhanced uptake or activity of the therapeutic compound, such as a liposomal or hydrogel system for injection, a microparticle, nanopartical or micelle system for oral or parenteral delivery, or a staged capsule system for oral delivery.

In a further advantage of the present invention, compounds of structures (I) through (IV) are expected to avoid or reduce metabolic side effects associated with conventional antipsychotics, in particular the incidence of therapeutically induced obesity. For example, chronic use of olanzapine (Zyprexa®), the most widely prescribed medication to treat schizophrenia, and related atypical antipsychotics is associated with significant metabolic side effects including obesity and associated conditions such as diabetes.

In animals, subchronic treatment with olanzapine stimulates food intake and increases body weight, consistent with human situations. Furthermore, olanzapine acutely lowers blood leptin levels. Leptin is a satiety hormone produced from adipose tissues, and decrease of leptin level stimulates appetite. It is theorized that olanzapine could stimulate food intake at least partly by reducing leptin levels. Acute administration of olanzapine also changes the animal's response in glucose and insulin levels in glucose tolerance tests, which may also be directly linked to olanzapine's effect in food intake and body weight gain. Examination of the acute effect of PDE10 inhibitors of the present invention on metabolism, such as leptin, insulin and glucose changes during a metabolic challenge in standard animal models, as well as the chronic effect of PDE10 inhibitors of the present invention in food intake, body weight and energy homeostasis, in comparison with olanzapine should provide evidence to the pharmaceutical advantage of PDE10 inhibitors as antipsychotics in terms of less side-effect concerns.

The compositions of the present invention may be administered in combination with one or more additional therapeutic agents, in combination or by concurrent or sequential administration. Suitable additional agents (i.e., adjuvants) may include typical antipsychotics that block dopamine-$D_2$ receptors and serotonin $5HT_2$ receptors, e.g., haloperidol, fluphenazine, chlorpromazine, and atypical antipsychotics, e.g., clozapine, olanzapine, risperidone, quetiapine, ziprasidone.

Compounds of this invention may be assayed to determine their $IC_{50}$ values by a modification of the two-step method of Thompson and Appleman (*Biochemistry* 10; 311-316; 1971). In short, cAMP is spiked with ($^3$H)cAMP and incubated with PDE10 and various concentrations of a compound of structure (I). After the appropriate incubation time, the reaction is terminated by heating. The mixture is then subjected to treatment with snake venom phosphatase. The phosphatase hydrolyzes any AMP in the mixture, but leaves unreacted cAMP intact. Thus, by separating cAMP from the mixture and determining its concentration (by radiography), the percent of inhibition can be determined. $IC_{50}$ values can be calculated by performing the experiment at several concentrations using standard graphical means. A detailed description of the actual technique used for $IC_{50}$ assays as set forth in following Examples. To this end, PDE10 inhibitors of the invention have an $IC_{50}$ of 100 μM or less, generally less than 10 μM, and typically less than 1 μM.

The following examples are provided for purposes of illustration, not limitation.

EXAMPLES

Example 1

Synthesis of (E)-2-Methoxy-2-(naphthalen-2-yl)-N'-(3,4,5-trimethoxybenzylidene)acetohydrazide 2-Hydroxy-2-(naphthalen-2-yl)acetic acid

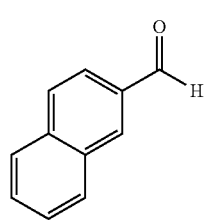

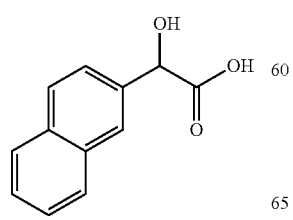

A solution of 2-naphthaldehyde (2.0 g, 1.0 eq), benzyltriethylammonium chloride (BTEAC) (0.13 g), and 50% aqueous NaOH (2.3 mL), and (3-cyclodextrin (0.10 g) in chloroform (10 mL) was heated at 55° C. for 12 hours. The mixture was then poured into water and the solution washed with EtOAc. The aqueous layer was then acidified to pH 1 by dropwise addition of HCl (conc.). This was extracted with EtOAc, dried over $Na_2SO_4$, filtered and concentrated under reduced pressure to yield a yellow oil (0.75 g, 29%) that was not further purified.

Methyl 2-hydroxy-2-(naphthalen-2-yl)acetate

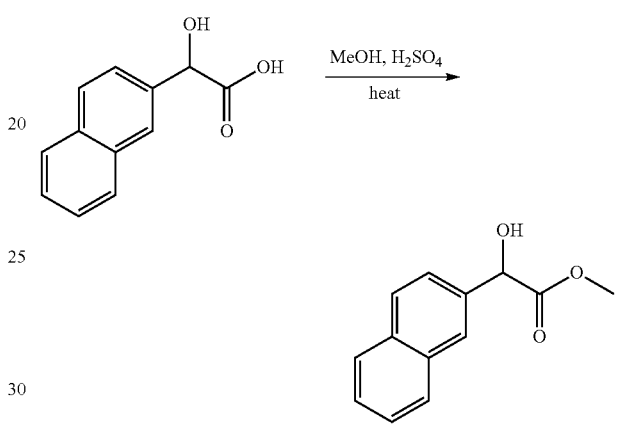

To a stirred solution of 2-hydroxy-2-(naphthalen-2-yl) acetic acid (0.75 g, 1 eq) in dry MeOH was added sulfuric acid (0.1 mL) dropwise and heated to reflux. Stirring was then continued for 2 hours. The reaction mixture was then cooled and poured into saturated aqueous $NaHCO_3$ and extracted with EtOAc. The combined organic fractions were dried over $Na_2SO_4$, filtered, and concentrated under reduced pressure to yield an oil (0.63 g, 78%) that was not further purified.

Methyl 2-methoxy-2-(naphthalen-2-yl)acetate

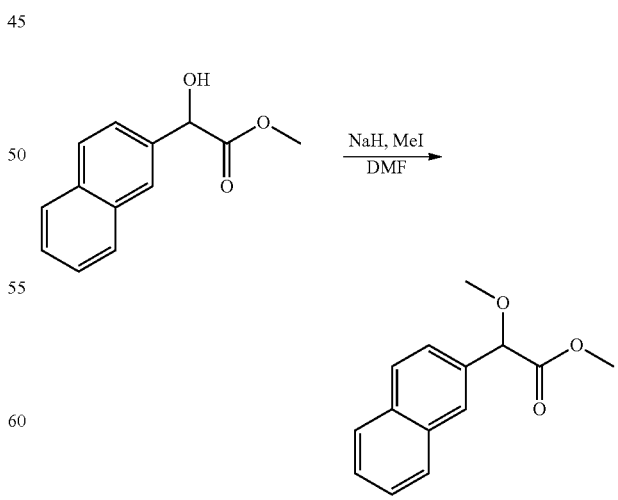

To a stirred solution of methyl 2-hydroxy-2-(naphthalen-2-yl)acetate (0.63 g, 1 eq) in dry DMF was added NaH (0.45 g, 4 eq) and methyl iodide (0.74 mL, 4.1 eq). Stirring was then continued for 24 hours. The reaction mixture was then poured into ethyl acetate and washed with H₂O. The combined organic fractions were dried over Na₂SO₄, filtered, and concentrated under reduced pressure to yield an oil that was purified by column chromatography using ethyl acetate and hexanes to yield an oil (0.358 g, 53%).

2-Methoxy-2-(naphthalen-2-yl)acetohydrazide

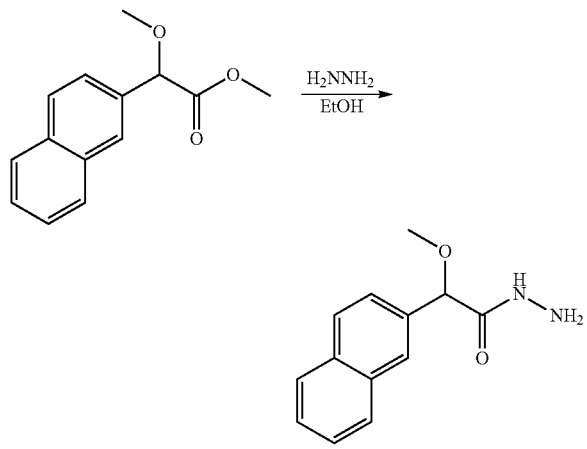

A stirred solution of methyl 2-methoxy-2-(naphthalen-2-yl)acetate (0.358 g, 1 eq) and hydrazine hydrate (4 mL) was heated to reflux for 1 hour. The reaction mixture was then cooled and the solvents removed under reduced pressure. The crude oil was diluted with EtOAc and washed with H₂O and the organic phase dried over Na₂SO₄, filtered, and the solvents removed under reduced pressure to yield a yellow oil (0.17 g, 47%) that was used without further purification.

(E)-2-Methoxy-2-(naphthalen-2-yl)-N'-(3,4,5-trimethoxybenzylidene)acetohydrazide

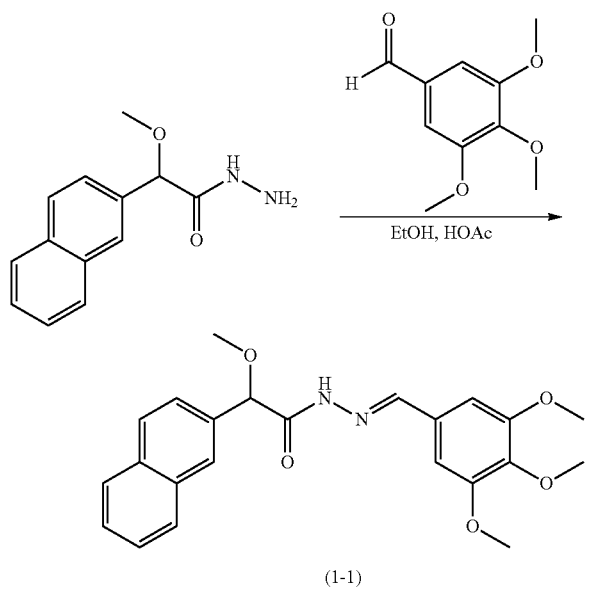

In a round-bottom glass flask equipped with a magnetic stir bar methyl 2-methoxy-2-(naphthalen-2-yl)acetohydrazide (0.17 g, 1 eq) was dissolved in ethanol (10 mL) at room temperature. To this well stirred solution, acetic acid (10 mL) and 3,4,5-trimethoxy-benzaldehyde (0.145 g, 1 eq) were added, and the reaction mixture was heated at 90° C. for 2 hours. The mixture was then cooled and the crude product was diluted with Et₂O and filtered and the solid was washed thoroughly with Et₂O to yield 0.176 g, 58% of the product (1-1) as a white solid.

Example 2

Synthesis of (E)-2-(2,3-Dihydrobenzo[b][1,4]dioxin-6-yl)-2-methoxy-N'-(3,4,5-trimethoxybenzylidene)acetohydrazide 2-(2,3-Dihydrobenzo[b][1,4]dioxin-6-yl)-2-methoxyacetic acid

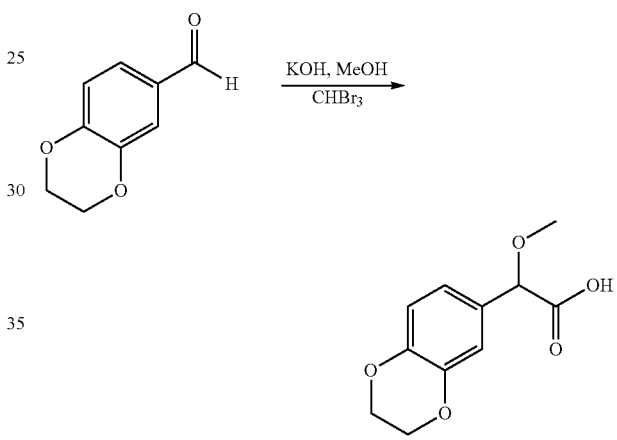

To a stirred solution of 2,3-dihydrobenzo[b][1,4]dioxine-6-carbaldehyde (3.0 g, 1.0 eq) and bromoform (2.0 mL, 1.27 eq) in MeOH (18 mL) and dioxane (18 mL) was added dropwise a solution of potassium hydroxide (5.1 g, 5.0 eq) in MeOH (18 mL) over 15 minutes. Stirring was then continued for 24 hours. The mixture was then poured into water and the solution washed with EtOAc and acidified to pH 1 by dropwise addition of HCl (conc.). This was extracted with EtOAc, dried over Na₂SO₄, filtered and concentrated under reduced pressure to yield a yellow oil (4.1 g) that was not further purified.

Methyl 2-(2,3-dihydrobenzo[b][1,4]dioxin-6-yl)-2-methoxyacetate

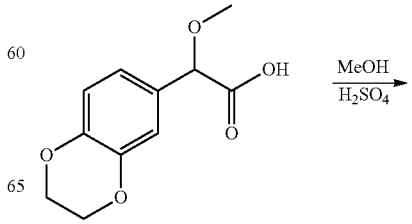

-continued

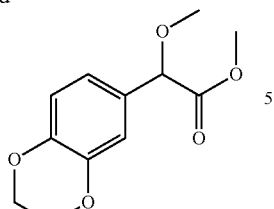

To a stirred solution of 2-(2,3-dihydrobenzo[b][1,4]di-oxin-6-yl)-2-methoxyacetic acid (18.3 mmol) in dry MeOH was added sulfuric acid (2.5 mL) dropwise and heated at 90° C. Stirring was then continued for 3 hours. The reaction mixture was then cooled and poured into saturated aqueous NaHCO$_3$ and extracted with EtOAc. The combined organic fractions were dried over Na$_2$SO$_4$, filtered, and concentrated under reduced pressure to yield an oil (3.7 g) that was not further purified.

2-(2,3-Dihydrobenzo[b][1,4]dioxin-6-yl)-2-methoxyacetohydrazide

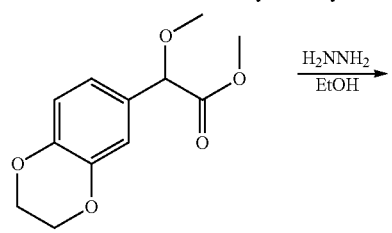

To a stirred solution of methyl 2-(2,3-dihydrobenzo[b][1,4]dioxin-6-yl)-2-methoxyacetate (18.3 mmol) in anhydrous EtOH (150 mL) was added hydrazine hydrate (73.2 mmol, 4 eq) and heated to 90° C. Stirring was then continued for 24 hours. The reaction mixture was then cooled and the solvents removed under reduced pressure. The crude oil was diluted with EtOAc and washed with H$_2$O and the organic phase dried over Na$_2$SO$_4$, filtered, and the solvents removed under reduced pressure to yield a yellow oil (3.5 g) that was used without further purification.

(E)-2-(2,3-Dihydrobenzo[b][1,4]dioxin-6-yl)-2-methoxy-N'-(3,4,5-trimethoxybenzylidene)acetohydrazide

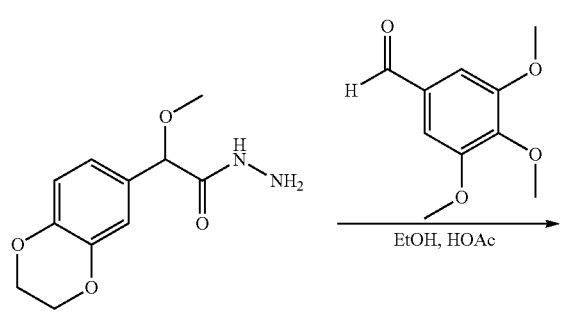

-continued

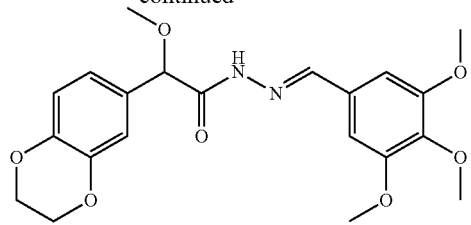

(2-1)

In a round-bottom glass flask equipped with a magnetic stir bar 2-(2,3-dihydrobenzo[b][1,4]dioxin-6-yl)-2-methoxyacetohydrazide (1 eq., 1.1 mmol; 260 mg) was dissolved in ethanol (10 mL) at room temperature. To this well stirred solution, acetic acid (~3 drops) and 3,4,5-trimethoxy-benzaldehyde (1.2 eq, 1.3 mmol; 260 mg) were added, and the reaction mixture was heated for 12 hours. The mixture was then cooled and the crude product was diluted with Et$_2$O and filtered and the solid was washed thoroughly with Et$_2$O to yield: 300 mg (65%) of (2-1).

Example 3

Synthesis of (E)-2,2-Diphenyl-N'-(3,4,5-trimethoxy-benzylidene)acetohydrazide

Methyl 2,2-diphenylacetate

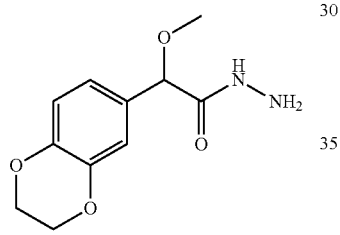

To a stirred solution of 2,2-diphenylacetic acid (1 gram, 1 equiv) in dry MeOH (50 mL) was added sulfuric acid (0.4 mL) dropwise and heated to reflux. Stirring was then continued for 3 hours. The reaction mixture was then cooled and poured into saturated aqueous NaHCO$_3$ and extracted with EtOAc. The combined organic fractions were dried over Na$_2$SO$_4$, filtered, and concentrated under reduced pressure to yield an oil (1.0 g, 93%) that was not further purified.

2,2-Diphenylacetohydrazide

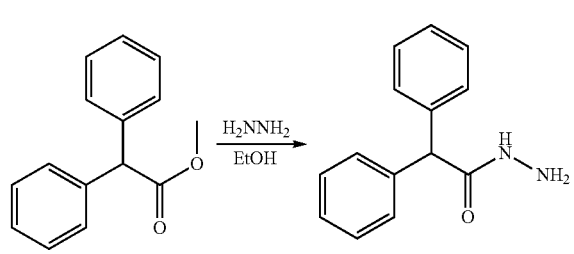

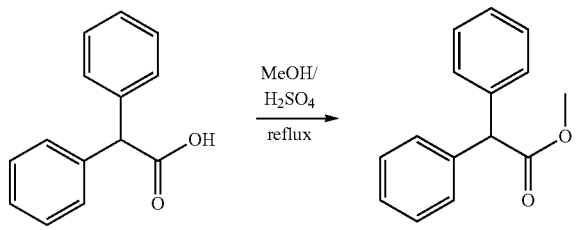 [SMILES: O=C(O)C(c1ccccc1)c1ccccc1 ; COC(=O)C(c1ccccc1)c1ccccc1]

To a stirred solution of methyl 2,2-diphenylacetate (0.5 g, 1 equiv) in anhydrous EtOH (150 mL) was added hydrazine hydrate (8 mL) and heated to reflux. Stirring was then continued for 1 hour. The reaction mixture was then cooled and the solvents removed under reduced pressure. The crude oil was diluted with EtOAc and washed with H$_2$O and the organic phase dried over Na$_2$SO$_4$, filtered, and the solvents removed under reduced pressure to yield a yellow oil (0.97 g, 97%) that was used without further purification.

(E)-2,2-Diphenyl-N'-(3,4,5-trimethoxybenzylidene)acetohydrazide

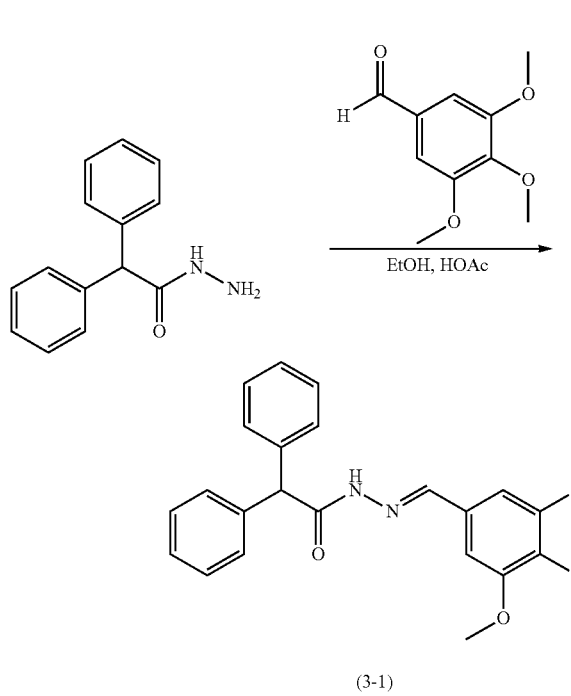

(3-1)

In a round-bottom glass flask equipped with a magnetic stir bar 2,2-diphenylacetohydrazide (0.33 g, 1 equiv) was dissolved in ethanol (20 mL) at room temperature. To this well stirred solution, acetic acid (1.4 mL) and 3,4,5-trimethoxybenzaldehyde (0.29 g, 1 equiv) were added, and the reaction mixture was heated to reflux for 2 hours. The mixture was then cooled and the crude product was diluted with Et$_2$O and filtered and the solid was washed thoroughly with Et$_2$O to yield the product (3-1) (0.056 g, 10%).

Example 4

Synthesis of (E)-N'-(3,4-Dimethoxybenzylidene)-2-(methylthio)-2-phenylacetohydrazide Methyl 2-chloro-2-(methylthio)acetate

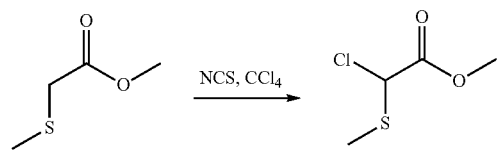

Methyl 2-chloro-2-(methylthio)acetate can be synthesized according to literature procedures (Boehme, H.; Krack, W.; Justus Liebigs Annalen der Chemie; 1977; 51-60. Iwama, Tetsuo; Harutoshi, Matsumoto; Tadashi, Kataoka; Journal of the Chemical Society, Perkin Transactions 1: Organic and Bio-Organic Chemistry (1972-1999); 1997; 835-844).

Methyl 2-(methylthio)-2-phenylacetate

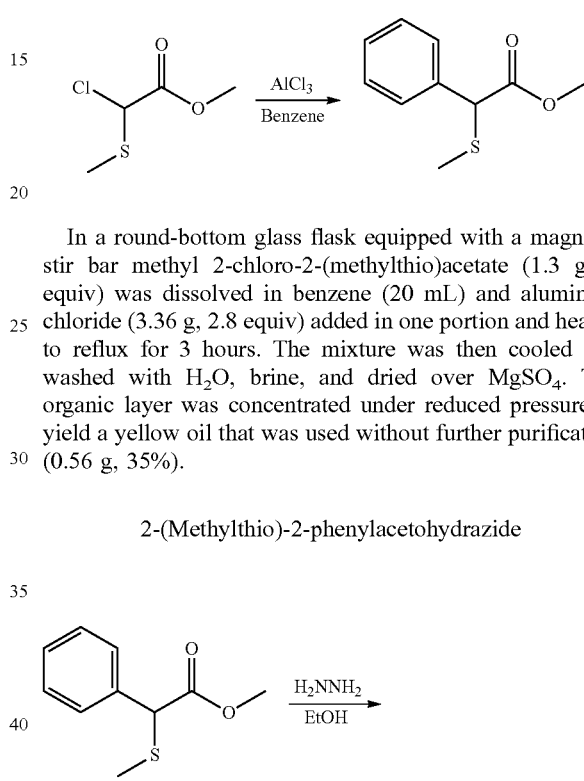

In a round-bottom glass flask equipped with a magnetic stir bar methyl 2-chloro-2-(methylthio)acetate (1.3 g, 1 equiv) was dissolved in benzene (20 mL) and aluminum chloride (3.36 g, 2.8 equiv) added in one portion and heated to reflux for 3 hours. The mixture was then cooled and washed with H$_2$O, brine, and dried over MgSO$_4$. The organic layer was concentrated under reduced pressure to yield a yellow oil that was used without further purification (0.56 g, 35%).

2-(Methylthio)-2-phenylacetohydrazide

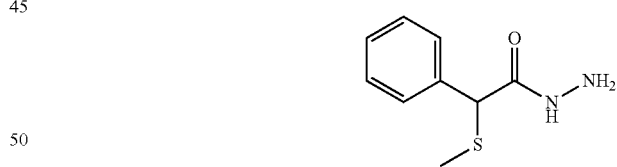

To a stirred solution of methyl 2-(methylthio)-2-phenylacetate (0.300 g, 1 equiv) in anhydrous EtOH (5 mL) was added hydrazine hydrate (0.15 mL, 2 equiv) and heated to reflux. Stirring was then continued for 18 hours. The reaction mixture was then cooled and the solvents removed under reduced pressure. The crude oil was diluted with EtOAc and washed with H$_2$O and the organic phase dried over Na$_2$SO$_4$, filtered, and the solvents removed under reduced pressure to yield a yellow oil which was purified by flash chomatography on silica gel using ethyl acetate and hexanes. The purified product was a white solid (193 mg, 66%).

23

(E)-N'-(3,4-Dimethoxybenzylidene)-2-(methylthio)-2-phenylacetohydrazide

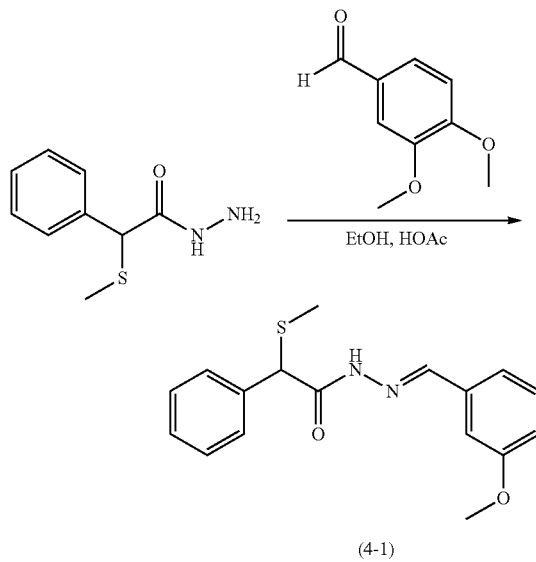

(4-1)

In a round-bottom glass flask equipped with a magnetic stir bar 2-(methylthio)-2-phenylacetohydrazide (0.132 g, 1 equiv) was dissolved in ethanol (5 mL) at room temperature. To this well stirred solution, acetic acid (2 drops) and 3,4-dimethoxybenzaldehyde (0.111 g, 1 equiv) were added, and the reaction mixture was heated to reflux for 12 hours. The mixture was then cooled and the crude product was diluted with $Et_2O$ and filtered and the solid was washed thoroughly with $Et_2O$ to yield the product (4-1) (0.120 g, 52%).

Example 5

Synthesis of (1Z, N'E)-2-Methoxy-2-(naphthalen-1-yl)-N'-(3,4,5-trimethoxybenzylidene)acetohydrazonic pivalic anhydride

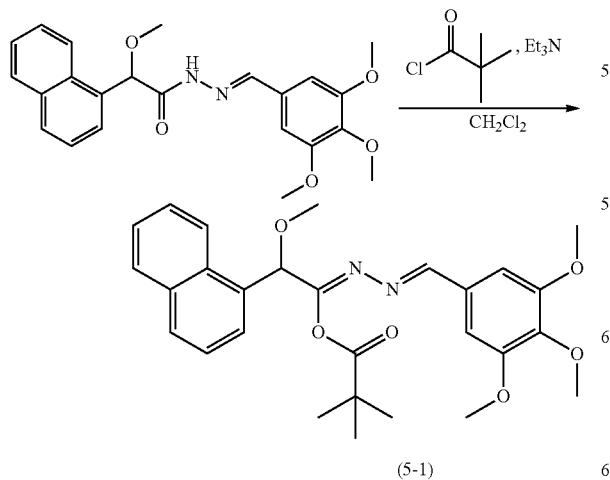

(5-1)

24

An oven dried flask was charged with (E)-2-methoxy-2-(naphthalen-1-yl)-N'-(3,4,5-trimethoxybenzylidene)acetohydrazide (0.1 g, 0.25 mmol) (prepared according to the foregoing procedures) and put under argon. Anhydrous dichloromethane (20 mL), triethylamine (0.17 mL, 1.2 mmol), and pivaloyl chloride (0.081 mL, 0.67 mmol) were added and the mixture was stirred at room temperature for 18 hours. The mixture was poured into $H_2O$ and the resulting aqueous layer was extracted with dichloromethane twice. The combined organics were washed with water and brine, dried over $Na_2SO_4$, filtered and concentrated in vacuo. Purification by chromatography (ethyl acetate-hexanes) gave the product (5-1) as a light yellow solid (0.12 g, 100%).

Example 6

Synthesis of (E)-2-Methoxy-2-(quinolin-5-yl)-N'-(3,4,5-trimethoxybenzylidene)-acetohydrazide

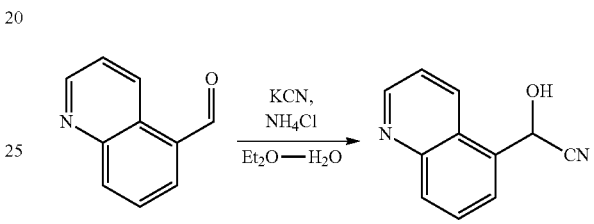

A suspension of quinoline-5-carboxaldehyde (3.12 g, 19.9 mmol) in diethyl ether (42 mL) was cooled over an ice bath. Cold solutions of $NH_4Cl$ (1.09 g, 18.7 mmol) in water (4.5 mL) and KCN (1.34 g, 20.5 mmol) in water (4.5 mL) were added successively. The mixture was allowed to warm gradually to room temperature with rapid stirring. After 1.75 hours total reaction time, the mixture was cooled over an ice bath and the tan solid was collected on a Büchner funnel, rinsed with water, a small amount of methanol, and diethyl ether. The product was dried under vacuum to give a tan solid (2.6 g, 76% yield). The compound was used without further purification.

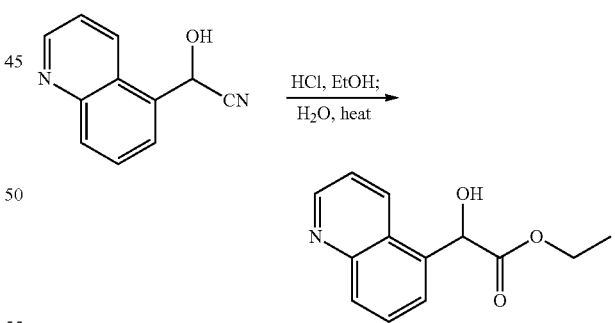

A suspension of 2-hydroxy-2-(quinolin-5-yl)acetonitrile (2.56 g, 13.9 mmol) in absolute ethanol (70 mL) was cooled over an ice bath. HCl was bubbled slowly through the mixture for 1 hour then it was stirred for 15 minutes over ice. The ice bath was removed and water (5 mL) was cautiously added to the reaction. The mixture was heated at 60° C. for 15 minutes, 50° C. for 2 hours, and it was allowed to cool to room temperature. Water was added to the reaction mixture and it was made basic with the slow addition of solid KOH, solid $NaHCO_3$ and saturated aqueous $NaHCO_3$ until the pH=9. The mixture was extracted with EtOAc three times and the combined organics were washed with water and brine, dried over Na₂SO₄ and concentrated in vacuo to give ethyl 2-hydroxy-2-(quinolin-5-yl)acetate as a brown oil (2.39 g, 74% yield).

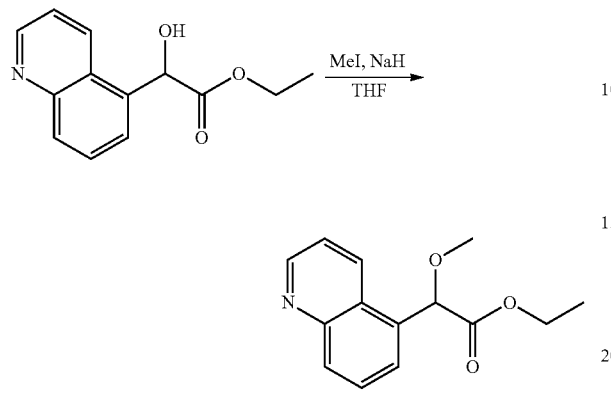

To a solution of ethyl 2-hydroxy-2-(quinolin-5-yl)acetate (1.5 g, 6.5 mmol) in anhydrous THF in an oven-dried flask under argon was added iodomethane (1.2 mL, 19.2 mmol) and the mixture was cooled over an ice bath. NaH (60% in oil; 0.26 g, 6.5 mmol) was added and the mixture stirred for 1 hour over ice. After removing the ice bath, stirring was continued for an additional 3.25 hours, and more NaH (60%; 0.030 g, 0.75 mmol) was added. The mixture was stirred for 45 minutes then the reaction was quenched with brine and further diluted with water. The aqueous mixture was extracted with EtOAc and the combined organics were washed with water three times, brine once, dried over Na₂SO₄ and concentrated in vacuo. Purification by chromatography (50% EtOAc-hexanes) gave ethyl 2-methoxy-2-(quinolin-5-yl)acetate as a yellow oil (0.9 g, 57% yield).

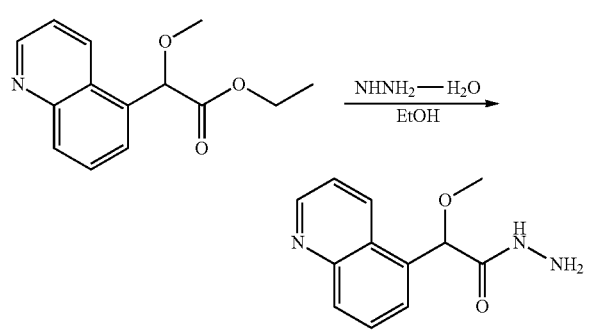

To a solution of ethyl 2-methoxy-2-(quinolin-5-yl)acetate (0.9 g, 3.67 mmol) in absolute ethanol (25 mL) was added hydrazine hydrate (1.0 mL, 20.5 mmol) and the mixture was heated at 85° C. for 18.5 hours. After cooling to room temperature, the mixture was poured into ice-water (~150 mL) then concentrated in vacuo. The residue was taken up in EtOAc, washed with diluted brine once, water twice then brine.

The organics were dried over Na₂SO₄ and concentrated in vacuo to give 2-methoxy-2-(quinolin-5-yl)acetohydrazide as an off-white foam (0.651 g, 77% yield) that was used without further purification.

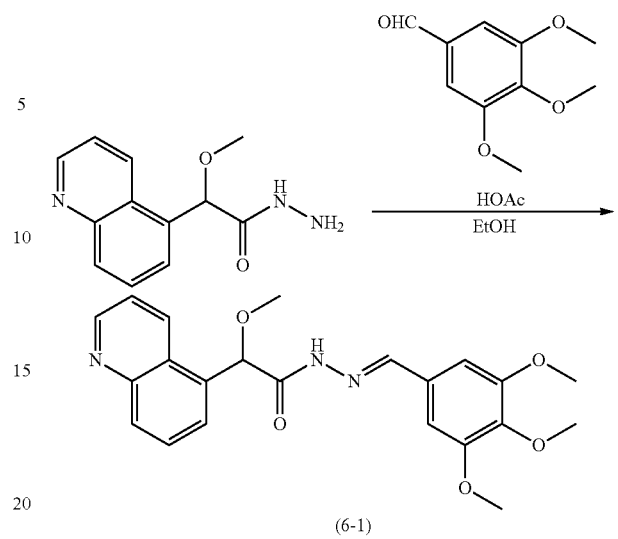

To a mixture of 2-methoxy-2-(quinolin-5-yl)acetohydrazide (0.149 g, 0.65 mmol) and 3,4,5-trimethoxybenzaldehyde (0.138 g, 0.70 mmol) in absolute ethanol (5 mL) was added acetic acid (1 drop). The mixture was heated at 60° C. for 17 hours. After cooling to room temperature, the solid was collected on a Büchner funnel and rinsed with ethanol and diethyl ether then dried in vacuo to give (E)-2-methoxy-2-(quinolin-5-yl)-N'-(3,4,5-trimethoxybenzylidene)acetohydrazide (6-1) as a white powder (0.197 g, 75% yield).

Example 7

Synthesis of (E)-2-(4-(Dimethylamino)phenyl)-2-methoxy-N'-(3,4,5-trimethoxybenzylidene)acetohydrazide

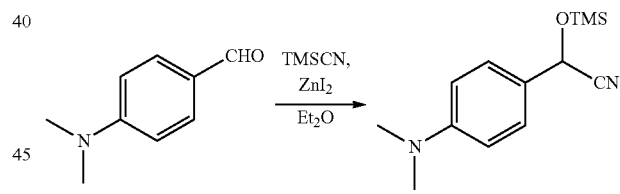

To a suspension of 4-(dimethylamino)benzaldehyde (5.05 g, 33.85 mmol) in diethyl ether (60 mL) in an oven-dried flask under argon was added ZnI₂ (0.325 g, 1.0 mmol). Trimethylsilyl cyanide (5.00 mL, 40.0 mmol) was added slowly and the mixture was stirred at room temperature for 1.75 hours. The solution was diluted with EtOAc and washed with saturated aqueous NaHCO₃, water and brine then dried over Na₂SO₄. After concentration in vacuo, 2-(4-(dimethylamino)phenyl)-2-(trimethylsilyloxy)acetonitrile was obtained as a grey solid (8.3 g, 99% yield).

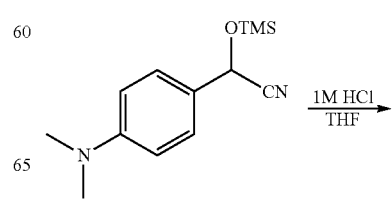

-continued

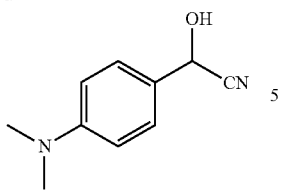

To a solution of 2-(4-(dimethylamino)phenyl)-2-(trimethylsilyloxy)acetonitrile (7.19 g, 28.9 mmol) in THF (35 mL) was added 1 M aqueous HCl (1 mL) and the mixture was stirred for 1 hour. Additional 1 M HCl (1 mL) was then added and the reaction mixture was stirred for an additional 50 minutes. The mixture was made basic with solid NaHCO$_3$ then diluted with EtOAc and water. The layers were separated and the organics were washed with saturated aqueous NaHCO$_3$, water and brine. The solution was dried over Na$_2$SO$_4$ and concentrated in vacuo to give 2-(4-(dimethylamino)phenyl)-2-hydroxyacetonitrile as an off-white solid (5.2 g, quantitative yield). The product was used without further purification.

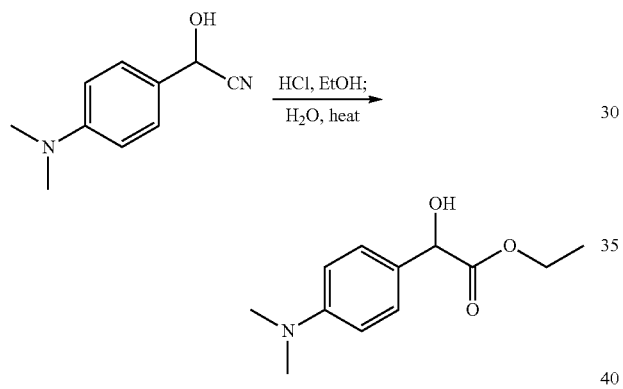

An ice-cold suspension of 2-(4-(dimethylamino)phenyl)-2-hydroxyacetonitrile (5.7 g, 32.3 mmol) in absolute ethanol (60 mL) was bubbled with HCl for 15 minutes. All solids went into solution; the ice bath was removed and the mixture stirred for 15 minutes. Water (5 mL) was added and the mixture was stirred for 40 minutes then heated at 60° C. for 1.5 hours. The mixture was diluted with additional water then made basic with the addition of NaHCO$_3$ until the pH was 9-10. The aqueous mixture was extracted with EtOAc twice and the combined organics were washed with water and brine, dried over Na$_2$SO$_4$, vacuum filtered through Celite and concentrated in vacuo. Purification by chromatography (25-50% EtOAc-hexanes) gave ethyl 2-(4-(dimethylamino)phenyl)-2-hydroxyacetate as a light yellow solid (2.32 g, 32% yield).

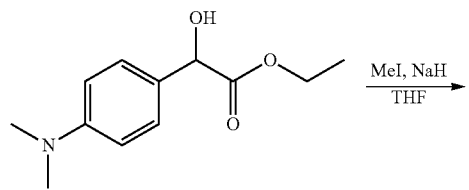

-continued

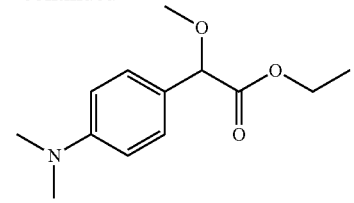

Ethyl 2-(4-(dimethylamino)phenyl)-2-methoxyacetate was synthesized from ethyl 2-(4-(dimethylamino)phenyl)-2-hydroxyacetate according to the method used for the preparation of Example 6. The product, isolated after extractive workup, was an orange oil (0.675 g, 65% yield) and was used without further purification.

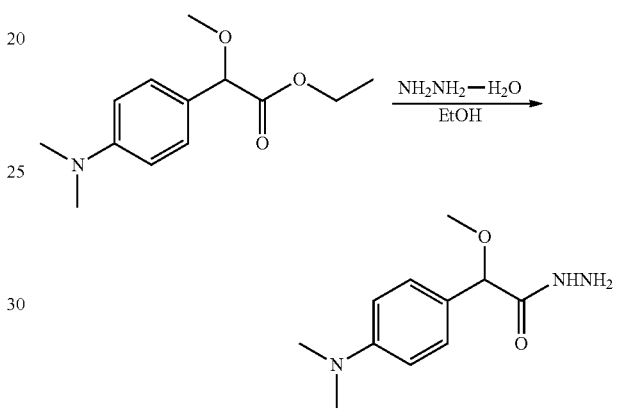

To a solution of ethyl 2-(4-(dimethylamino)phenyl)-2-methoxyacetate (0.675 g, 2.84 mmol) in absolute ethanol (20 mL) was added hydrazine hydrate (0.8 mL, 16.4 mmol) and the mixture was heated at reflux for 22 hours. Additional hydrazine hydrate (1.0 mL, 20.6 mmol) was added and the heating continued for 7 hours. After cooling to room temperature, the mixture was concentrated in vacuo. The residue was dissolved in EtOAc and washed with water and brine, dried over Na$_2$SO$_4$ and concentrated in vacuo. The solid product was stirred with hot diethyl ether then hexanes were added. After cooling to room temperature, the solids were collected on a Büchner funnel and rinsed with 50% diethyl ether-hexanes then dried under vacuum to give 2-(4-(dimethylamino)phenyl)-2-methoxyacetohydrazide as an orange solid (0.246 g). Additional product was isolated from the mother liquor by chromatography (80-100% EtOAc-hexanes, then 5% methanol-EtOAc) to give an off-white solid (0.173 g, 66% yield total).

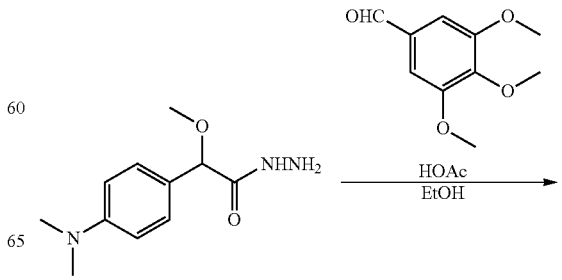

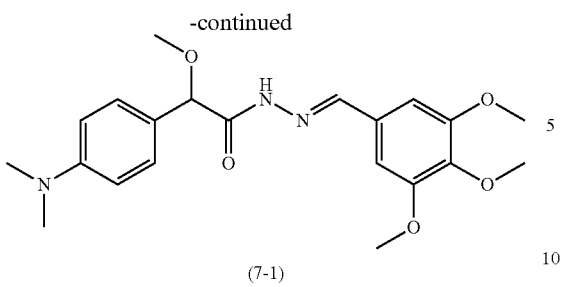

(7-1)

(E)-2-(4-(Dimethylamino)phenyl)-2-methoxy-N'-(3,4,5-trimethoxy benzylidene)acetohydrazide was synthesized from 2-(4-(dimethylamino)phenyl)-2-methoxyacetohydrazide according to the method used for the preparation of Example 6. The product (7-1) was obtained as a white solid (0.0626 g, 34% yield).

Example 8

Synthesis of (E)-2-(Benzo[b]thiophen-2-yl)-2-methoxy-N'-(3,4,5-trimethoxybenzylidene)acetohydrazide

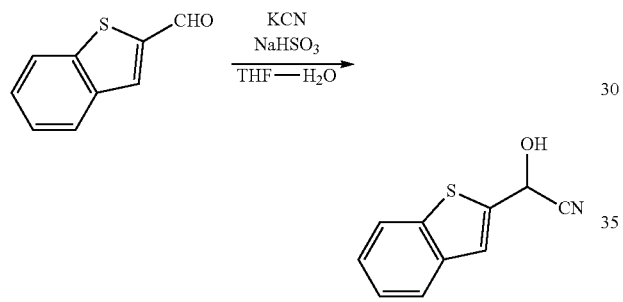

To a solution of benzo[b]thiophene-2-carbaldehyde (2.19 g, 13.5 mmol) in anhydrous THF (200 mL) was added a solution of NaHSO₃ (6.18 g, 59.4 mmol) in water (50 mL). KCN (3.248 g, 49.9 mmol) was added and the mixture was stirred at room temperature for 22 hours. The reaction mixture was then heated at 45° C. for 1 hour. After cooling to room temperature, the mixture was diluted with water and brine and extracted with EtOAc three times. The combined organics were washed with brine, dried over Na₂SO₄ and concentrated in vacuo. Purification by chromatography (0-25% EtOAc-hexanes) gave 2-(benzo[b]thiophen-2-yl)-2-hydroxyacetonitrile as an off-white solid (1.09 g, 46% yield).

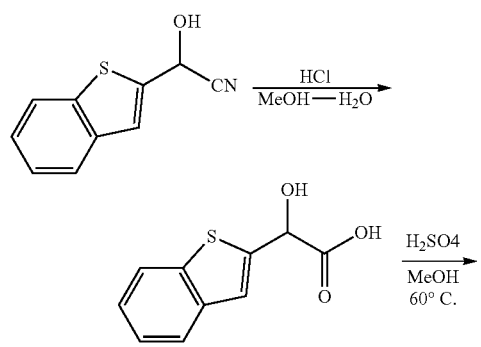

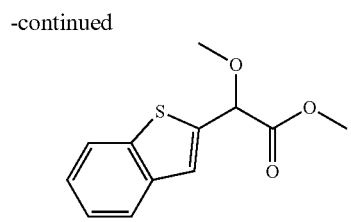

A mixture of 2-(benzo[b]thiophen-2-yl)-2-hydroxyacetonitrile (5.76 mmol) in 3 M aqueous HCl (20 mL) and methanol (8 mL) was heated at 60° C. for 10 minutes then at 80° C. for 20 hours. Concentrated HCl (10 mL) was then added and heating was continued for 5 hours. After cooling to room temperature, the volatiles were removed in vacuo. The residue was extracted with EtOAc and the combined organics were washed with water and brine, dried over Na₂SO₄ and concentrated in vacuo to give 2-(benzo[b]thiophen-2-yl)-2-hydroxyacetic acid as a brown oil (1.20 g) which was used with further purification.

To a solution of 2-(benzo[b]thiophen-2-yl)-2-hydroxyacetic acid (1.20 g, approx. 5.76 mmol) in anhydrous methanol (10 mL) was added concentrated H₂SO₄ (0.25 mL). The mixture was heated at 60° C. for 19 hours. The heat was increased to 70° C. and stirred for 3.5 hours. After cooling to room temperature, the mixture was diluted with water and extracted with EtOAc. The combined organics were washed with dilute aqueous NaHCO₃ and brine then dried over Na₂SO₄ and concentrated in vacuo. Purification by chromatography (10-25% EtOAc-hexanes) gave methyl 2-(benzo[b]thiophen-2-yl)-2-methoxyacetate (0.464 g, 35%).

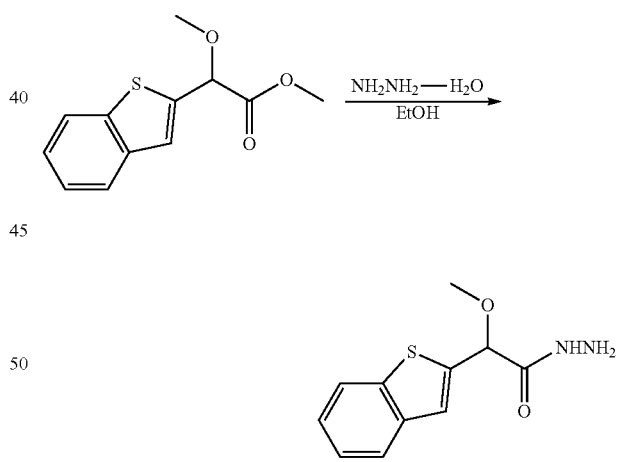

To a solution of methyl 2-(benzo[b]thiophen-2-yl)-2-methoxyacetate (0.174 g, 0.74 mmol) in absolute ethanol (3 mL) was added hydrazine hydrate (0.14 mL, 2.87 mmol) and the mixture was heated at 50° C. for 20 hours. After cooling to room temperature, the solution was concentrated in vacuo. The residue was dissolved in EtOAc and washed with water and brine, dried over Na₂SO₄ and concentrated in vacuo to give 2-(benzo[b]thiophen-2-yl)-2-methoxyacetohydrazide as a colorless oil (0.182 g, quantative yield).

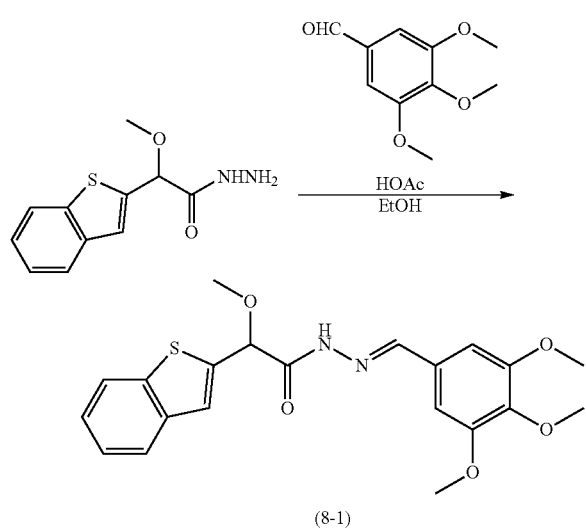

(8-1)

(E)-2-(Benzo[b]thiophen-2-yl)-2-methoxy-N'-(3,4,5-trimethoxy benzylidene)acetohydrazide was synthesized from 2-(4-(dimethylamino)phenyl)-2-methoxyacetohydrazide according to the method used for the preparation of Example 6. The product (8-1) was obtained as a white solid (0.089 g, 60% yield).

Example 9

Synthesis of (E)-N'-(3,4-Dimethoxybenzylidene)-3-methyl-2-phenylbutanehydrazide

Methyl 2-phenylacetate

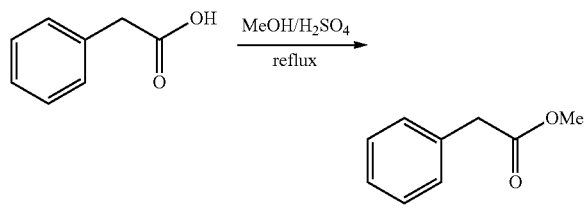

To a stirred solution of 2-methyl-2-phenylacetate (10 g, 1 eq) in dry MeOH was added sulfuric acid (1.0 mL) dropwise and heated to reflux. Stirring was then continued for 2 hours. The reaction mixture was then cooled and poured into saturated aqueous NaHCO₃ and extracted with EtOAc. The combined organic fractions were dried over Na₂SO₄, filtered, and concentrated under reduced pressure to yield an oil (10.5 g, 95%) that was not further purified.

Methyl 3-methyl-2-phenylbutanoate

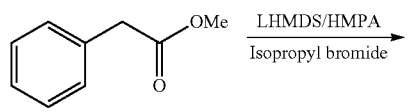

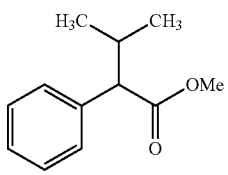

To a stirred solution of methyl 3-methyl-2-phenylbutanoate (0.5 g, 1 eq) in dry THF was added HMPA (1 eq), LiHMDS (1 eq), and 2-bromopropane at −40 to 0° C. for 1 h. The reaction mixture was quenched with water and extracted with EtOAc. The combined organic fractions were dried over Na₂SO₄, filtered, and concentrated under reduced pressure to yield an oil that that was purified by column chromatography using silica gel to provide the product (0.24 g, 34%).

3-Methyl-2-phenylbutanehydrazide

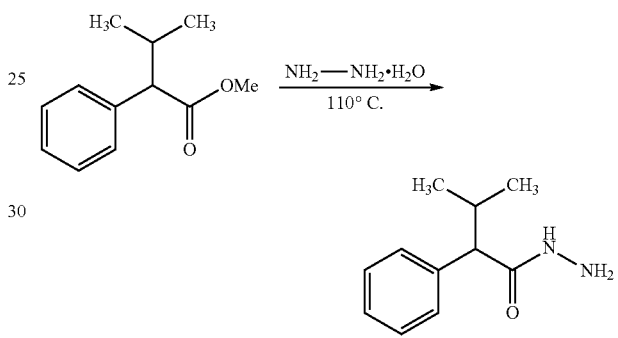

A stirred solution of methyl 3-methyl-2-phenylbutanoate (0.87 g, 1 eq) and hydrazine hydrate (10 mL) was heated at 110° C. for 12 h. The reaction mixture was then cooled and the solvents removed under reduced pressure. The crude oil was diluted with EtOAc and washed with H₂O and the organic phase dried over Na₂SO₄, filtered, and the solvents removed under reduced pressure to yield a yellow oil (0.17 g, 47%) that was purified by column chromatography over silica gel to yield the product (0.61 g).

(E)-N'-(3,4-Dimethoxybenzylidene)-3-methyl-2-phenylbutanehydrazide

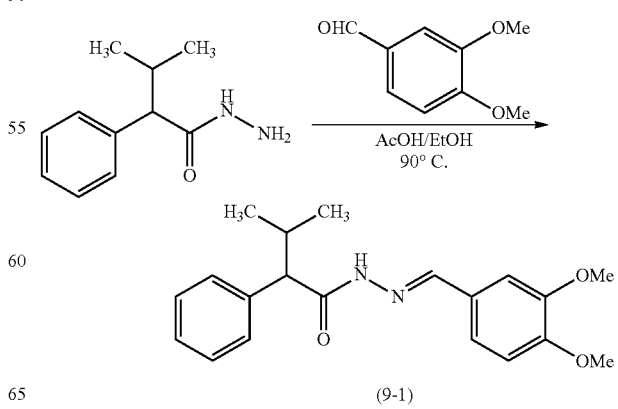

(9-1)

(E)-N'-(3,4-Dimethoxybenzylidene)-3-methyl-2-phenylbutanehydrazide was synthesized from 3-methyl-2-phenylbutanehydrazide according to the method used for the preparation of Example 1. The product (9-1) was purified by column chromatography over silica gel using ethyl acetate/hexanes to provide a solid (0.109 g, 10% yield).

Example 10

Synthesis of (E)-N'-(3,4-Dimethoxybenzylidene)-2-methoxy-N-methyl-2-phenylacetohydrazide

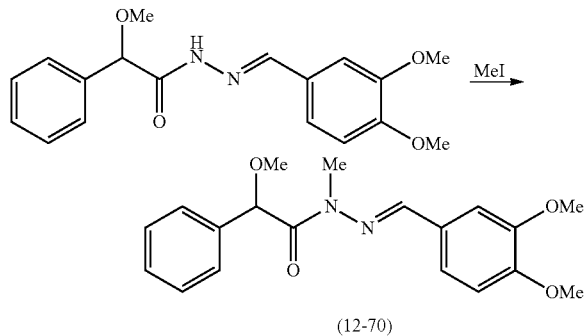

(12-70)

(E)-N'-(3,4-Dimethoxybenzylidene)-2-methoxy-N-methyl-2-phenylacetohydrazide (12-70) was synthesized according to the method used for the preparation of Example 6. To a solution of (E)-N'-(3,4-dimethoxybenzylidene)-2-methoxy-2-phenylacetohydrazide (12-21) (0.56 g) in anhydrous DMF in an oven-dried flask under argon was added iodomethane (1 eq) then NaH (60% in oil; 1.1 eq) was added and the mixture stirred for 2 hours. The reaction was quenched with brine and further diluted with water. The aqueous mixture was extracted with EtOAc and the combined organics were washed with water three times, brine once, dried over Na$_2$SO$_4$ and concentrated in vacuo. Purification by chromatography provided the product (12-70) (0.4 g, 70%).

Example 11

Synthesis of (E)-2-(4-(1H-pyrazol-1-yl)phenyl)-N'-(4-bromo-3,5-dimethoxybenzylidene)-2-methoxy-N-(2,2,2-trifluoroethyl)acetohydrazide

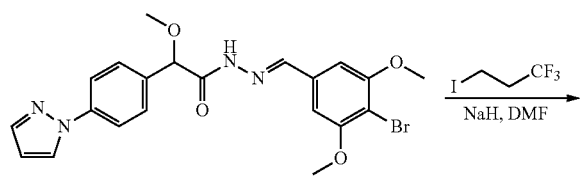

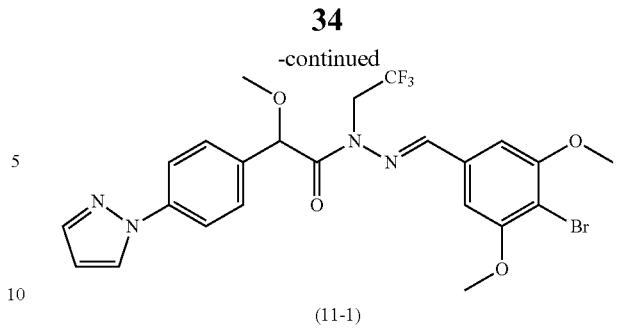

(11-1)

To a solution of (E)-2-(4-(H-pyrazol-1-yl)phenyl)-N'-(4-bromo-3,5-dimethoxybenzylidene)-2-methoxyacetohydrazide (0.167 g, 0.35 mmol) in anhydrous DMF (3.0 mL) was added a 60% dispersion of NaH in mineral oil (0.017 g, 0.43 mmol) under argon and stirred for 10 min. 1,1,1-trifluoro-3-iodopropane (0.042 mL, 0.43 mmol) was added and the mixture was stirred at room temperature for 24 hours then heated to 100° C. for 10 days and then additional 1,1,1-trifluoro-3-iodopropane (0.042 mL, 0.43 mmol) added and the reaction heated to 150° C. for 1 hour. After cooling to room temperature, the mixture was diluted with water and brine and extracted with EtOAc times. The combined organics were washed with brine, dried over Na$_2$SO$_4$ and concentrated in vacuo. Purification by chromatography (20-50% EtOAc-hexanes) gave of product (11-1) as a light yellow solid (0.0543 g, 28% yield).

Example 12

Synthesis of Further Representative Compounds

The following representative compounds in Table 1 were synthesized according to (i) the foregoing procedures by selecting appropriate starting materials (for example, 4-fluoro mandelic acid derivatives (e.g., examples 12-1 and 12-3) were synthesized using commercially available 4-fluoromandelic acid) and (ii) known organic synthesis techniques (for example, treatment of commercially available α-phenylacetic acid methyl ester with hydrazine hydrate in ethanol under with heating provides phenyl-acetic acid hydrazide (see, e.g., Pandeye, S. N.; Manjula, H.; Stables, J. P.; Pharmazie; 2001, 56, 121-124) and treatment of phenyl acetic acid hydrazide with a substituted benzaldehyde in ethanol with heating and in the presence of catalytic acetic acid provides the corresponding substituted phenyl-acetic acid benzylidenehydrazide (see, e.g., Stephanidou-Stephanatou, J.; Lefkopoulou, S; Journal of Heterocyclic Chemistry; 1982; 19; 705-711.0)).

TABLE 1

| Example No. | Structure | MW |
|---|---|---|
| 1-1 | 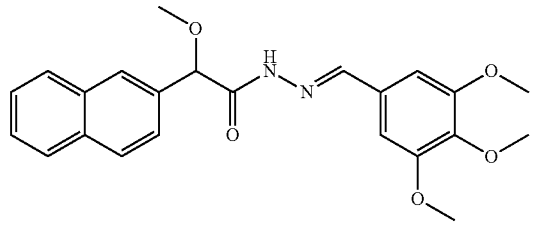 [SMILES: COc1cc(/C=N/NC(=O)C(OC)c2ccc3ccccc3c2)cc(OC)c1OC] | 408.168 |

TABLE 1-continued

| Example No. | Structure | MW |
|---|---|---|
| 2-1 | 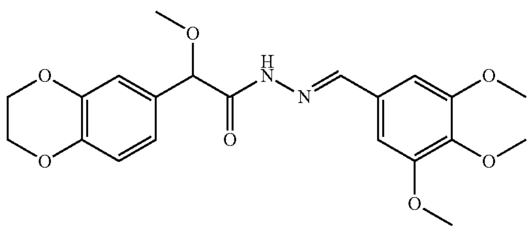 [SMILES: COc1cc(/C=N/NC(=O)C(OC)c2ccc3c(c2)OCCO3)cc(OC)c1OC] | 416.158 |
| 3-1 | 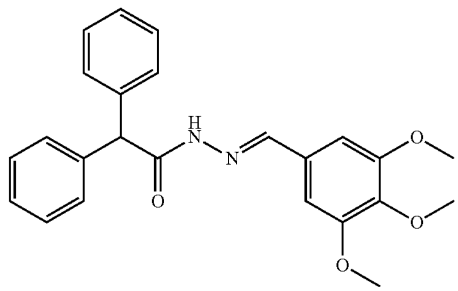 [SMILES: COc1cc(/C=N/NC(=O)C(c2ccccc2)c2ccccc2)cc(OC)c1OC] | 404.174 |
| 4-1 | 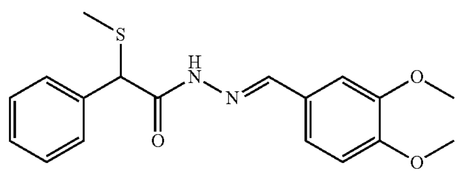 [SMILES: COc1ccc(/C=N/NC(=O)C(SC)c2ccccc2)cc1OC] | 344.433 |
| 5-1 | 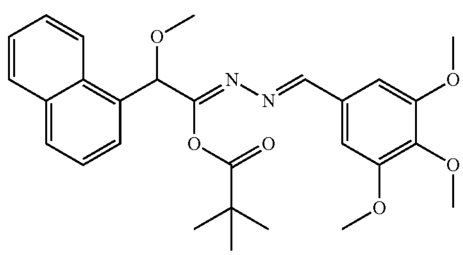 [SMILES: COc1cc(/C=N/N=C(\OC(=O)C(C)(C)C)C(OC)c2cccc3ccccc23)cc(OC)c1OC] | 492.23 |
| 6-1 | 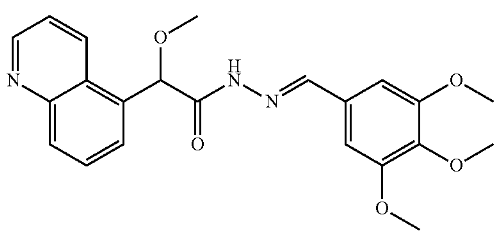 [SMILES: COc1cc(/C=N/NC(=O)C(OC)c2cccc3ncccc23)cc(OC)c1OC] | 409.44 |
| 7-1 | 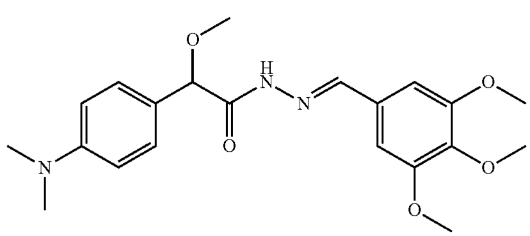 | 401.46 |

TABLE 1-continued

| Example No. | Structure | MW |
|---|---|---|
| 8-1 | 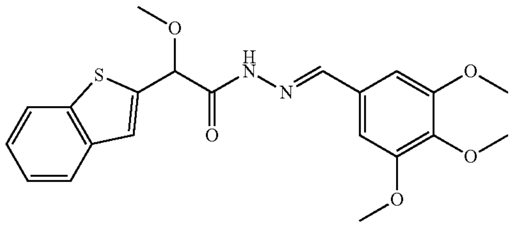 [SMILES: COc1cc(/C=N/NC(=O)C(OC)c2cc3ccccc3s2)cc(OC)c1OC] | 414.12 |
| 9-1 | 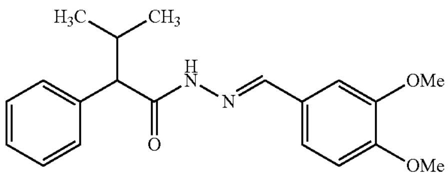 [SMILES: COc1ccc(/C=N/NC(=O)C(c2ccccc2)C(C)C)cc1OC] | 340.42 |
| 11-1 | 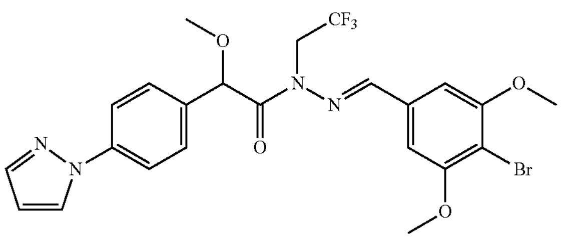 [SMILES: COc1cc(/C=N/N(CC(F)(F)F)C(=O)C(OC)c2ccc(-n3cccn3)cc2)cc(OC)c1Br] | 555.34 |
| 12-1 | 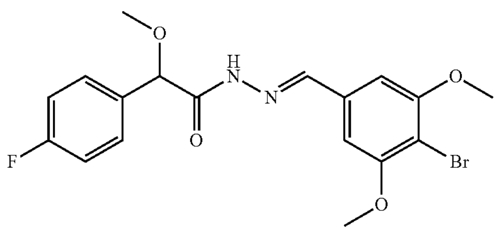 [SMILES: COc1cc(/C=N/NC(=O)C(OC)c2ccc(F)cc2)cc(OC)c1Br] | 424.043 |
| 12-2 | 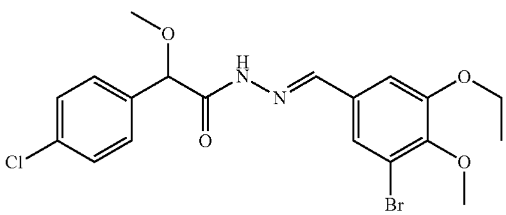 [SMILES: CCOc1cc(/C=N/NC(=O)C(OC)c2ccc(Cl)cc2)cc(Br)c1OC] | 454.029 |
| 12-3 | 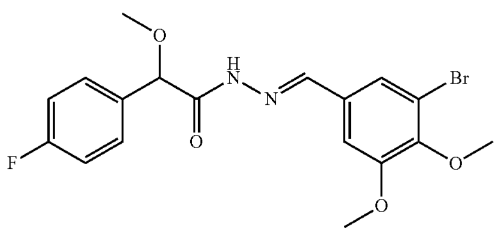 [SMILES: COc1cc(/C=N/NC(=O)C(OC)c2ccc(F)cc2)cc(Br)c1OC] | 424.043 |
| 12-4 | 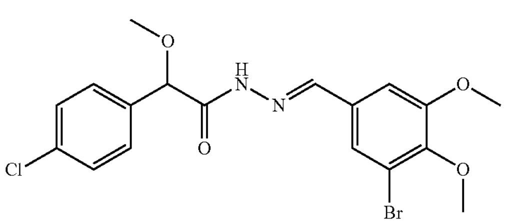 [SMILES: COc1cc(/C=N/NC(=O)C(OC)c2ccc(Cl)cc2)cc(Br)c1OC] | 440.014 |

TABLE 1-continued

| Example No. | Structure | MW |
|---|---|---|
| 12-5 | 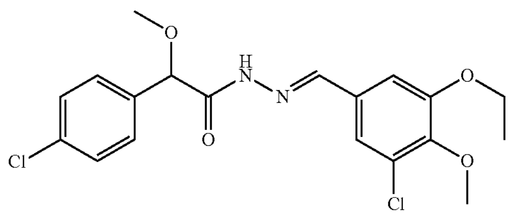 [SMILES: CCOc1cc(/C=N/NC(=O)C(OC)c2ccc(Cl)cc2)cc(Cl)c1OC] | 410.08 |
| 12-6 | 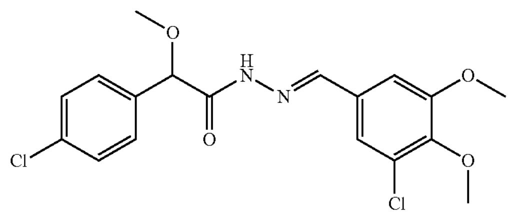 [SMILES: COc1cc(/C=N/NC(=O)C(OC)c2ccc(Cl)cc2)cc(Cl)c1OC] | 396.064 |
| 12-7 | 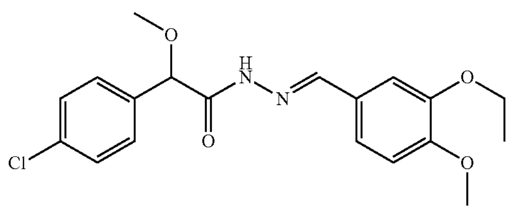 [SMILES: CCOc1cc(/C=N/NC(=O)C(OC)c2ccc(Cl)cc2)ccc1OC] | 376.119 |
| 12-8 | 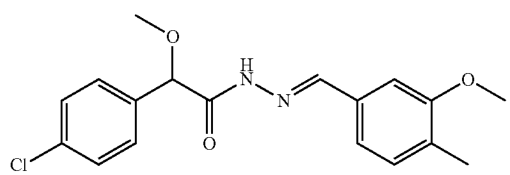 [SMILES: COc1cc(/C=N/NC(=O)C(OC)c2ccc(Cl)cc2)ccc1C] | 346.108 |
| 12-9 | 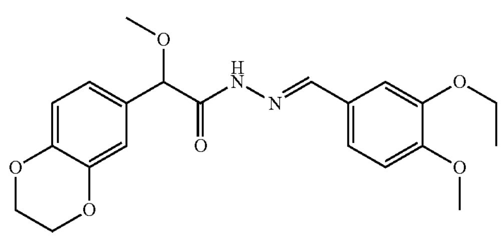 [SMILES: CCOc1cc(/C=N/NC(=O)C(OC)c2ccc3c(c2)OCCO3)ccc1OC] | 400.43 |
| 12-10 | 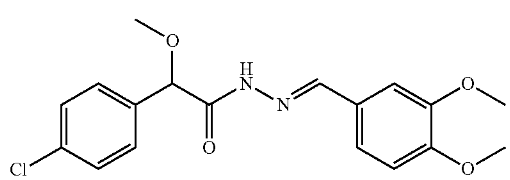 [SMILES: COc1ccc(/C=N/NC(=O)C(OC)c2ccc(Cl)cc2)cc1OC] | 362.103 |
| 12-11 | 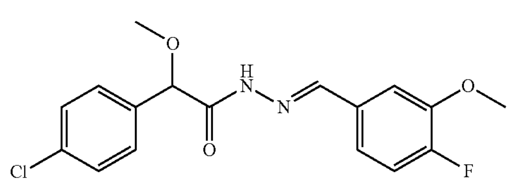 [SMILES: COc1cc(/C=N/NC(=O)C(OC)c2ccc(Cl)cc2)ccc1F] | 350.083 |

TABLE 1-continued

| Example No. | Structure | MW |
|---|---|---|
| 12-12 | 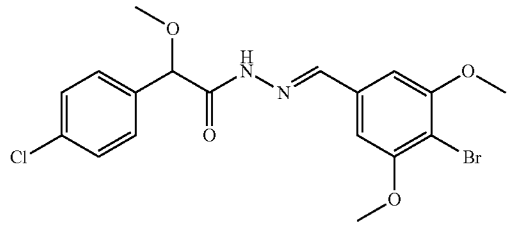 [SMILES: COc1cc(/C=N/NC(=O)C(OC)c2ccc(Cl)cc2)cc(OC)c1Br] | 440.014 |
| 12-13 | 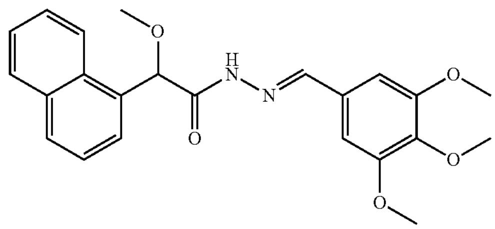 [SMILES: COc1cc(/C=N/NC(=O)C(OC)c2cccc3ccccc23)cc(OC)c1OC] | 408.168 |
| 12-14 | 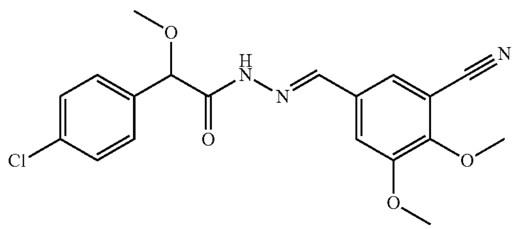 [SMILES: COc1cc(/C=N/NC(=O)C(OC)c2ccc(Cl)cc2)cc(C#N)c1OC] | 387.099 |
| 12-15 | 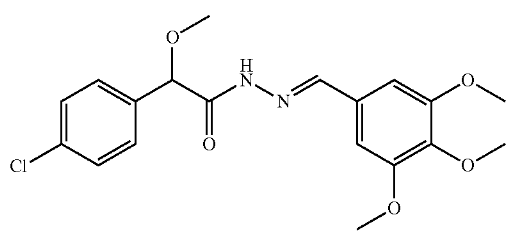 [SMILES: COc1cc(/C=N/NC(=O)C(OC)c2ccc(Cl)cc2)cc(OC)c1OC] | 392.83 |
| 12-16 | 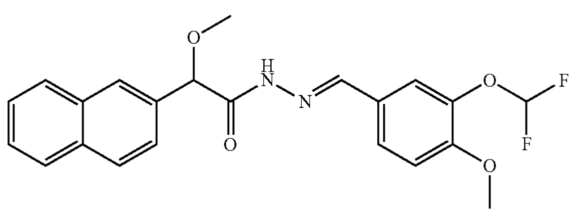 [SMILES: COc1ccc(/C=N/NC(=O)C(OC)c2ccc3ccccc3c2)cc1OC(F)F] | 414.139 |
| 12-17 | 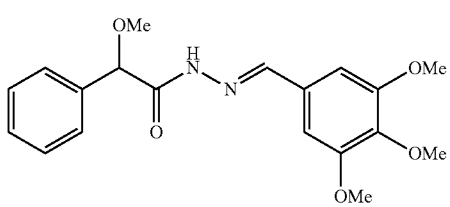 [SMILES: COc1cc(/C=N/NC(=O)C(OC)c2ccccc2)cc(OC)c1OC] | 358.39 |
| 12-18 | 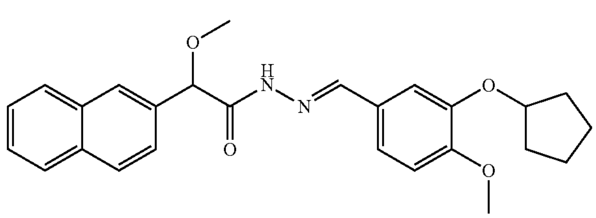 [SMILES: COc1ccc(/C=N/NC(=O)C(OC)c2ccc3ccccc3c2)cc1OC1CCCC1] | 432.205 |

TABLE 1-continued

| Example No. | Structure | MW |
|---|---|---|
| 12-19 | (4-methoxyphenyl)(methoxy)acetyl N'-(3,4-dimethoxybenzylidene)hydrazide | 358.39 |
| 12-20 | 2-methoxy-2-phenyl-N'-(3-methoxy-4-methylbenzylidene)acetohydrazide | 312.37 |
| 12-21 | 2-methoxy-2-phenyl-N'-(3,4-dimethoxybenzylidene)acetohydrazide | 328.368 |
| 12-22 | 2-(4-chlorophenyl)-2-methoxy-N'-(4-cyano-3-methoxybenzylidene)acetohydrazide | 357.088 |
| 12-23 | 2-methoxy-2-(naphthalen-2-yl)-N'-(3,4-dimethoxybenzylidene)acetohydrazide | 378.158 |
| 12-24 | 2-methoxy-2-phenyl-N'-(4-hydroxy-3,5-dimethoxybenzylidene)acetohydrazide | 344.37 |
| 12-25 | 2-methoxy-2-phenyl-N'-(3,5-dimethoxybenzylidene)acetohydrazide | 328.37 |

TABLE 1-continued

| Example No. | Structure | MW |
|---|---|---|
| 12-26 | 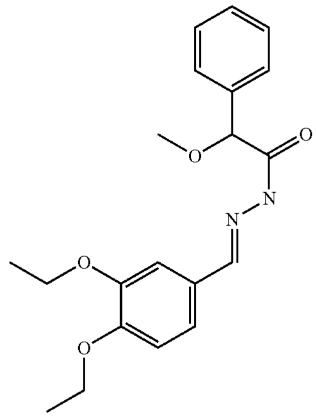 [SMILES: CCOc1ccc(/C=N/NC(=O)C(OC)c2ccccc2)cc1OCC] | 356.42 |
| 12-27 | 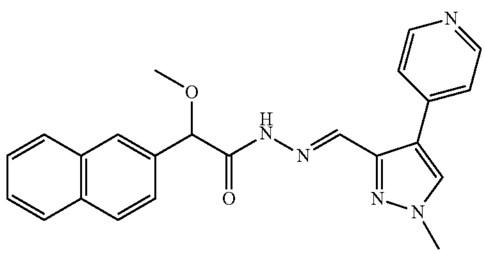 [SMILES: COC(C(=O)N/N=C/c1nn(C)cc1-c1ccncc1)c1ccc2ccccc2c1] | 399.169 |
| 12-28 | 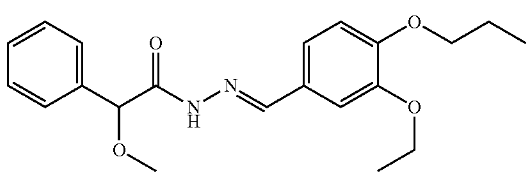 [SMILES: CCCOc1ccc(/C=N/NC(=O)C(OC)c2ccccc2)cc1OCC] | 370.49 |
| 12-29 | 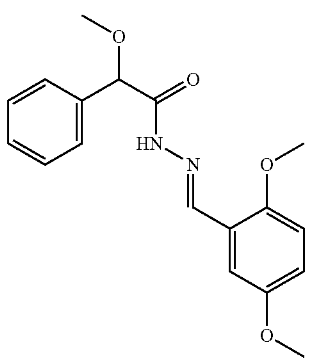 [SMILES: COc1ccc(OC)c(/C=N/NC(=O)C(OC)c2ccccc2)c1] | 328.37 |
| 12-30 | 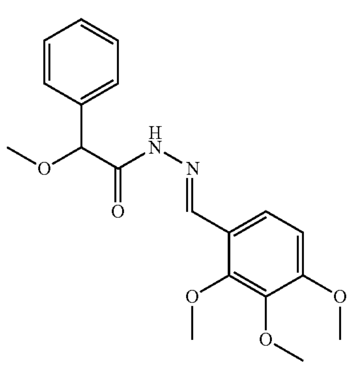 | 358.39 |

TABLE 1-continued
| Example No. | Structure | MW |
|---|---|---|
| 12-31 | 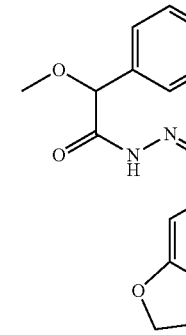 | 391.23 |
| 12-32 | 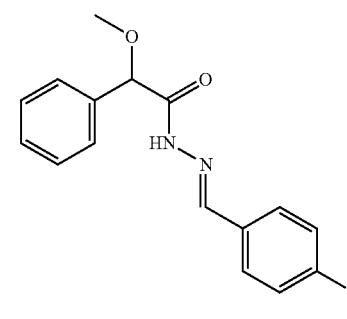 | 298.34 |
| 12-33 | 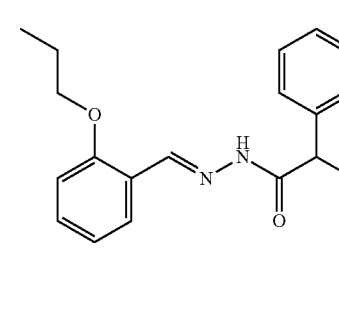 | 326.40 |
| 12-34 | 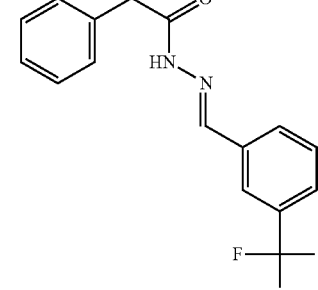 | 336.31 |

TABLE 1-continued

| Example No. | Structure | MW |
|---|---|---|
| 12-35 | 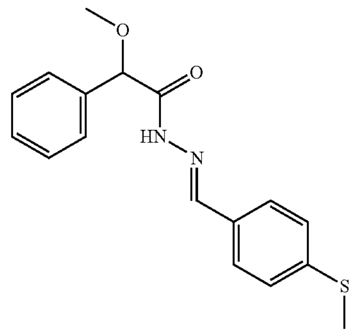 [SMILES: COC(C(=O)N/N=C/c1ccc(SC)cc1)c1ccccc1] | 314.41 |
| 12-36 | 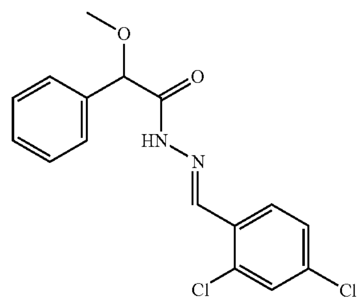 [SMILES: COC(C(=O)N/N=C/c1ccc(Cl)cc1Cl)c1ccccc1] | 337.21 |
| 12-37 | 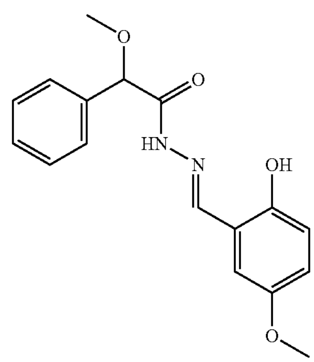 [SMILES: COc1ccc(O)c(/C=N/NC(=O)C(OC)c2ccccc2)c1] | 314.34 |
| 12-38 | 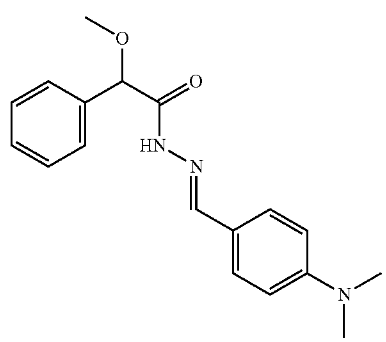 [SMILES: COC(C(=O)N/N=C/c1ccc(N(C)C)cc1)c1ccccc1] | 311.38 |

TABLE 1-continued

| Example No. | Structure | MW |
|---|---|---|
| 12-39 | 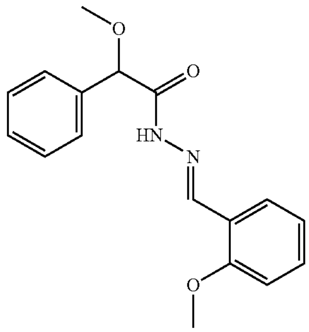 [SMILES: COc1ccccc1/C=N/NC(=O)C(OC)c1ccccc1] | 298.34 |
| 12-40 | 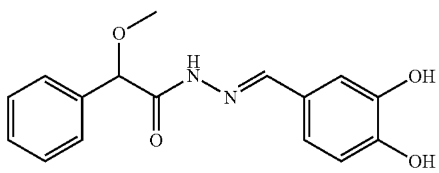 [SMILES: COC(C(=O)N/N=C/c1ccc(O)c(O)c1)c1ccccc1] | 300.31 |
| 12-41 | 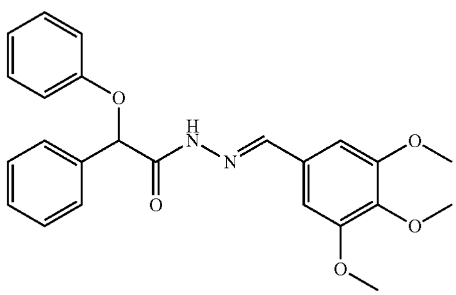 [SMILES: COc1cc(/C=N/NC(=O)C(Oc2ccccc2)c2ccccc2)cc(OC)c1OC] | 420.46 |
| 12-42 | 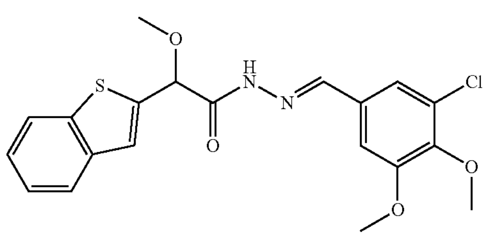 [SMILES: COc1cc(/C=N/NC(=O)C(OC)c2cc3ccccc3s2)cc(Cl)c1OC] | 418.08 |
| 12-43 | 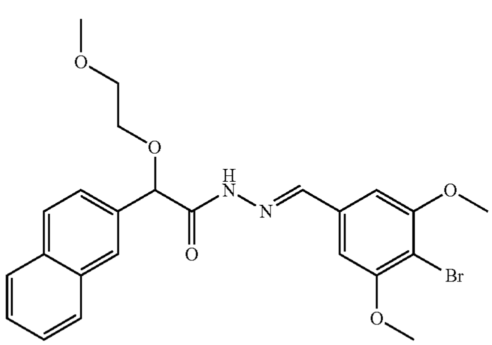 [SMILES: COCCOC(C(=O)N/N=C/c1cc(OC)c(Br)c(OC)c1)c1ccc2ccccc2c1] | 500.095 |

TABLE 1-continued

| Example No. | Structure | MW |
|---|---|---|
| 12-44 | 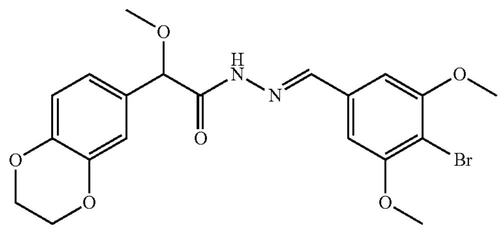 [SMILES: COc1cc(/C=N/NC(=O)C(OC)c2ccc3c(c2)OCCO3)cc(OC)c1Br] | 464.058 |
| 12-45 | 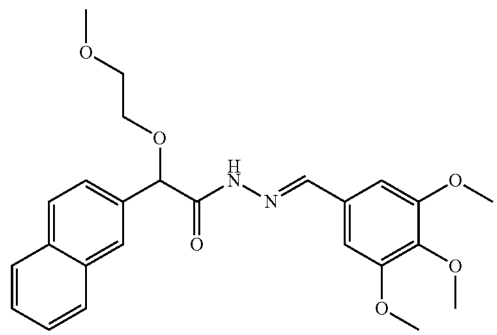 [SMILES: COCCOC(C(=O)N/N=C/c1cc(OC)c(OC)c(OC)c1)c1ccc2ccccc2c1] | 452.195 |
| 12-46 | 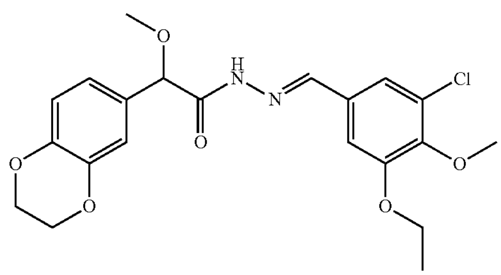 [SMILES: CCOc1cc(/C=N/NC(=O)C(OC)c2ccc3c(c2)OCCO3)cc(Cl)c1OC] | 434.124 |
| 12-47 | 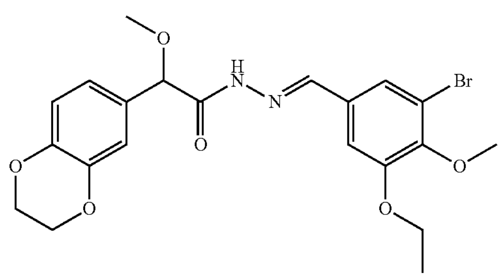 [SMILES: CCOc1cc(/C=N/NC(=O)C(OC)c2ccc3c(c2)OCCO3)cc(Br)c1OC] | 478.074 |
| 12-48 | 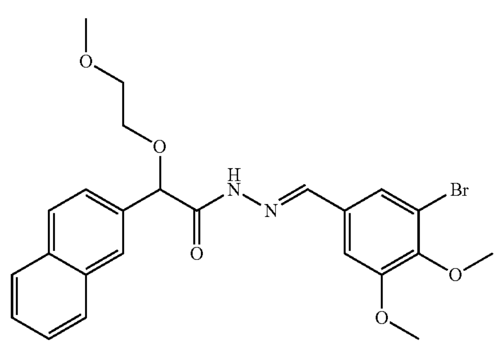 [SMILES: COCCOC(C(=O)N/N=C/c1cc(Br)c(OC)c(OC)c1)c1ccc2ccccc2c1] | 500.095 |

TABLE 1-continued

| Example No. | Structure | MW |
|---|---|---|
| 12-49 | 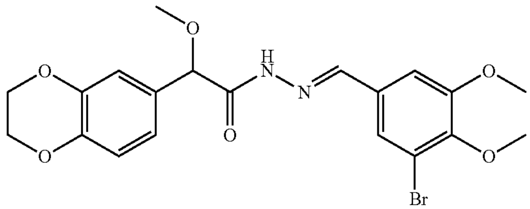 [SMILES: COc1cc(/C=N/NC(=O)C(OC)c2ccc3c(c2)OCCO3)cc(Cl)c1OC] | 464.058 |
| 12-50 | 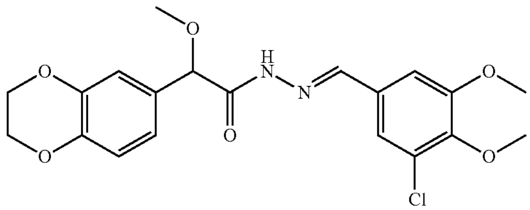 | 420.109 |
| 12-51 | 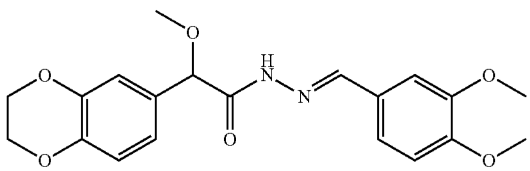 [SMILES: COc1ccc(/C=N/NC(=O)C(OC)c2ccc3c(c2)OCCO3)cc1OC] | 386.148 |
| 12-52 | 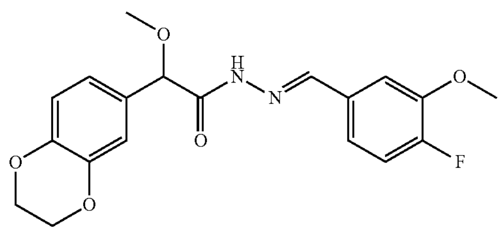 [SMILES: COc1cc(/C=N/NC(=O)C(OC)c2ccc3c(c2)OCCO3)ccc1F] | 374.128 |
| 12-53 | 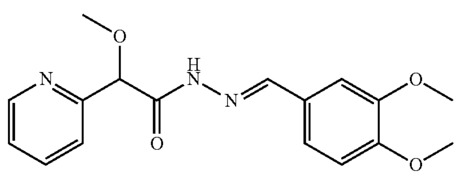 [SMILES: COc1ccc(/C=N/NC(=O)C(OC)c2ccccn2)cc1OC] | 329.36 |
| 12-54 | 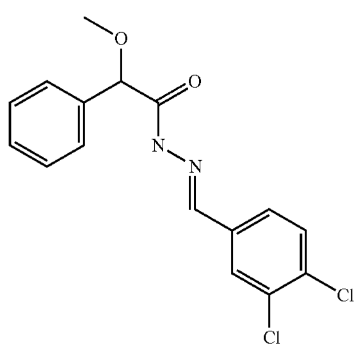 [SMILES: COC(C(=O)N/N=C/c1ccc(Cl)c(Cl)c1)c1ccccc1] | 337.21 |
| 12-55 | 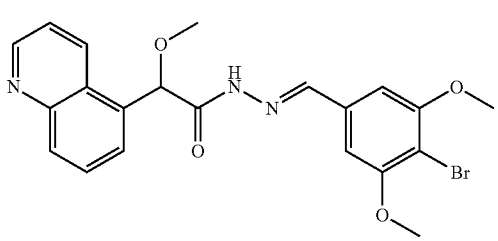 [SMILES: COc1cc(/C=N/NC(=O)C(OC)c2cccc3ncccc23)cc(OC)c1Br] | 458.31 |

TABLE 1-continued

| Example No. | Structure | MW |
|---|---|---|
| 12-56 | 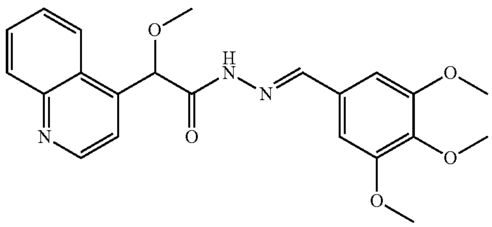 [SMILES: COc1cc(/C=N/NC(=O)C(OC)c2ccnc3ccccc23)cc(OC)c1OC] | 409.44 |
| 12-57 | 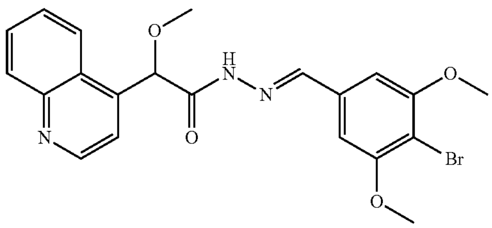 [SMILES: COc1cc(/C=N/NC(=O)C(OC)c2ccnc3ccccc23)cc(OC)c1Br] | 458.31 |
| 12-58 | 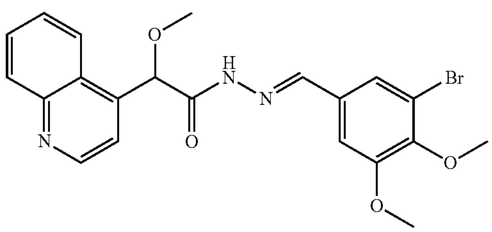 [SMILES: COc1cc(/C=N/NC(=O)C(OC)c2ccnc3ccccc23)cc(Br)c1OC] | 458.31 |
| 12-59 | 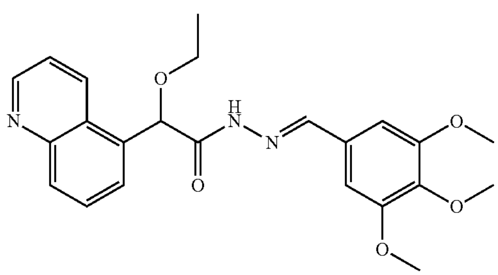 [SMILES: CCOC(C(=O)N/N=C/c1cc(OC)c(OC)c(OC)c1)c1cccc2ncccc12] | 423.46 |
| 12-60 | 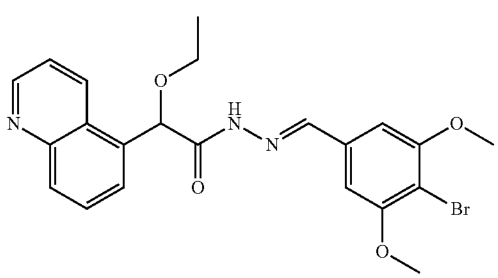 [SMILES: CCOC(C(=O)N/N=C/c1cc(OC)c(Br)c(OC)c1)c1cccc2ncccc12] | 472.33 |
| 12-61 | 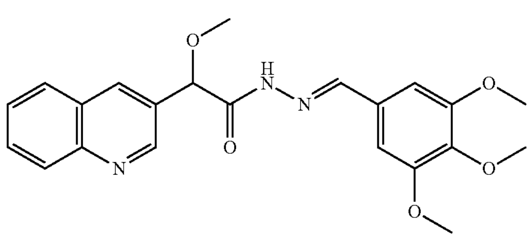 [SMILES: COc1cc(/C=N/NC(=O)C(OC)c2cnc3ccccc3c2)cc(OC)c1OC] | 409.44 |

TABLE 1-continued

| Example No. | Structure | MW |
|---|---|---|
| 12-62 | 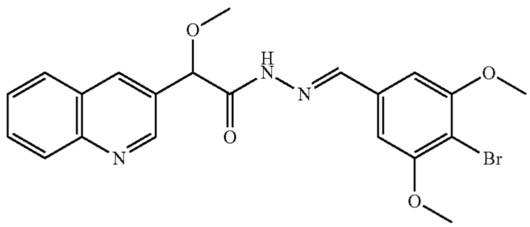 [SMILES: COc1cc(/C=N/NC(=O)C(OC)c2cnc3ccccc3c2)cc(OC)c1Br] | 458.31 |
| 12-63 | 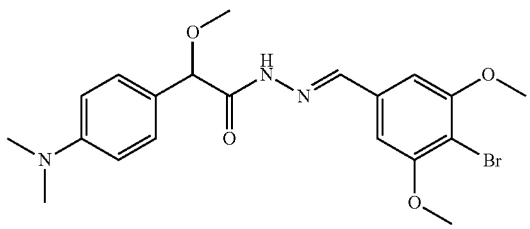 | 449.095 |
| 12-64 | 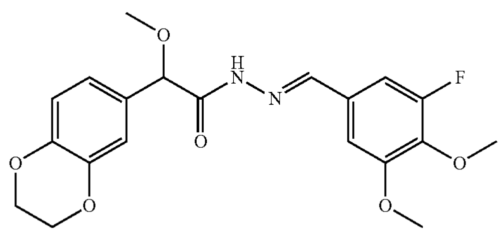 [SMILES: COc1cc(/C=N/NC(=O)C(OC)c2ccc3c(c2)OCCO3)cc(F)c1OC] | 404.14 |
| 12-65 | 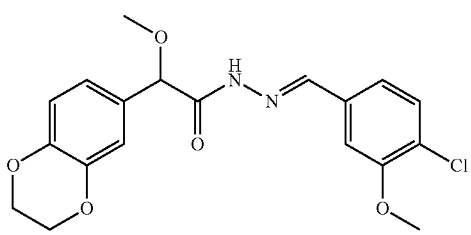 [SMILES: COc1cc(/C=N/NC(=O)C(OC)c2ccc3c(c2)OCCO3)ccc1Cl] | 390.1 |
| 12-66 | 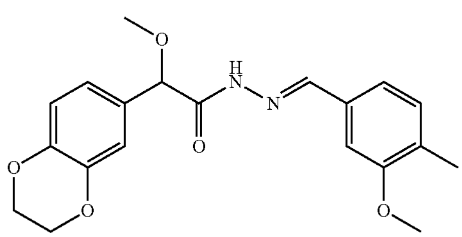 [SMILES: COc1cc(/C=N/NC(=O)C(OC)c2ccc3c(c2)OCCO3)ccc1C] | 370.15 |
| 12-67 | 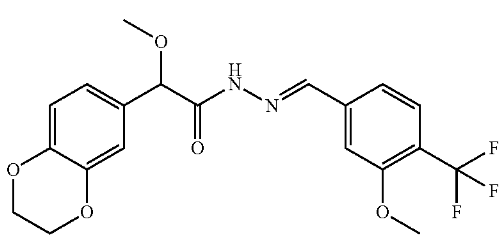 [SMILES: COc1cc(/C=N/NC(=O)C(OC)c2ccc3c(c2)OCCO3)ccc1C(F)(F)F] | 424.12 |

TABLE 1-continued

| Example No. | Structure | MW |
|---|---|---|
| 12-68 | 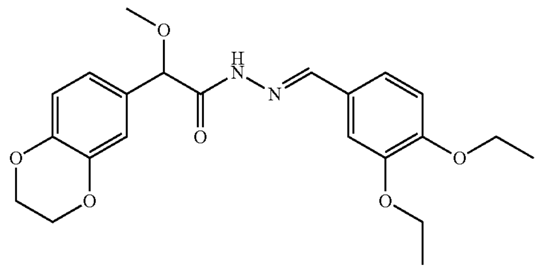 [SMILES: CCOc1ccc(/C=N/NC(=O)C(OC)c2ccc3c(c2)OCCO3)cc1OCC] | 414.45 |
| 12-69 | 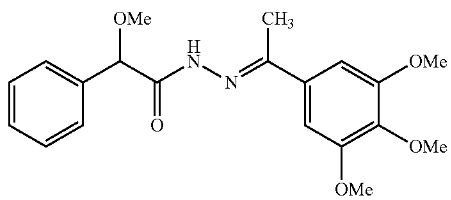 [SMILES: COc1cc(/C(C)=N/NC(=O)C(OC)c2ccccc2)cc(OC)c1OC] | 372.42 |
| 12-70 | 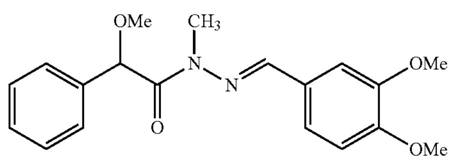 [SMILES: COc1ccc(/C=N/N(C)C(=O)C(OC)c2ccccc2)cc1OC] | 342.39 |
| 12-71 | 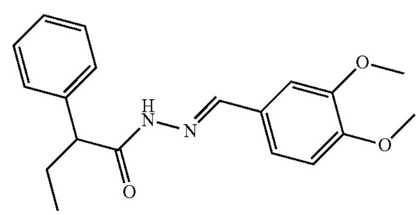 [SMILES: CCC(C(=O)N/N=C/c1ccc(OC)c(OC)c1)c1ccccc1] | 326.40 |
| 12-72 | 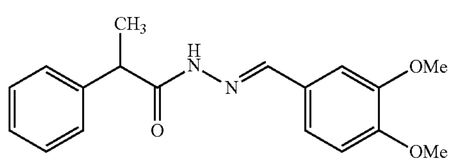 [SMILES: COc1ccc(/C=N/NC(=O)C(C)c2ccccc2)cc1OC] | 312.37 |
| 12-73 | 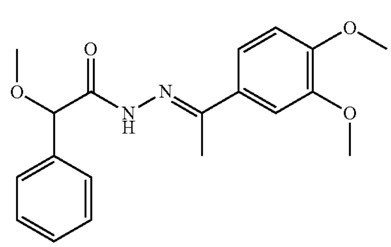 [SMILES: COc1ccc(/C(C)=N/NC(=O)C(OC)c2ccccc2)cc1OC] | 342.39 |
| 12-74 | 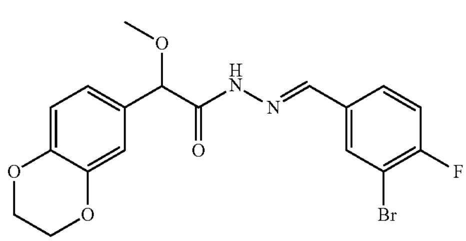 [SMILES: COC(C(=O)N/N=C/c1ccc(F)c(Br)c1)c1ccc2c(c1)OCCO2] | 423.23 |

TABLE 1-continued

| Example No. | Structure | MW |
|---|---|---|
| 12-75 | 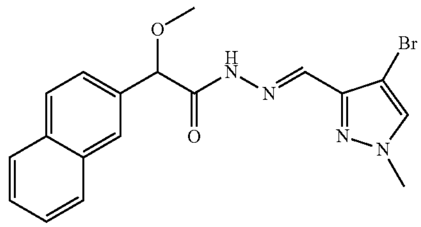 [SMILES: COC(C(=O)N/N=C/c1nn(C)cc1Br)c1ccc2ccccc2c1] | 401.26 |
| 12-76 | 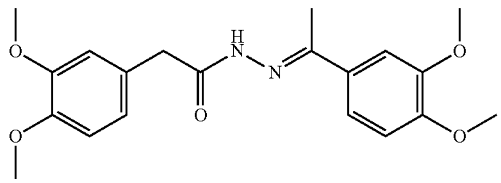 [SMILES: COc1ccc(CC(=O)N/N=C(\C)c2ccc(OC)c(OC)c2)cc1OC] | 372.42 |
| 12-77 | 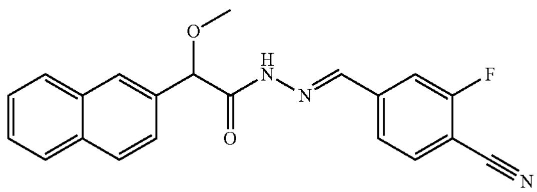 [SMILES: COC(C(=O)N/N=C/c1ccc(C#N)c(F)c1)c1ccc2ccccc2c1] | 361.12 |
| 12-78 | 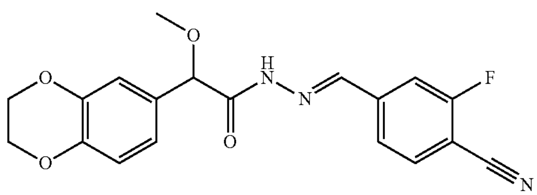 [SMILES: COC(C(=O)N/N=C/c1ccc(C#N)c(F)c1)c1ccc2c(c1)OCCO2] | 369.35 |
| 12-79 | 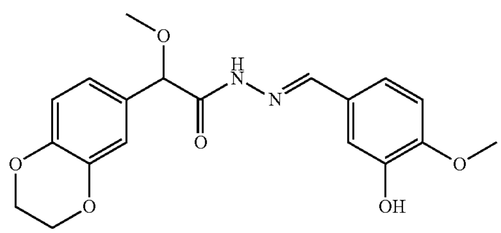 [SMILES: COc1ccc(/C=N/NC(=O)C(OC)c2ccc3c(c2)OCCO3)cc1O] | 372.37 |
| 12-80 | 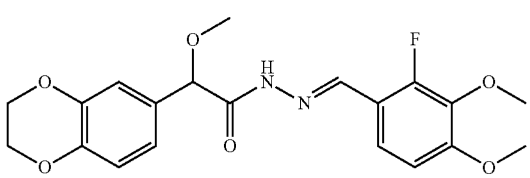 [SMILES: COc1ccc(/C=N/NC(=O)C(OC)c2ccc3c(c2)OCCO3)c(F)c1OC] | 404.39 |
| 12-81 | 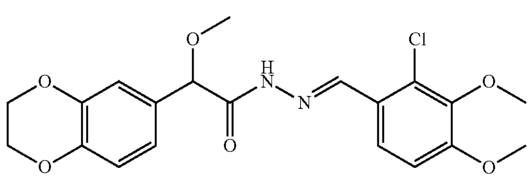 [SMILES: COc1ccc(/C=N/NC(=O)C(OC)c2ccc3c(c2)OCCO3)c(Cl)c1OC] | 420.84 |
| 12-82 | 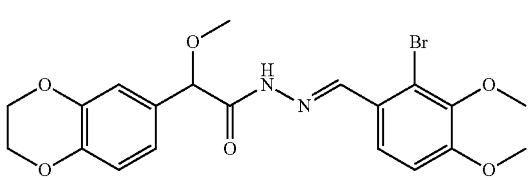 | 465.29 |

TABLE 1-continued

| Example No. | Structure | MW |
|---|---|---|
| 12-83 | 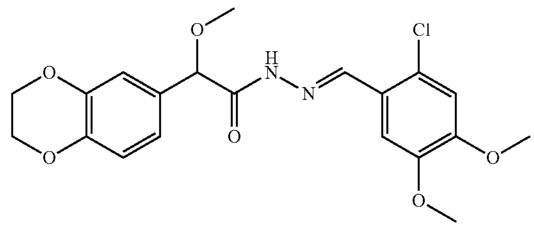 [SMILES: COc1cc(Cl)c(/C=N/NC(=O)C(OC)c2ccc3c(c2)OCCO3)cc1OC] | 420.84 |
| 12-84 | 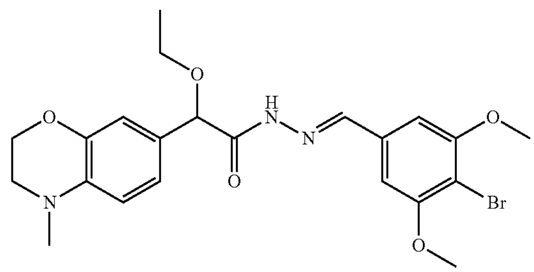 [SMILES: CCOC(C(=O)N/N=C/c1cc(OC)c(Br)c(OC)c1)c1ccc2c(c1)OCCN2C] | 492.36 |
| 12-85 | 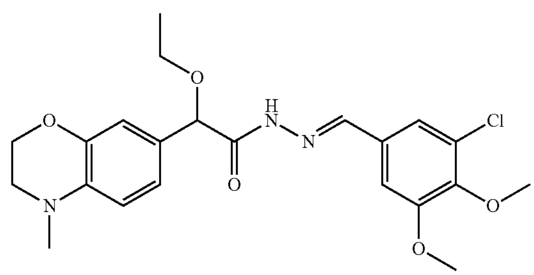 [SMILES: CCOC(C(=O)N/N=C/c1cc(Cl)c(OC)c(OC)c1)c1ccc2c(c1)OCCN2C] | 447.91 |
| 12-86 | 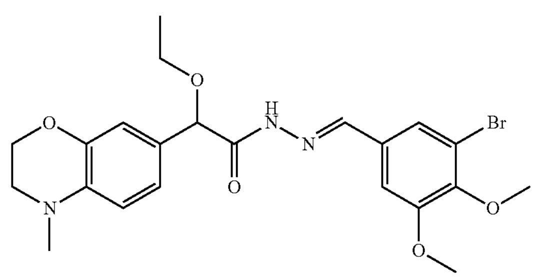 [SMILES: CCOC(C(=O)N/N=C/c1cc(Br)c(OC)c(OC)c1)c1ccc2c(c1)OCCN2C] | 492.36 |
| 12-87 | 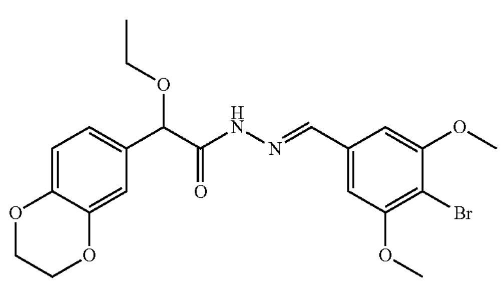 [SMILES: CCOC(C(=O)N/N=C/c1cc(OC)c(Br)c(OC)c1)c1ccc2c(c1)OCCO2] | 479.32 |

TABLE 1-continued
| Example No. | Structure | MW |
|---|---|---|
| 12-88 | 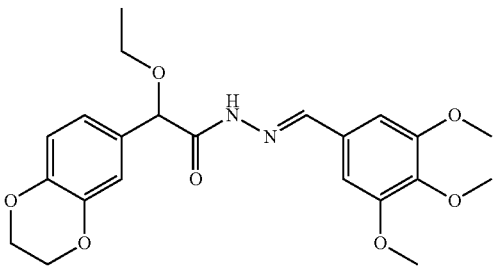 [SMILES: CCOC(C(=O)N/N=C/c1cc(OC)c(OC)c(OC)c1)c1ccc2c(c1)OCCO2] | 430.45 |
| 12-89 | 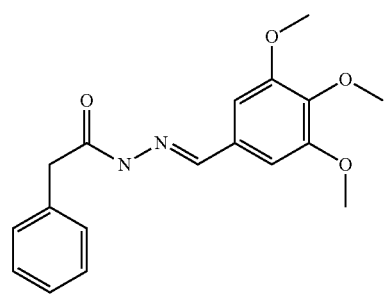 [SMILES: COc1cc(/C=N/NC(=O)Cc2ccccc2)cc(OC)c1OC] | 327.35 |
| 12-90 | 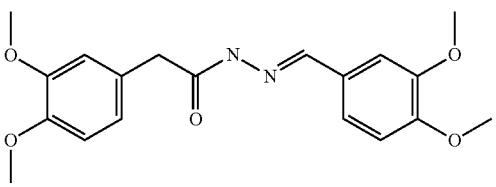 [SMILES: COc1ccc(/C=N/NC(=O)Cc2ccc(OC)c(OC)c2)cc1OC] | 358.39 |
| 12-91 | 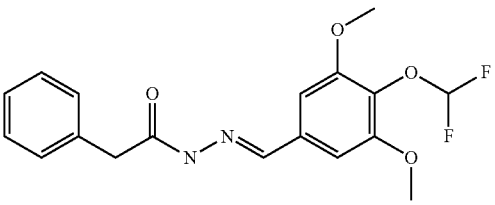 [SMILES: COc1cc(/C=N/NC(=O)Cc2ccccc2)cc(OC)c1OC(F)F] | 363.34 |
| 12-92 | 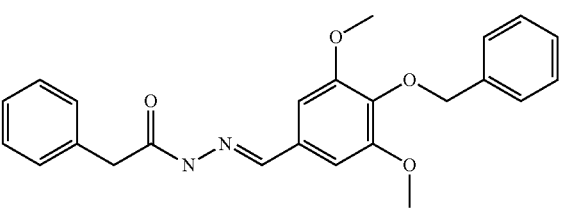 [SMILES: COc1cc(/C=N/NC(=O)Cc2ccccc2)cc(OC)c1OCc1ccccc1] | 403.45 |
| 12-93 | 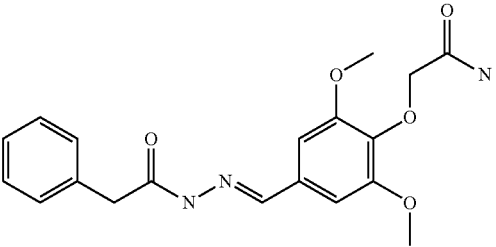 [SMILES: COc1cc(/C=N/NC(=O)Cc2ccccc2)cc(OC)c1OCC(N)=O] | 368.36 |

TABLE 1-continued
| Example No. | Structure | MW |
|---|---|---|
| 12-94 | 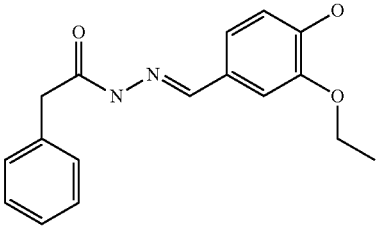 [SMILES: CCOc1cc(/C=N/NC(=O)Cc2ccccc2)ccc1O] | 296.32 |
| 12-95 | 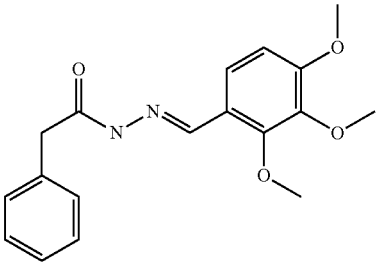 [SMILES: COc1ccc(/C=N/NC(=O)Cc2ccccc2)c(OC)c1OC] | 327.35 |
| 12-96 | 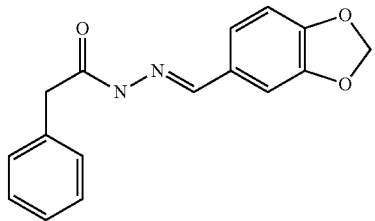 [SMILES: O=C(Cc1ccccc1)N/N=C/c1ccc2c(c1)OCO2] | 281.29 |
| 12-97 | 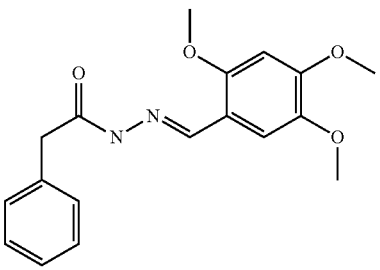 [SMILES: COc1cc(OC)c(OC)cc1/C=N/NC(=O)Cc1ccccc1] | 327.35 |
| 12-98 | 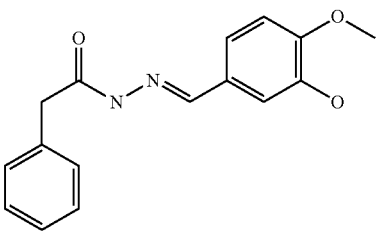 [SMILES: COc1ccc(/C=N/NC(=O)Cc2ccccc2)cc1O] | 282.29 |
| 12-99 | 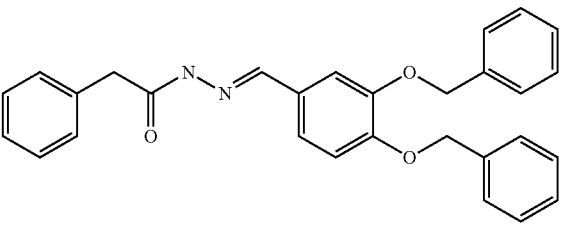 [SMILES: O=C(Cc1ccccc1)N/N=C/c1ccc(OCc2ccccc2)c(OCc2ccccc2)c1] | 449.52 |

TABLE 1-continued

| Example No. | Structure | MW |
|---|---|---|
| 12-100 | 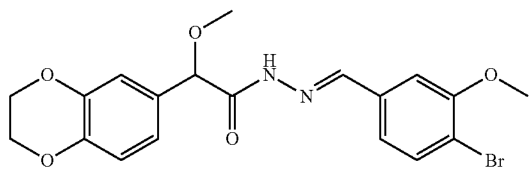 [SMILES: COc1cc(/C=N/NC(=O)C(OC)c2ccc3c(c2)OCCO3)ccc1Br] | 435.27 |
| 12-101 | 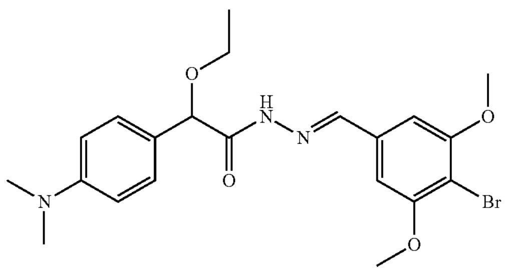 | 464.35 |
| 12-102 | 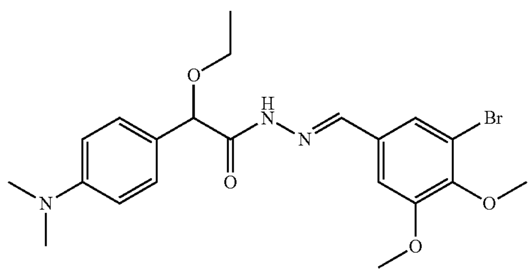 | 464.35 |
| 12-103 | 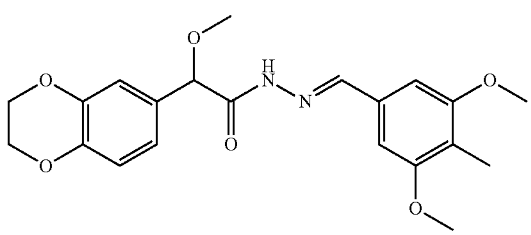 [SMILES: COc1cc(/C=N/NC(=O)C(OC)c2ccc3c(c2)OCCO3)cc(OC)c1C] | 400.43 |
| 12-104 | 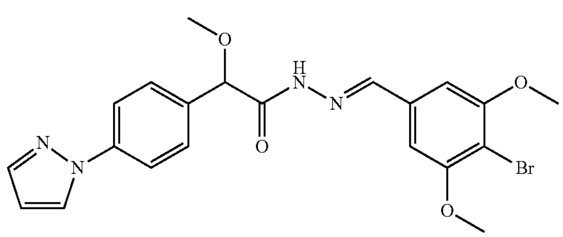 [SMILES: COc1cc(/C=N/NC(=O)C(OC)c2ccc(-n3cccn3)cc2)cc(OC)c1Br] | 473.3 |
| 12-105 | 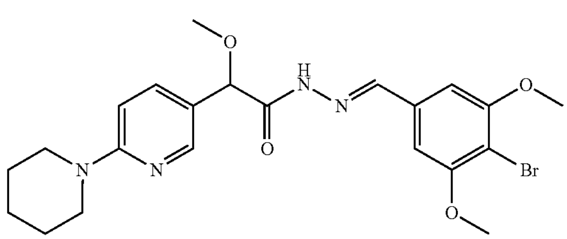 [SMILES: COc1cc(/C=N/NC(=O)C(OC)c2ccc(N3CCCCC3)nc2)cc(OC)c1Br] | 490.1 |

TABLE 1-continued

| Example No. | Structure | MW |
|---|---|---|
| 12-106 | 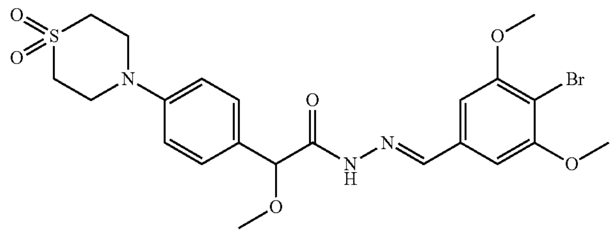 [SMILES: COc1cc(/C=N/NC(=O)C(OC)c2ccc(N3CCS(=O)(=O)CC3)cc2)cc(OC)c1Br] | 539.07 |
| 12-107 | 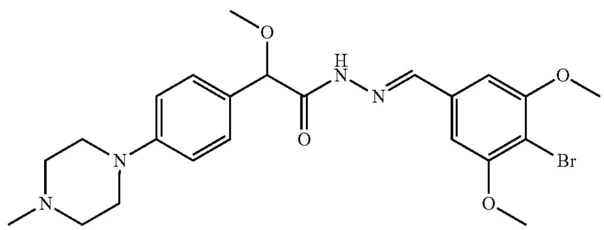 | 504.1 |
| 12-108 | 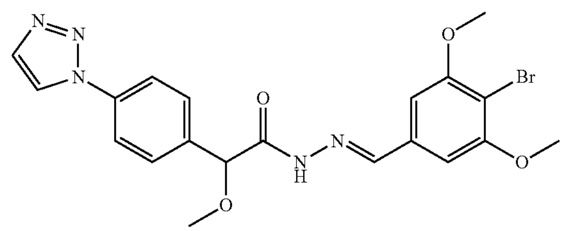 [SMILES: COc1cc(/C=N/NC(=O)C(OC)c2ccc(-n3ccnn3)cc2)cc(OC)c1Br] | 473.06 |
| 12-109 | 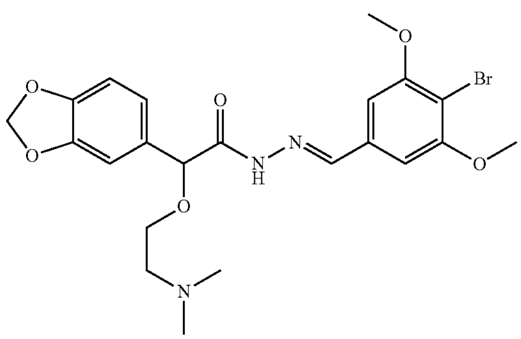 [SMILES: COc1cc(/C=N/NC(=O)C(OCCN(C)C)c2ccc3c(c2)OCO3)cc(OC)c1Br] | 507.10 |
| 12-110 | 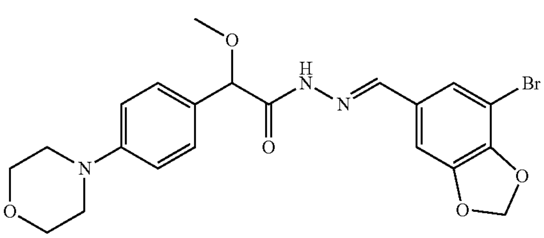 [SMILES: COC(C(=O)N/N=C/c1cc(Br)c2c(c1)OCO2)c1ccc(N2CCOCC2)cc1] | 475.074 |
| 12-111 | 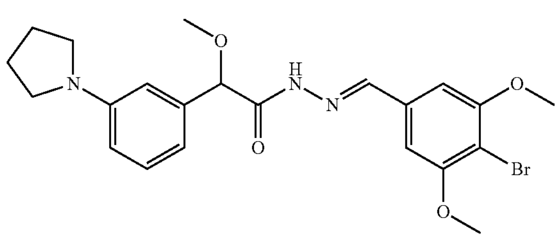 [SMILES: COc1cc(/C=N/NC(=O)C(OC)c2cccc(N3CCCC3)c2)cc(OC)c1Br] | 475.1 |

TABLE 1-continued

| Example No. | Structure | MW |
|---|---|---|
| 12-112 | 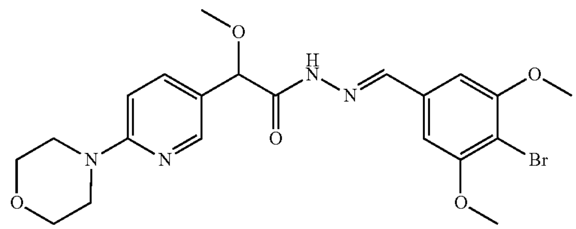 [SMILES: COc1cc(/C=N/NC(=O)C(OC)c2ccc(N3CCOCC3)nc2)cc(OC)c1Br] | 492.100 |
| 12-113 | 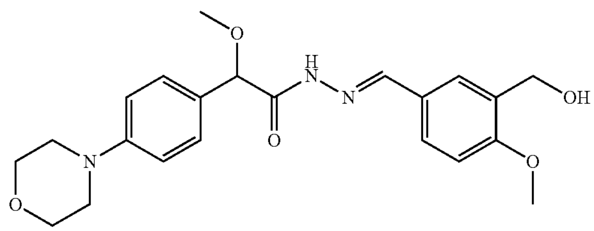 [SMILES: COc1ccc(/C=N/NC(=O)C(OC)c2ccc(N3CCOCC3)cc2)cc1CO] | 413.19 |
| 12-114 | 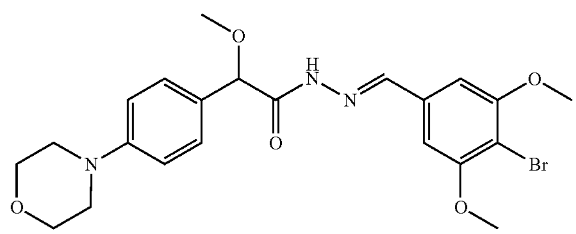 [SMILES: COc1cc(/C=N/NC(=O)C(OC)c2ccc(N3CCOCC3)cc2)cc(OC)c1Br] | 492.4 |
| 12-115 | 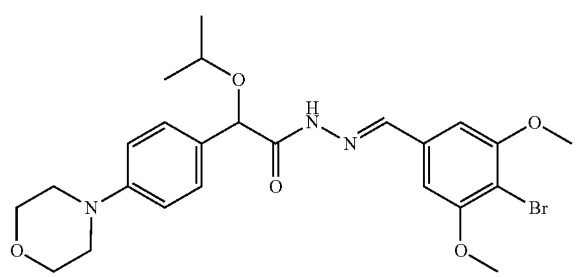 [SMILES: COc1cc(/C=N/NC(=O)C(OC(C)C)c2ccc(N3CCOCC3)cc2)cc(OC)c1Br] | 520.42 |
| 12-116 | 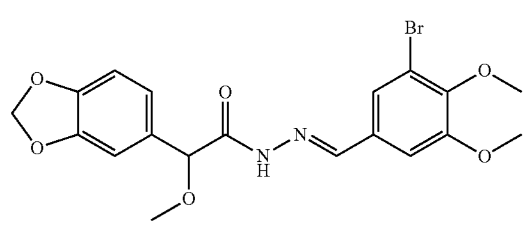 [SMILES: COc1cc(/C=N/NC(=O)C(OC)c2ccc3c(c2)OCO3)cc(Br)c1OC] | 450.04 |
| 12-117 | 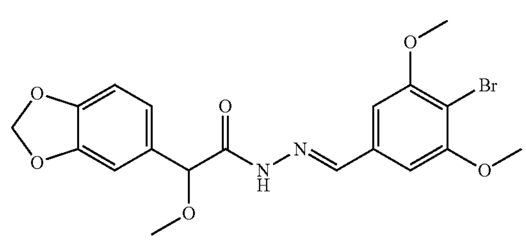 [SMILES: COc1cc(/C=N/NC(=O)C(OC)c2ccc3c(c2)OCO3)cc(OC)c1Br] | 460.074 |

TABLE 1-continued

| Example No. | Structure | MW |
|---|---|---|
| 12-118 | 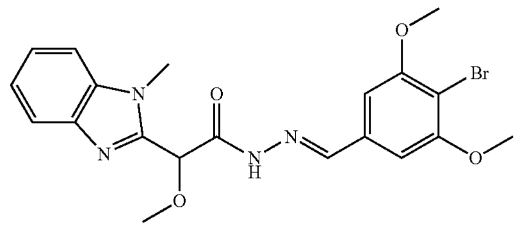 [SMILES: COc1cc(/C=N/NC(=O)C(OC)c2nc3ccccc3n2C)cc(OC)c1Br] | 443.047 |
| 12-119 | 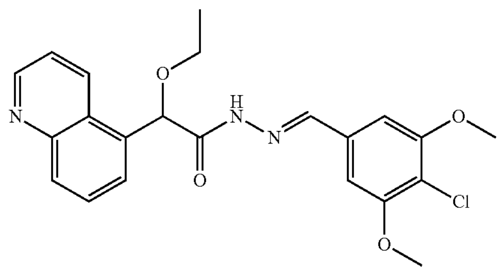 [SMILES: CCOC(C(=O)N/N=C/c1cc(OC)c(Cl)c(OC)c1)c1cccc2ncccc12] | 393.16 |
| 12-120 | 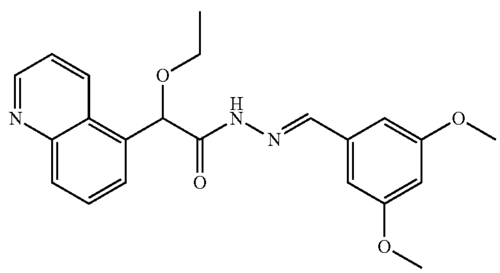 [SMILES: CCOC(C(=O)N/N=C/c1cc(OC)cc(OC)c1)c1cccc2ncccc12] | 460.074 |
| 12-121 | 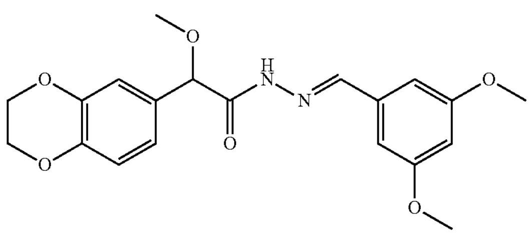 [SMILES: COc1cc(/C=N/NC(=O)C(OC)c2ccc3c(c2)OCCO3)cc(OC)c1] | 386.147 |
| 12-122 | 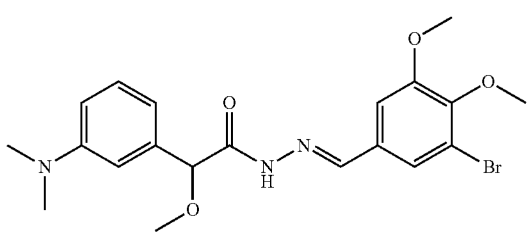 | 449.094 |
| 12-123 | 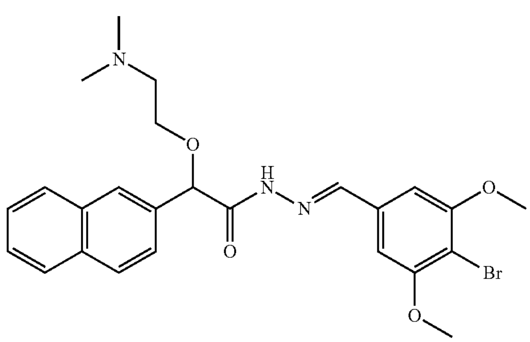 [SMILES: COc1cc(/C=N/NC(=O)C(OCCN(C)C)c2ccc3ccccc3c2)cc(OC)c1Br] | 513.126 |

TABLE 1-continued

| Example No. | Structure | MW |
|---|---|---|
| 12-124 | 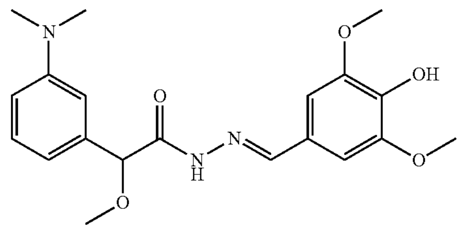 [SMILES: COc1cc(/C=N/NC(=O)C(OC)c2cccc(N(C)C)c2)cc(OC)c1O] | 387.1793 |
| 12-125 | 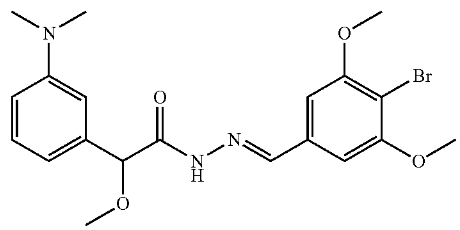 [SMILES: COc1cc(/C=N/NC(=O)C(OC)c2cccc(N(C)C)c2)cc(OC)c1Br] | 449.094 |
| 12-126 | 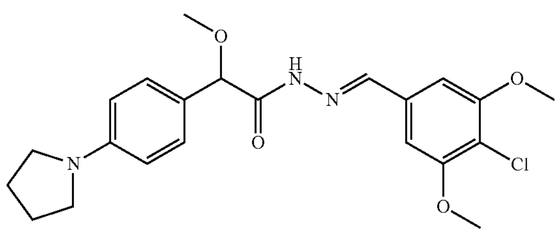 [SMILES: COc1cc(/C=N/NC(=O)C(OC)c2ccc(N3CCCC3)cc2)cc(OC)c1Cl] | 431.16 |
| 12-127 | 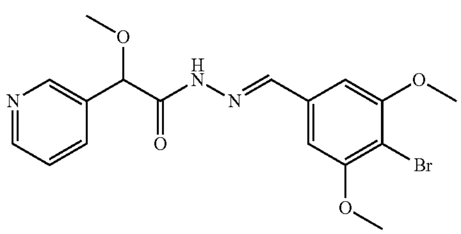 [SMILES: COc1cc(/C=N/NC(=O)C(OC)c2cccnc2)cc(OC)c1Br] | 406.052 |
| 12-128 | 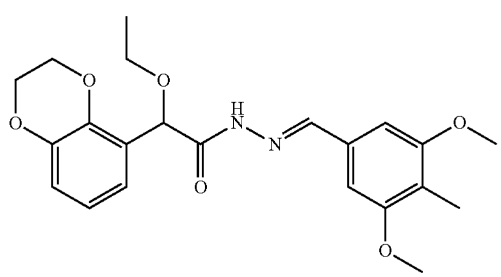 [SMILES: CCOC(C(=O)N/N=C/c1cc(OC)c(C)c(OC)c1)c1cccc2c1OCCO2] | 414.1790 |
| 12-129 | 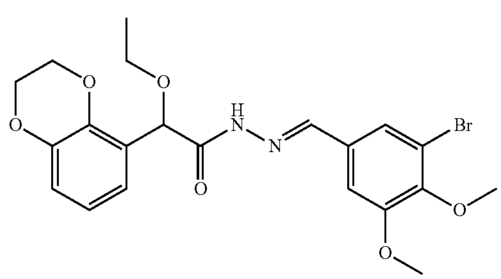 [SMILES: CCOC(C(=O)N/N=C/c1cc(Br)c(OC)c(OC)c1)c1cccc2c1OCCO2] | 478.0738 |

TABLE 1-continued

| Example No. | Structure | MW |
|---|---|---|
| 12-130 | 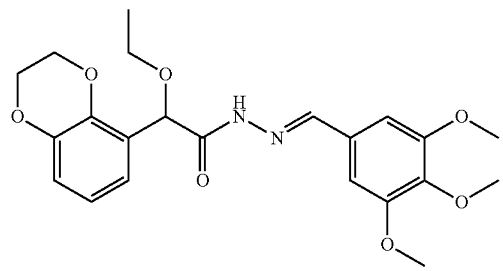 [SMILES: CCOC(C(=O)N/N=C/c1cc(OC)c(OC)c(OC)c1)c1cccc2c1OCCO2] | 430.17 |
| 12-131 | 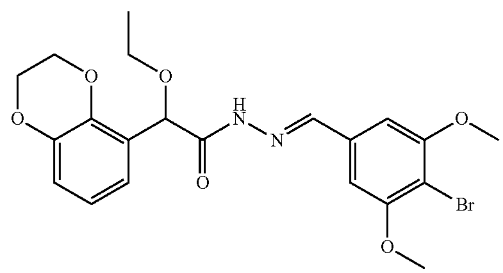 [SMILES: CCOC(C(=O)N/N=C/c1cc(OC)c(Br)c(OC)c1)c1cccc2c1OCCO2] | 478.07 |
| 12-132 | 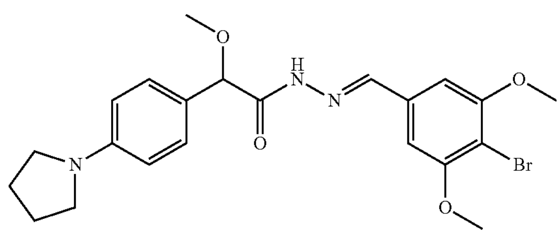 | 475.11 |
| 12-133 | 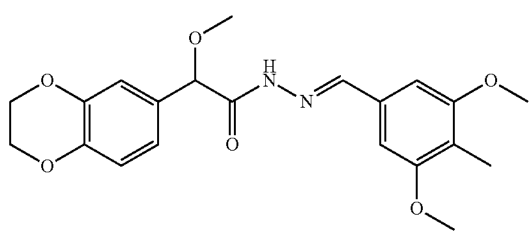 [SMILES: COc1cc(/C=N/NC(=O)C(OC)c2ccc3c(c2)OCCO3)cc(OC)c1C] | 400.16 |
| 12-134 | 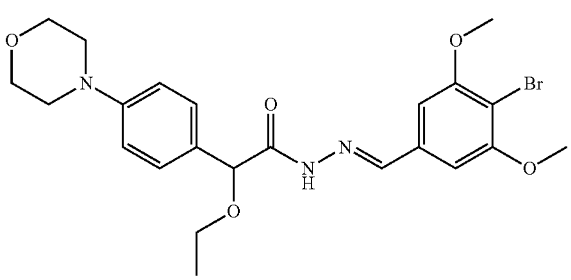 [SMILES: CCOC(C(=O)N/N=C/c1cc(OC)c(Br)c(OC)c1)c1ccc(N2CCOCC2)cc1] | 506.39 |
| 12-135 | 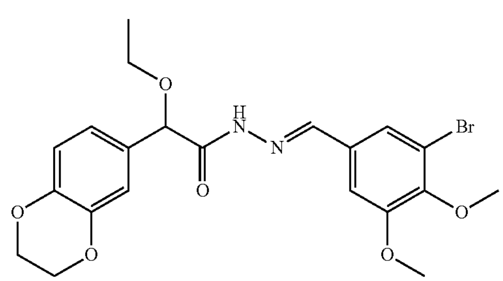 [SMILES: CCOC(C(=O)N/N=C/c1cc(Br)c(OC)c(OC)c1)c1ccc2c(c1)OCCO2] | 479.33 |

TABLE 1-continued
| Example No. | Structure | MW |
|---|---|---|
| 12-136 | 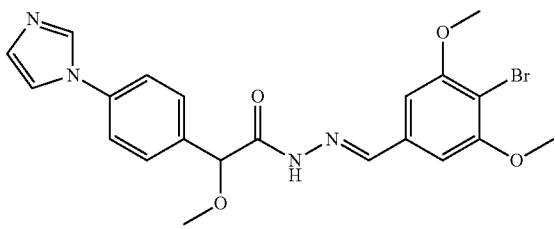 [SMILES: COc1cc(/C=N/NC(=O)C(OC)c2ccc(-n3ccnc3)cc2)cc(OC)c1Br] | 473.33 |
| 12-137 | 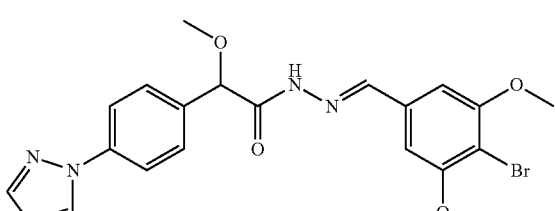 | 474.32 |
| 12-138 | 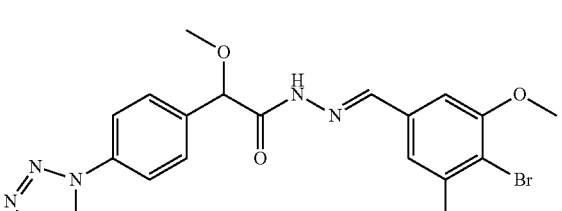 | 475.31 |
| 12-139 | 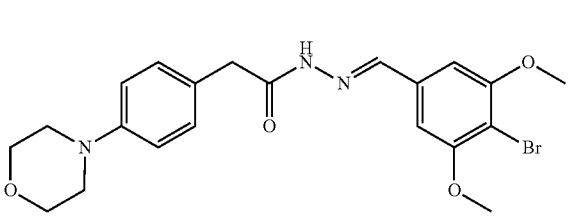 [SMILES: COc1cc(/C=N/NC(=O)Cc2ccc(N3CCOCC3)cc2)cc(OC)c1Br] | 462.36 |
| 12-140 | 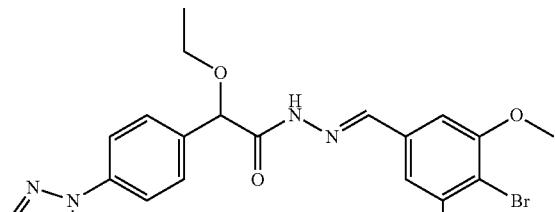 | 487.36 |
| 12-141 | 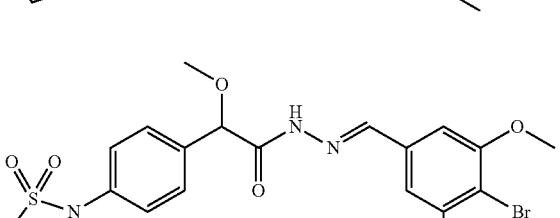 | 526.41 |

TABLE 1-continued

| Example No. | Structure | MW |
|---|---|---|
| 12-142 | 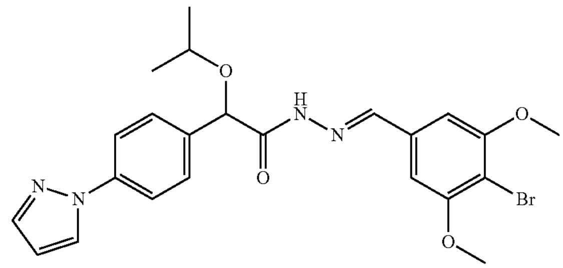 [SMILES: COc1cc(/C=N/NC(=O)C(OC(C)C)c2ccc(-n3cccn3)cc2)cc(OC)c1Br] | 501.39 |
| 12-143 | 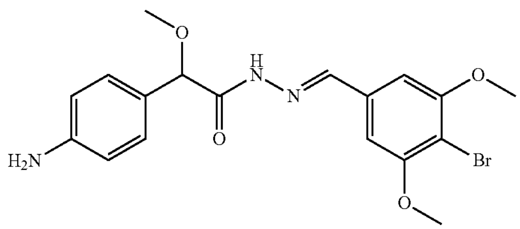 [SMILES: COc1cc(/C=N/NC(=O)C(OC)c2ccc(N)cc2)cc(OC)c1Br] | 422.27 |
| 12-144 | 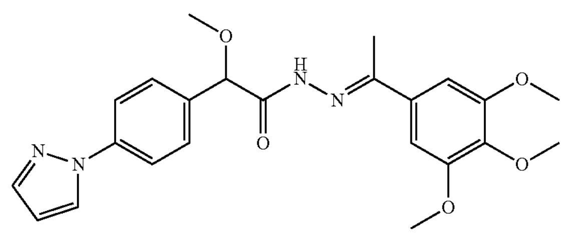 [SMILES: COc1cc(/C(C)=N/NC(=O)C(OC)c2ccc(-n3cccn3)cc2)cc(OC)c1OC] | 438.48 |
| 12-145 | 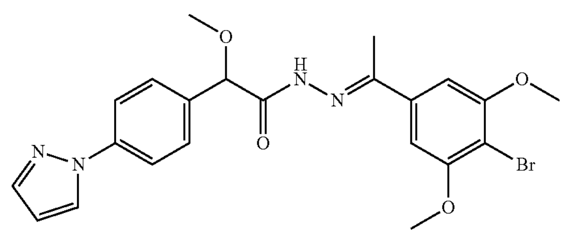 [SMILES: COc1cc(/C(C)=N/NC(=O)C(OC)c2ccc(-n3cccn3)cc2)cc(OC)c1Br] | 487.35 |
| 12-146 | 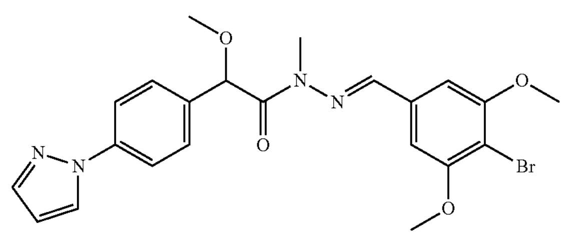 [SMILES: COc1cc(/C=N/N(C)C(=O)C(OC)c2ccc(-n3cccn3)cc2)cc(OC)c1Br] | 487.35 |
| 12-147 | 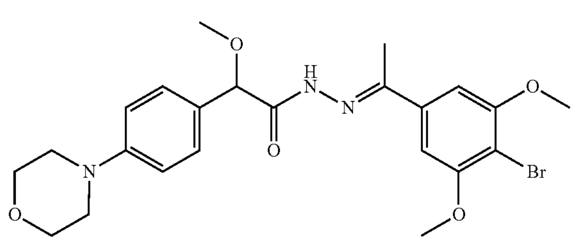 [SMILES: COc1cc(/C(C)=N/NC(=O)C(OC)c2ccc(N3CCOCC3)cc2)cc(OC)c1Br] | 506.39 |

TABLE 1-continued

| Example No. | Structure | MW |
|---|---|---|
| 12-148 | 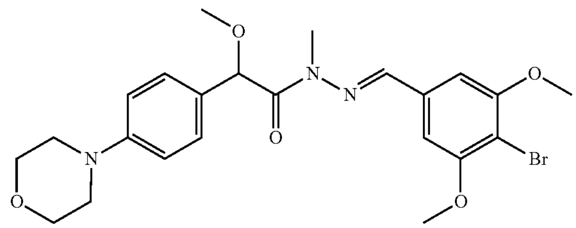 [SMILES: COc1cc(/C=N/N(C)C(=O)C(OC)c2ccc(N3CCOCC3)cc2)cc(OC)c1Br] | 506.39 |
| 12-149 | 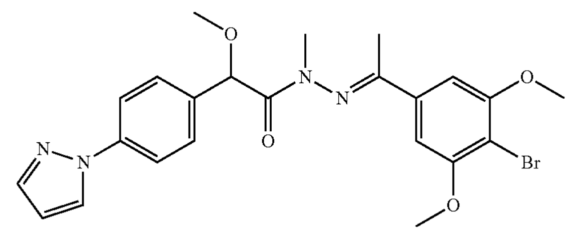 [SMILES: COc1cc(/C(C)=N/N(C)C(=O)C(OC)c2ccc(-n3cccn3)cc2)cc(OC)c1Br] | 501.37 |
| 12-150 | 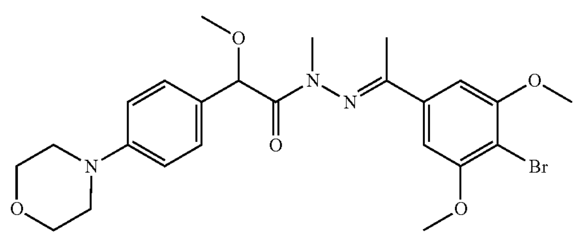 [SMILES: COc1cc(/C(C)=N/N(C)C(=O)C(OC)c2ccc(N3CCOCC3)cc2)cc(OC)c1Br] | 520.42 |
| 12-151 | 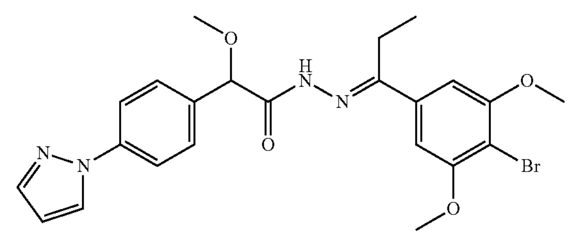 [SMILES: CC/C(=N\NC(=O)C(OC)c1ccc(-n2cccn2)cc1)c1cc(OC)c(Br)c(OC)c1] | 501.37 |
| 12-152 | 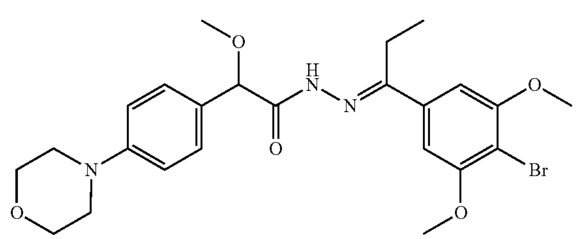 [SMILES: CC/C(=N\NC(=O)C(OC)c1ccc(N2CCOCC2)cc1)c1cc(OC)c(Br)c(OC)c1] | 520.42 |
| 12-153 | 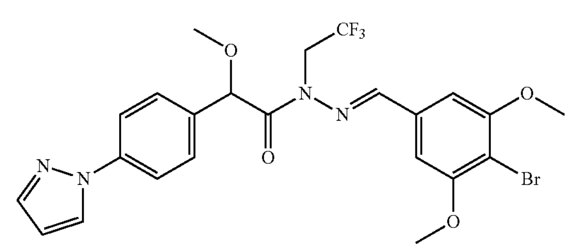 [SMILES: COc1cc(/C=N/N(CC(F)(F)F)C(=O)C(OC)c2ccc(-n3cccn3)cc2)cc(OC)c1Br] | 555.34 |

TABLE 1-continued

| Example No. | Structure | MW |
|---|---|---|
| 12-154 | 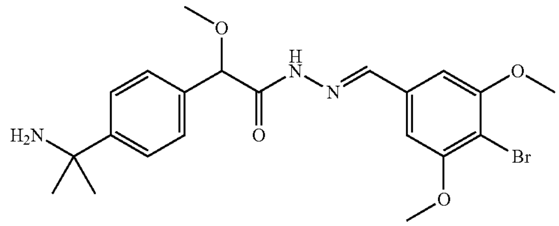 [SMILES: COc1cc(/C=N/NC(=O)C(OC)c2ccc(C(C)(C)N)cc2)cc(OC)c1Br] | 464.35 |
| 12-155 | 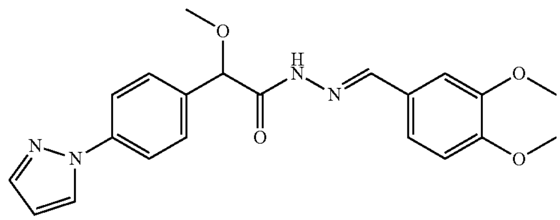 [SMILES: COc1ccc(/C=N/NC(=O)C(OC)c2ccc(-n3cccn3)cc2)cc1OC] | 394.42 |
| 12-156 | 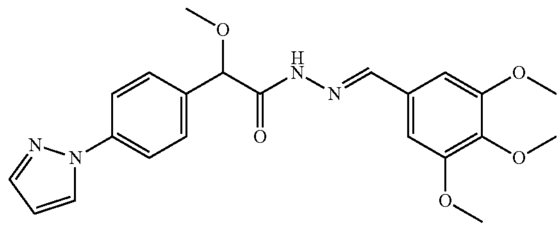 [SMILES: COc1cc(/C=N/NC(=O)C(OC)c2ccc(-n3cccn3)cc2)cc(OC)c1OC] | 424.45 |

Example 13

Compound Assay

PDE10 Biochemical Assay

The phosphodiesterase (PDE) assay was performed using recombinant human PDE 1A3, 2A3, 3 catalytic region, 4 catalytic region, 5 catalytic region, 7A, 8A, 9A2, 10A1 and 11A1 enzymes expressed in a baculoviral system using Sf9 cells. PDE activity was measured using a modification of the two-step method of Thompson and Appleman described above which was adapted for 96 well plate format. The effect of the PDE inhibitors was determined by assaying a fixed amount of the enzyme in the presence of test compound concentrations and a substrate concentration below that of the Km, so that Ki equals $IC_{50}$. The final assay volume was 110l with assay buffer (10 mM $MgCl_2$; 40 mM Tris.HCl; pH 7.4). Reactions were initiated with enzyme and incubated with ($^3$H)-substrate and substance for 20 minutes at 30° C. The reaction was terminated by denaturing the enzyme (heating the reaction to 70° C. for 2 minutes). The reaction was then cooled at 4° C. for 10 minutes before the addition of snake venom (Crotalus atrox, 0.2 mg/ml) for 10 minutes at 30° C., thus allowing non-specific hydrolysis of the tritiated substrate. Separation of the remaining unhydrolysed cyclic nucleotide was achieved by a batch binding of the mixture to activated Dowex (200 µl) anion exchange resin. The anion exchange resin bound the charged nucleotides, leaving only hydrolysed ($^3$H) substrate in the soluble fraction. The soluble fraction (50 µl) was then added to microscint-20 (200 µl) and counted on a Top Count Plate reader. Radioactivity units were plotted against inhibitor concentration and $IC_{50}$ values obtained using Graph Pad Prism software.

Alternatively, phosphodiesterase activity was measured by scintillation proximity assay (SPA) with [$^3$H]-cGMP as substrate. Purified PDE10 was diluted and stored in 25 mM Tris-Cl (pH 8.0)/100 mM NaCl/0.05% Tween 20/50% glycerol/3 mM DTT. Assays contained (final concentrations): 50 mM Tris-Cl (pH 7.5)/8.3 mM $MgCl_2$/1.7 mM EGTA/0.5 mg/ml BSA/5% DMSO and 2 ng PDE10 in a final volume of 0.1 mL. Inhibition was evaluated at 8 concentrations in duplicate. Reactions were initiated by addition of enzyme and were terminated after 20 minutes at 30° C. by the addition of 50 µl of SPA beads containing $Zn^{++}$. The mixture was shaken, allowed to settle for 3 hours, and counted in a Wallac plate counter. Results (net cpm) were fitted to a four parameter logistic model using Excel Solver®.

Further, the inhibition of other PDE enzymes by the PDE10 inhibitors was evaluated under the same conditions described above for PDE10 except the amount of enzyme added was optimized for each PDE. Fractional inhibition was evaluated at four concentrations (0.1, 1, 10, and 100 µM). In cases where inhibition at the highest concentration was less than 50%, the lower limit value in the logistic model was fixed 30 to 0% activity.

In the above assay, compounds of this invention are PDE10 inhibitors with an $IC_{50}$ of 100 µM or less, generally less than 10 µM, and typically less than 1 µM. To this end, compounds 1-1, 2-1, 3-1, 4-1, 5-1, 6-1, 7-1, 8-1, 9-1, 11-1, 12-1, 12-2, 12-3, 12-4, 12-5, 12-6, 12-7, 12-8, 12-9, 12-10, 12-12, 12-13, 12-14, 12-15, 12-16, 12-17, 12-18, 12-19, 12-20, 12-21, 12-22, 12-23, 12-24, 12-25, 12-26, 12-41, 12-42, 12-43, 12-44, 12-45, 12-46, 12-47, 12-48, 12-49, 12-50, 12-51, 12-52, 12-55, 12-56, 12-57, 12-58, 12-59, 12-60, 12-61, 12-62, 12-63, 12-64, 12-65, 12-66, 12-67, 12-68, 12-69, 12-70, 12-71, 12-80, 12-82, 12-83, 12-84, 12-85, 12-86, 12-87, 12-88, 12-89, 12-90, 12-104, 12-105, 12-107, 12-108, 12-109, 12-111, 12-112, 12-114, 12-115, 12-116, 12-117, 12-118, 12-119, 12-120, 12-121, 12-122, 12-123, 12-124, 12-125, 12-126, 12-127, 12-128, 12-129, 12-130, 12-131, 12-132, 12-133, 12-134, 12-135, 12-136, 12-137, 12-138, 12-139, 12-140, 12-141, 12-142, 12-144 and 12-155 for example, were found to have $IC_{50}$ values of less than or equal to 1 μM.

Examples 14-15

Evaluation of Representative Compounds in Behavioral Models

Schizophrenia has been associated with dysfunctions of dopaminergic, glutamatergic and serotonergic neurotransmission. Psychostimulant drugs in these three classes, dopaminergic agonists (such as amphetamine and apomorphine), glutamatergic antagonists (such as PCP and ketamine), and serotonergic agonists (such as LSD and MDMA), all induce psychotomimetic states (e.g., hyperactivity and disruption of prepulse inhibition) in animals that closely resemble schizophrenia symptoms in humans. Known antipsychotic drugs, including both typical antipsychotics (e.g., haloperidol) and atypical antipsychotics (e.g., olanzapine), reverse such psychotomimetic states in animals. Examples 14-15 described below evaluate representative compounds of the present invention in animal behavioral models to compare the resulting effect to that of known antipsychotics. Methods used in the Examples 14-15 are as follows.

Psychostimulant-induced hyperactivity is measured by injecting animals with PCP and monitoring the animals' activity levels in the VersaMax chambers (Accuscan Instruments, Columbus, Ohio) measuring 40×40 cm. Locomotor activity is detected by photobeam breaks as the animal crosses each beam. The animal is placed in the center of the field and left undisturbed for a period of time (20 min to 2 hr) to measure its spontaneous activity in a novel environment. Measurements used to assess locomotor activity include: horizontal activity, total distance traveled, vertical activity (rearing events—animal raises up on hindlimbs), rotation, stereotypy, and distance traveled in the center compared to total distance traveled (center: total distance ratio). The NMDA antagonist PCP induces psychosis-like conditions manifested as hyperactivity and increased stereotypic behavior. Known antipsychotics are able to reverse psychostimulant-induced hyperactivity and increased stereotypy.

Conditioned avoidance response (CAR) is a behavioral test to evaluate antipsychotic effect of a test compound. It utilizes a shuttle box (Med Associates, St. Albans, Vt.) with two equal chambers separated by a retractable door. Each chamber is fitted with metal grid floor that is capable of delivering electric shocks independently. A computer program is used to implement the testing paradigm as well as record the animal's movement between the two chambers through infrared beam sensors. The testing paradigm is as the follows. A mouse is placed into one chamber. A light (conditioned stimulus, CS) comes on. Five seconds later, mild electric shocks (0.4 mA) (unconditioned stimulus, US) are delivered to the chamber where the mouse is located (as detected by infrared beams) until the mouse escapes to the adjacent chamber or until 10 sec has elapsed. The US and CS always co-terminate. With randomized inter-trial intervals averaging 15 sec, 30 such CS-US pairing trials are given to each mouse each day. For each trial, an escape response is registered if the mouse crosses to the other chamber after being shocked (i.e., during the 10-sec US period), and an avoidance response is registered if the mouse crosses to the other chamber during the first 5-sec CS only period. The animals are trained in such paradigm for 15-20 days, during which the average percentage of avoidance responses will improve to 60-80%. This indicates that animals have learned to avoid the onset of footshocks by moving to the opposite chamber upon activation of the CS (light). These trained animals are then used for compound testing using the same paradigm. Known antipsychotics have been found to inhibit the conditioned avoidance response, and the ability of new compounds to inhibit this response is thought to be predictive of antipsychotic effect in humans.

Example 14

Reduction of PCP-Induced Hyperactivity

Figure 2:
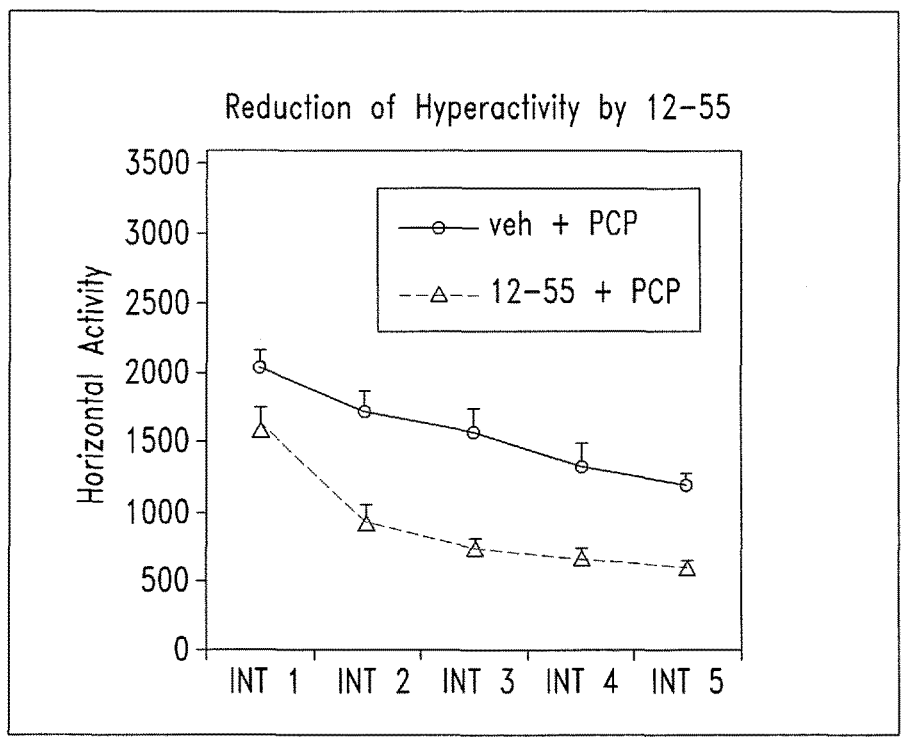
FIG. 2 illustrates that Compound 12-55 of the present invention (as identified in Table 1 of Example 12) significantly reduces hyperactivity of mice in the PCP-induced model of psychosis as compared to vehicle control.
Figure 3:
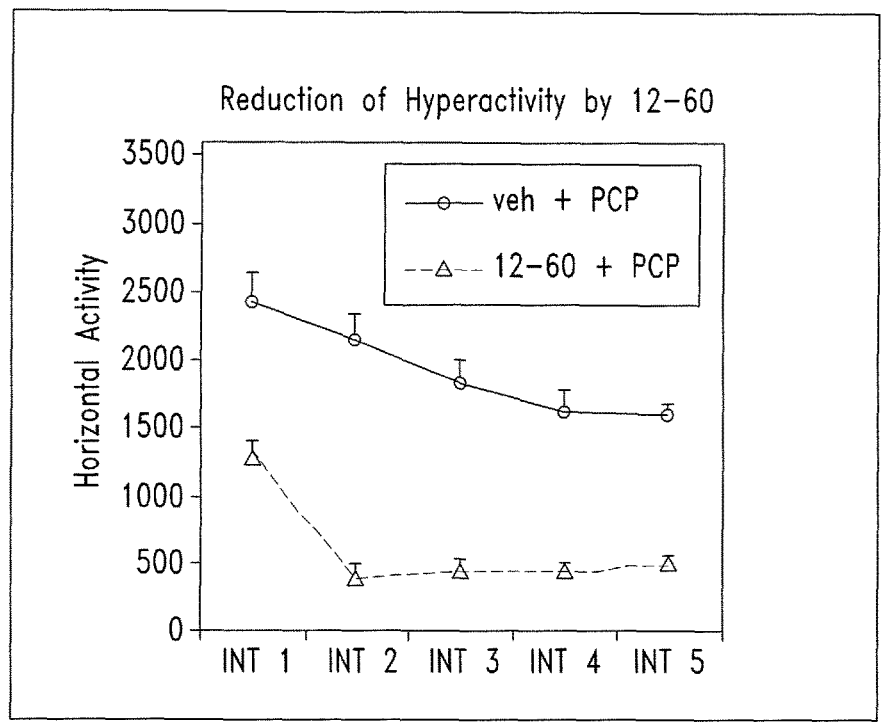
FIG. 3 illustrates that Compound 12-60 of the present invention (as identified in Table 1 of Example 12) significantly reduces hyperactivity of mice in the PCP-induced model of psychosis as compared to vehicle control.

Compounds 12-63, 12-55 and 12-60 of the present invention (as identified in Table 1 of Example 12) were evaluated for the ability to significantly and substantially reduce PCP-induced hyperactivity. C57BL/6 male mice were injected with either compound (10 mg/kg) or vehicle via i.p. Ten minutes later, the mice were injected with PCP (5 mg/kg) via i.p. The mice were placed in the activity chambers 10 minutes after PCP injection and their locomotor activities were monitored by infrared beam breaks for 20 min. FIG. 1 shows that Compound 12-63 significantly reduced the hyperactivity elicited by PCP compared to vehicle (p<0.0001, n=8 per group, repeated measures ANOVA). FIG. 2 shows that Compound 12-55 (10 mg/kg, i.p.) also substantially reduces hyperactivity (p=0.0008 compared to vehicle, n=8 per group, repeated measures ANOVA) and FIG. 3 shows a similar result with Compound 12-60 (p<0.0001 compared to vehicle, n=8 per group, repeated measures ANOVA).

Example 15

Reduction of Conditioned Avoidance Response

Figure 4:
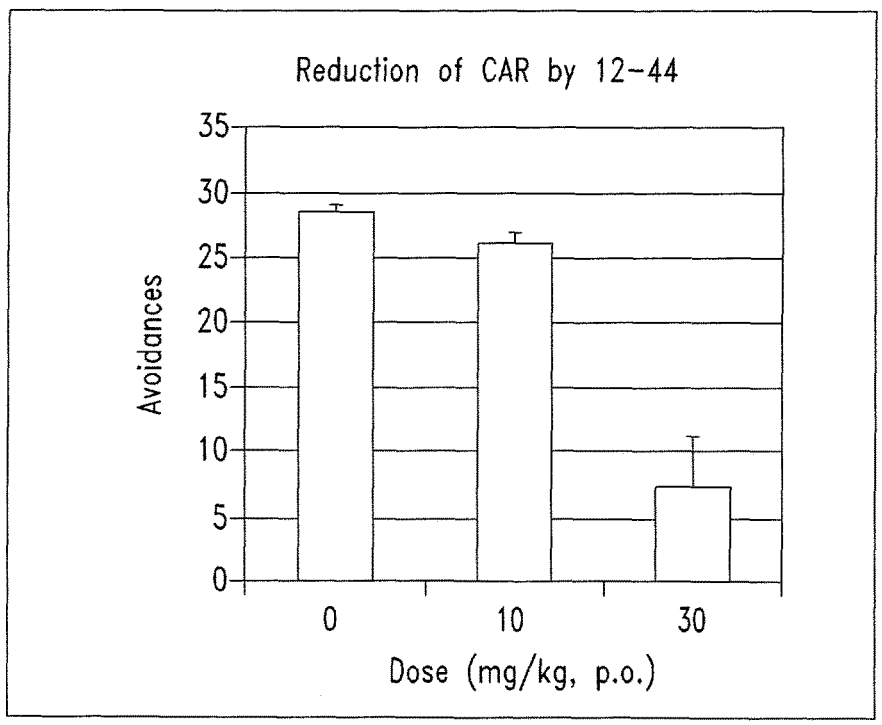
FIG. 4 illustrates that Compound 12-44 of the present invention (as identified in Table 1 of Example 12) significantly reduces a conditioned avoidance response (CAR) in mice trained in a CAR model of psychosis as compared to vehicle control.

Compound 12-44 of the present invention (as identified in Table 1 of Example 12) was evaluated for the ability to reduce Conditioned Avoidance Response after oral dosing, as shown in FIG. 4. C57BL/6 male mice were trained in the CAR paradigm to predict and avoid the noxious stimulus, reaching a plateau of approximately 20-25 avoidance responses per 30 trials ("training plateau") each day. The mice were then injected with either compound or vehicle via i.p., and 20 minutes later they were tested for 30 trials in the CAR paradigm. Vehicle treatment and compound treatment were given to the same animals on alternating days, and the effect of compound in reducing avoidance response was analyzed through within-subject comparison (paired t-test). Vehicle exposure ("vehicle") does not alter the avoidance response of these trained animals. FIG. 4 shows that Compound 12-44 significantly reduces the number of avoidance responses at oral doses of both 10 mg/kg (p=0.01, n=6 per group, paired t-test) and 30 mg/kg (p=0.001, n=6 per group, paired t-test). At the latter dose, the number of avoidances is substantially reduced from 28 to 7.

Example 16

Reduction of PCP-Induced Hyperactivity by Compound 12-63

Figure 5A:
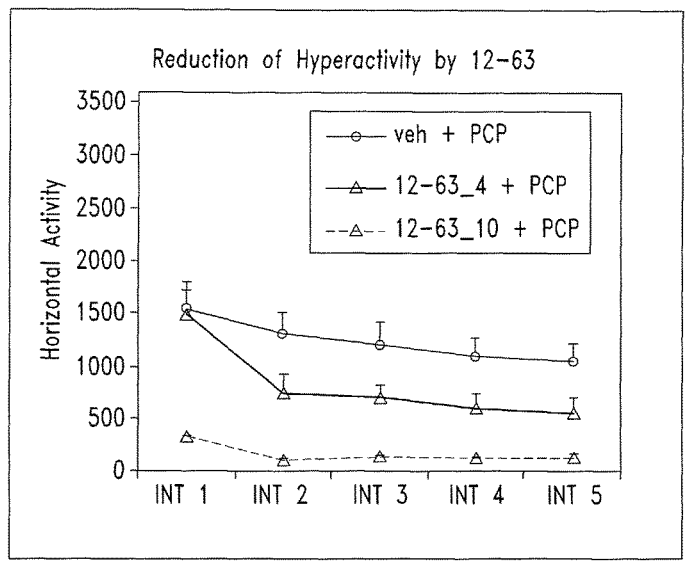
FIGS. 5A and 5B illustrate that Compound 12-63 of the present invention (as identified in Table 1 of Example 12) significantly reduces hyperactivity of mice in the PCP-induced model of psychosis as compared to vehicle control (FIG. 5A) and significantly reduces a conditioned avoidance response (CAR) in mice trained in a CAR model of psychosis as compared to vehicle control (FIG. 5B).

Compound 12-63 (as identified in Table 1 of Example 12) was found to reduce PCP-induced hyperactivity, as shown in FIG. 5A. C57BL/6 male mice were administered either compound or vehicle via oral gavage. Fifteen minutes later, the mice were injected with PCP (5 mg/kg) via the i.p. route. The mice were placed in activity chambers 10 minutes after PCP injection, and their locomotor activity in the horizontal dimension was monitored by infrared beam breaks for 20 min (5 consecutive 4-minute intervals (INT) as indicated). FIG. 5A shows that Compound 12-63 (4 and 10 mg/kg) reduces or abolishes the hyperactivity induced by PCP compared to the vehicle+PCP control group (p=0.00003 for 10 mg/kg dose, n=8 per group, paired t-test).

Example 17

Reduction of Conditioned Avoidance Response by Compound 12-63

Figure 5B:
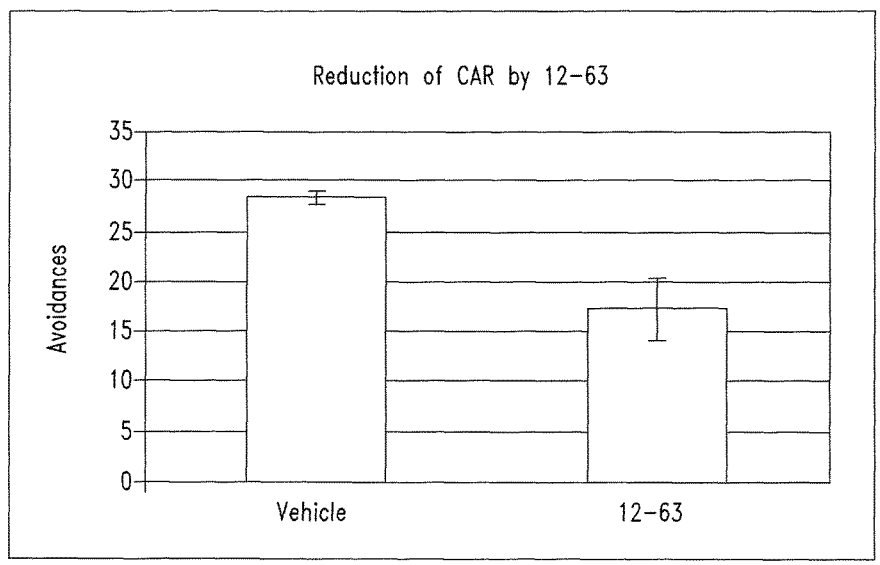

Compound 12-63 (as identified in Table 1 of Example 12) was found to reduce Conditioned Avoidance Responses (CAR), as shown in FIG. 5B. C57BL/6 male mice were trained in the CAR paradigm to predict and avoid the noxious stimulus (foot shock), reaching a plateau of approximately 25 avoidance responses per 30 trials ("training plateau"). The mice were then given either vehicle (15 minutes prior to testing) or compound (25 minutes prior to testing) via oral gavage, and were tested for 30 trials in the CAR paradigm. Vehicle treatment and compound treatment were given to the same animals on alternating days, and the effect of compound in reducing avoidance response was analyzed through within-subject comparison (paired t-test). Vehicle exposure ("vehicle") does not alter the avoidance response of these trained animals. FIG. 5B shows that Compound 12-63 (10 mg/kg) significantly reduces the number of avoidance response (p=0.007, n=6 per group). In all these cases, the number of escape responses increased correspondingly and the total numbers of transitions between the two chambers did not change (data not shown), indicating a specific reduction of CAR that is not due to compromised motor function.

Example 18

Reduction of PCP-Induced Hyperactivity by Compound 12-104

Figure 6A:
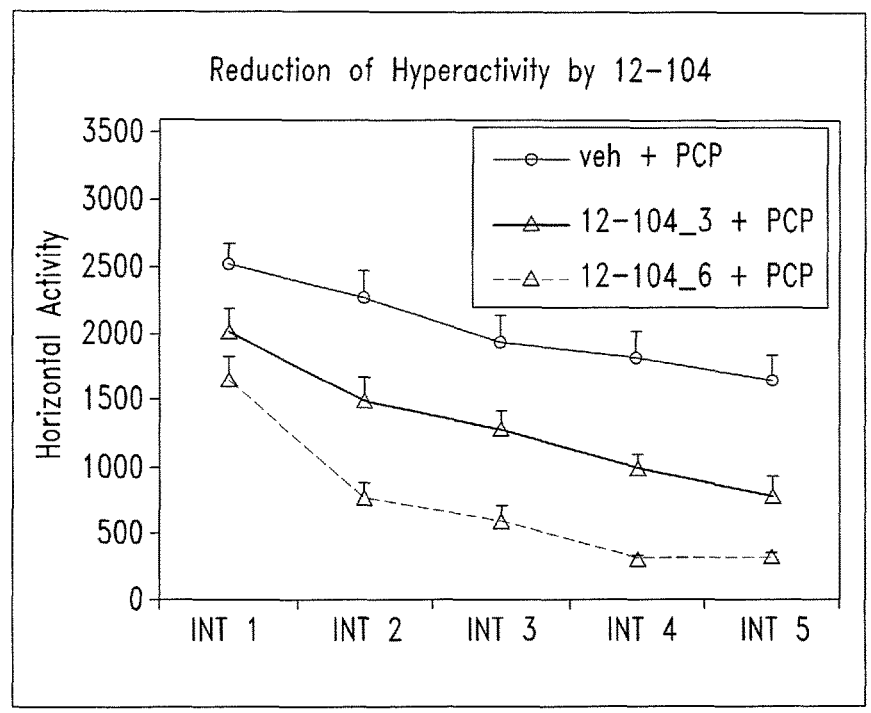
FIGS. 6A and 6B illustrate that Compound 12-104 of the present invention (as identified in Table 1 of Example 12) significantly reduces hyperactivity of mice in the PCP-induced model of psychosis as compared to vehicle control (FIG. 6A) and significantly reduces a conditioned avoidance response (CAR) in mice trained in a CAR model of psychosis as compared to vehicle control (FIG. 6B).

Compound 12-104 (as identified in Table 1 of Example 12) was found to reduce PCP-induced hyperactivity, as shown in FIG. 6A. C57BL/6 male mice were administered either compound or vehicle via oral gavage. Twenty-five minutes later, the mice were injected with PCP (5 mg/kg) via the i.p. route. The mice were placed in activity chambers 10 minutes after PCP injection and their locomotor activity in the horizontal dimension was monitored by infrared beam breaks for 20 min (5 consecutive 4-minute intervals (INT) as indicated). FIG. 6A shows that Compound 12-104 (3 and 6 mg/kg) reduces or abolishes the hyperactivity induced by PCP, as seen by comparison with the vehicle+PCP control (p=0.0189, n=8 per group, independent sample t-test).

Example 19

Reduction of Conditioned Avoidance Response by Compound 12-104

Figure 6B:
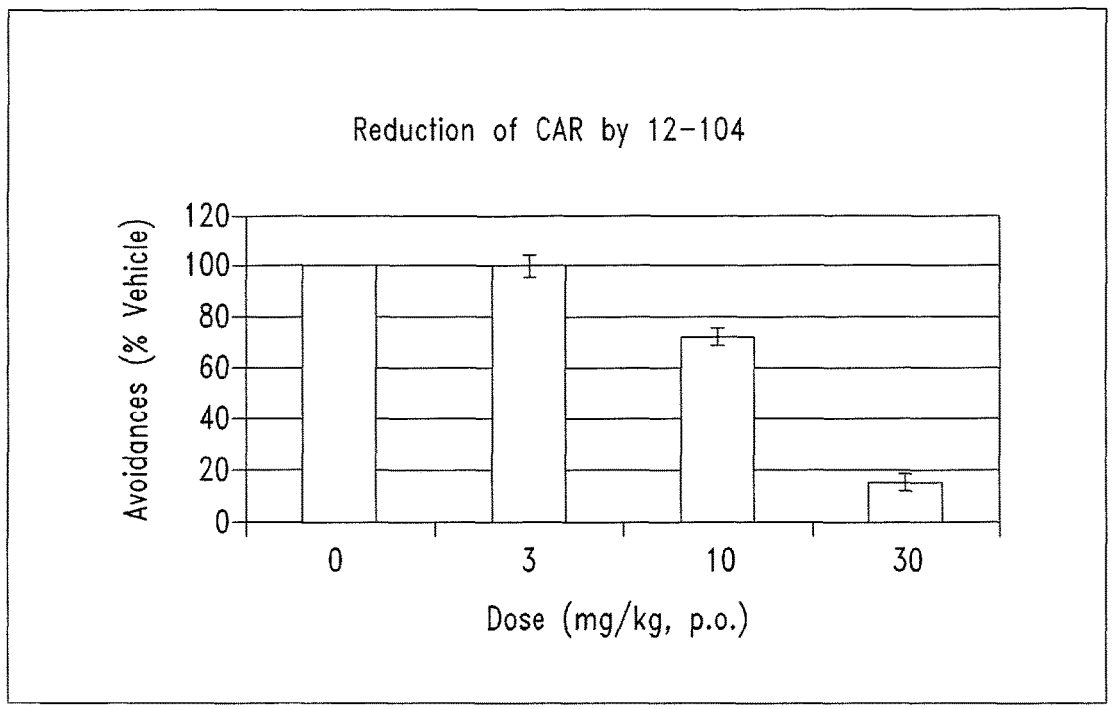

Compound 12-104 (as identified in Table 1 of Example 12) was found to reduce Conditioned Avoidance Responses (CAR), as shown in FIG. 6B. C57BL/6 male mice were trained in the CAR paradigm to predict and avoid the noxious stimulus (foot shock), reaching a plateau of approximately 25 avoidance responses per 30 trials each day. The mice were then given either vehicle (15 minutes prior to testing) or compound (25 minutes prior to testing) via oral gavage, and then were tested for 30 trials in the CAR paradigm. Vehicle treatment and compound treatment were given to the same animals on alternating days, and the effect of compound in reducing avoidance response was analyzed through within-subject comparison (paired t-test). Vehicle exposure ("vehicle") does not alter the avoidance response of these trained animals. FIG. 6B shows that Compound 12-104 (10 and 30 mg/kg) significantly reduces the number of avoidance response (p=0.0159, n=7 per group).

Example 20

Reduction of PCP-Induced Hyperactivity by Compound 12-114

Figure 7A:
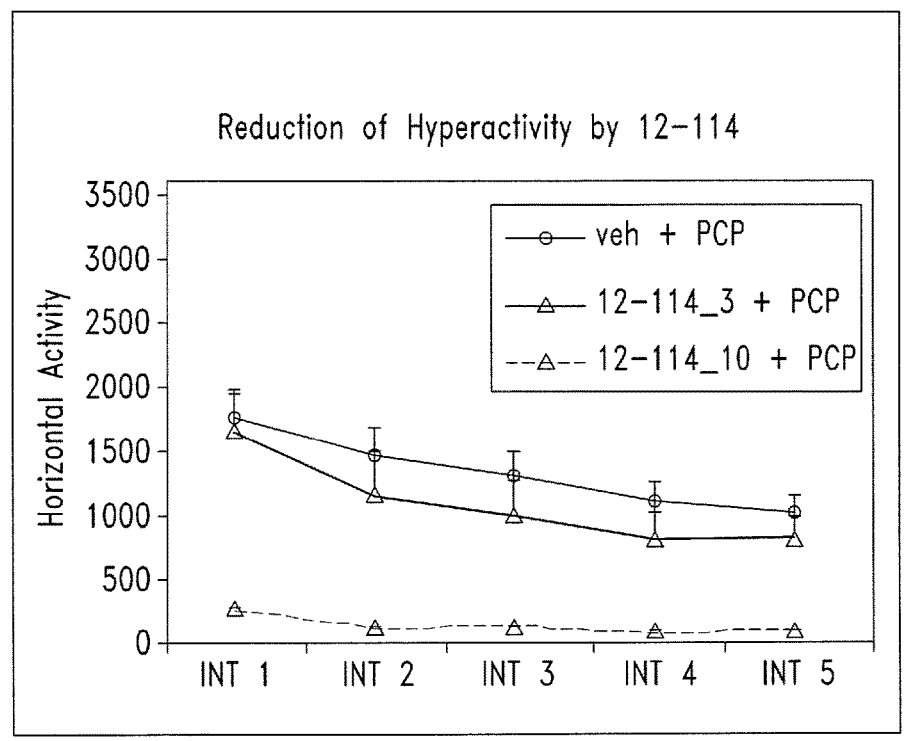
FIGS. 7A and 7B illustrate that Compound 12-114 of the present invention (as identified in Table 1 of Example 12) significantly reduces hyperactivity of mice in the PCP-induced model of psychosis as compared to vehicle control (FIG. 7A) and significantly reduces a conditioned avoidance response (CAR) in mice trained in a CAR model of psychosis as compared to vehicle control (FIG. 7B).

Compound 12-114 (as identified in Table 1 of Example 12) was found to reduce PCP-induced hyperactivity, as shown in FIG. 7A. C57BL/6 male mice were given either compound or vehicle by oral gavage. Twenty-five minutes later they were injected with PCP (5 mg/kg, i.p.). Ten minutes later, the mice were placed in activity chambers, and their locomotor activity in the horizontal dimension was monitored by infrared beam breaks for 20 min (5 consecutive 4-minute intervals (INT) as indicated). FIG. 7A shows that Compound 12-114 (10 mg/kg) completely abolishes the hyperactivity induced by PCP, as seen by comparison to the vehicle+PCP control (p<0.0000001, n=8 per group, independent sample t-test).

Example 21

Reduction of Conditioned Avoidance Response by Compound 12-114

Figure 7B:
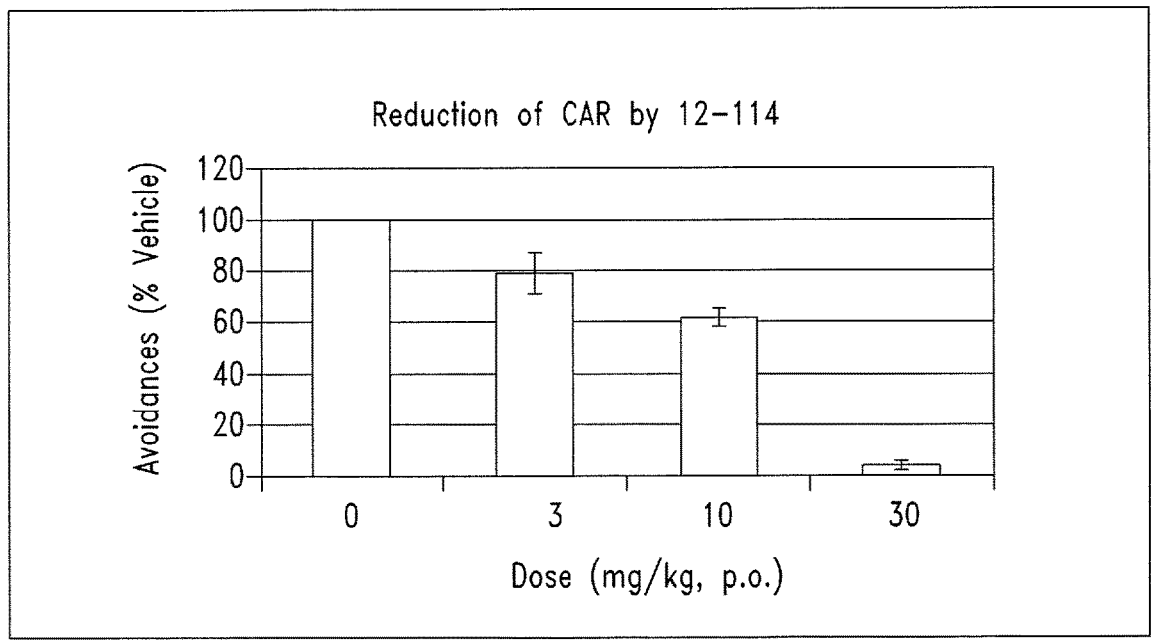

Compound 12-114 (as identified in Table 1 of Example 12) was found to reduce Conditioned Avoidance Responses (CAR), as shown in FIG. 7B. C57BL/6 male mice were trained in the CAR paradigm to predict and avoid the noxious stimulus (foot shock), reaching a plateau of approximately 25 avoidance responses per 30 trials each day. The mice were then given either vehicle (15 minutes prior to testing) or compound (25 minutes prior to testing) via oral gavage, and then were tested for 30 trials in the CAR paradigm. Vehicle treatment and compound treatment were given to the same animals on alternating days, and the effect of compound in reducing avoidance response was analyzed through within-subject comparison (paired t-test). Vehicle exposure ("vehicle") does not alter the avoidance response of these trained animals. FIG. 7B shows that Compound 12-114 (10 mg/kg) significantly reduces the number of avoidance response (p=0.0003, n=7 per group, paired t-test).

Example 22

Reduction of PCP-Induced Hyperactivity by Compound 12-132

Figure 8A:
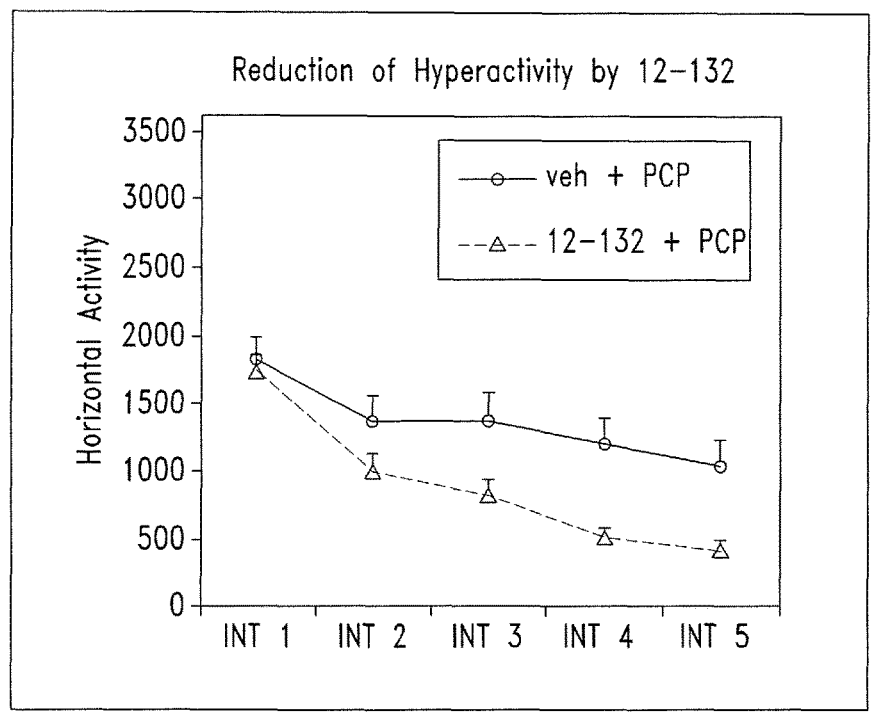
FIGS. 8A and 8B illustrate that Compound 12-132 of the present invention (as identified in Table 1 of Example 12) significantly reduces hyperactivity of mice in the PCP-induced model of psychosis as compared to vehicle control (FIG. 8A) and significantly reduces a conditioned avoidance response (CAR) in mice trained in a CAR model of psychosis as compared to vehicle control (FIG. 8B).

Compound 12-132 (as identified in Table 1 of Example 12) was found to reduce PCP-induced hyperactivity, as shown in FIG. 8A. C57BL/6 male mice were co-injected with PCP (5 mg/kg) and either compound or vehicle via the i.p. route. Ten minutes later, the mice were placed in activity chambers and their locomotor activity in the horizontal dimension was monitored by infrared beam breaks for 20 min (5 consecutive 4-minute intervals (INT) as indicated). FIG. 8A shows that Compound 12-132 (10 mg/kg) substantially reduces the hyperactivity induced by PCP as seen by comparison to the vehicle+PCP control (p<0.0000001, n=8 per group, paired t-test).

Example 23

Reduction of Conditioned Avoidance Response by Compound 12-132

Figure 8B:
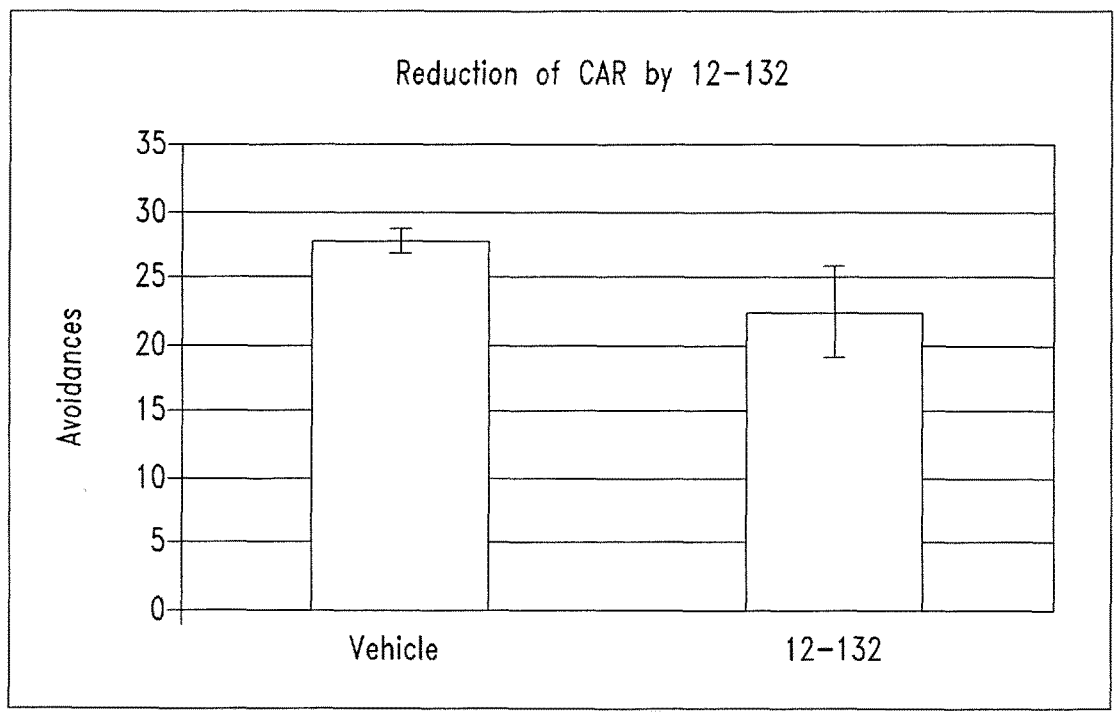

Compound 12-132 (as identified in Table 1 of Example 12) was found to reduce Conditioned Avoidance Responses (CAR), as shown in FIG. 8B. C57BL/6 male mice were trained in the CAR paradigm to predict and avoid the noxious stimulus (foot shock), reaching a plateau of approximately 25 avoidance responses per 30 trials ("training plateau"). The mice were then given either vehicle (15 minutes prior to testing) or compound (25 minutes prior to testing) via oral gavage, and were then tested for 30 trials in the CAR paradigm. Vehicle treatment and compound treatment were given to the same animals on alternating days, and the effect of compound in reducing avoidance response was analyzed through within-subject comparison (paired t-test). Vehicle exposure ("vehicle") does not alter the avoidance response of these trained animals. FIG. 8B shows that Compound 12-132 (10 mg/kg) significantly reduces the number of avoidance response (p=0.044, n=7 per group). In all these cases, the number of escape responses increased correspondingly and the total numbers of transitions between the two chambers did not change (data not shown), indicating a specific reduction of CAR that is not due to compromised motor function.

Example 24

Reduction of PCP-Induced Hyperactivity by Compound 12-134

Figure 9A:
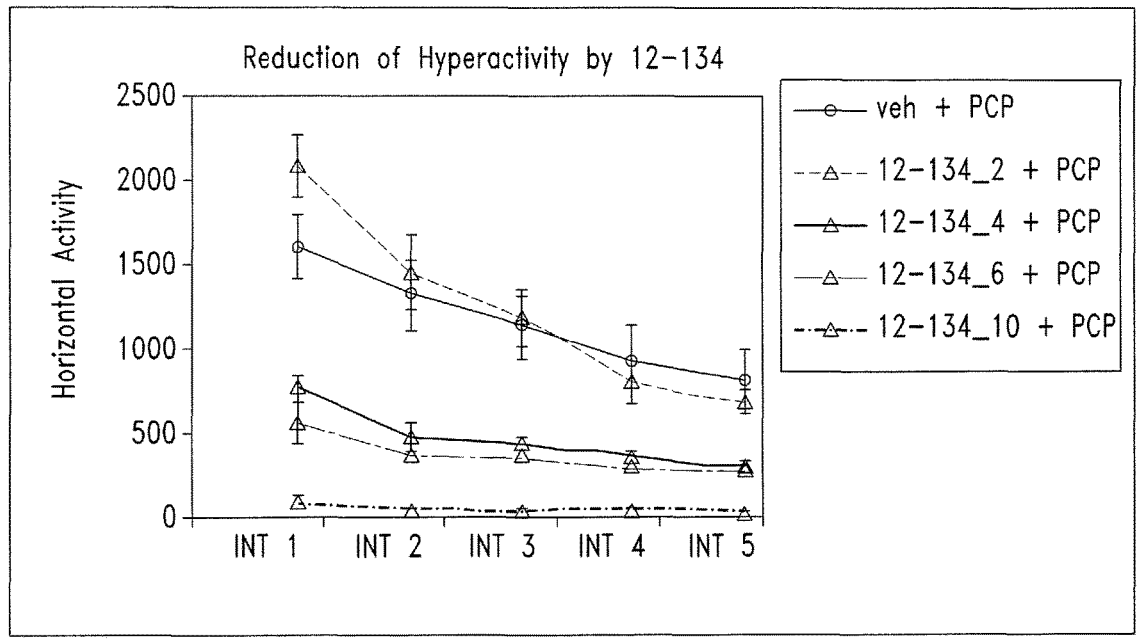
FIGS. 9A and 9B illustrate that Compound 12-134 of the present invention (as identified in Table 1 of Example 12) significantly reduces hyperactivity of mice in the PCP-induced model of psychosis, in dose-dependent fashion, as compared to vehicle control (FIG. 9A) and significantly reduces a conditioned avoidance response (CAR) in mice trained in a CAR model of psychosis, in dose-dependent fashion, as compared to vehicle control (FIG. 9B).

Compound 12-134 (as identified in Table 1 of Example 12) was found to reduce PCP-induced hyperactivity, as shown in FIG. 9A. C57BL/6 male mice were administered either compound or vehicle via oral gavage. Twenty-five minutes later, the mice were injected with PCP (5 mg/kg) via the i.p. route. The mice were placed in the activity chambers 10 minutes after PCP injection and their locomotor activity in the horizontal dimension was monitored by infrared beam breaks for 20 min (5 consecutive 4-minute intervals (INT) as indicated). FIG. 9A shows that Compound 12-134 (4, 6 and 10 mg/kg) reduces or abolishes the hyperactivity induced by PCP, as seen by comparison with the vehicle+PCP control (p=0.0033, 0.0012, and 0.00001, respectively, n=8 per group, independent sample t-test).

Example 25

Reduction of Conditioned Avoidance Response by Compound 12-134

Figure 9B:
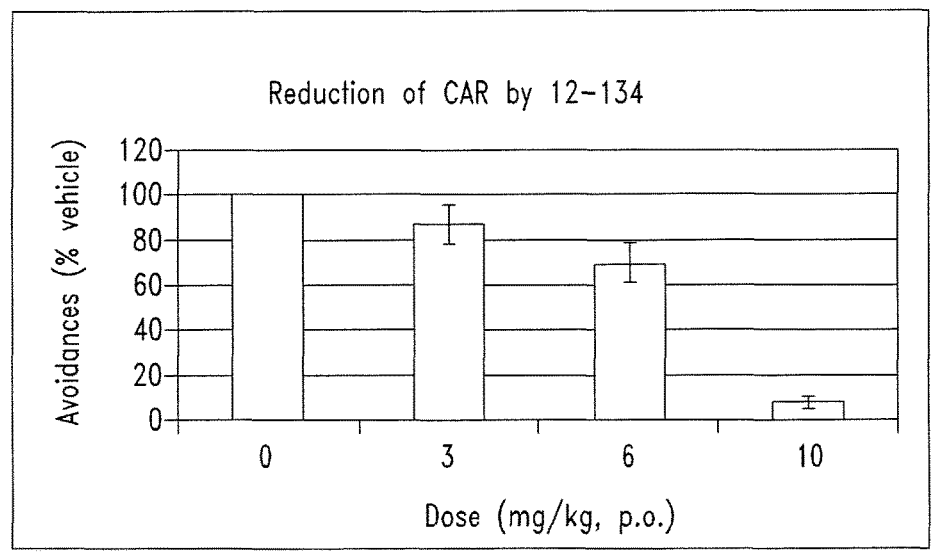

Compound 12-134 (as identified in Table 1 of Example 12) was found to reduce Conditioned Avoidance Responses (CAR), as shown in FIG. 9B. C57BL/6 male mice were trained in the CAR paradigm to predict and avoid the noxious stimulus (foot shock), reaching a plateau of approximately 25 avoidance responses per 30 trials each day. The mice were then given either vehicle (15 minutes prior to testing) or compound (25 minutes prior to testing) via oral gavage, and then were tested for 30 trials in the CAR paradigm. Vehicle treatment and compound treatment were given to the same animals on alternating days, and the effect of compound in reducing avoidance response was analyzed through within-subject comparison (paired t-test). Vehicle exposure ("vehicle") does not alter the avoidance response of these trained animals. FIG. 9B shows that Compound 12-134 (3, 6, and 10 mg/kg) significantly reduces the number of avoidance response (p=0.0117, 0.0043, and 8E-9, respectively, n=7 per group).

Example 26

Reduction of PCP-Induced Hyperactivity by Compound 12-115

Figure 10A:
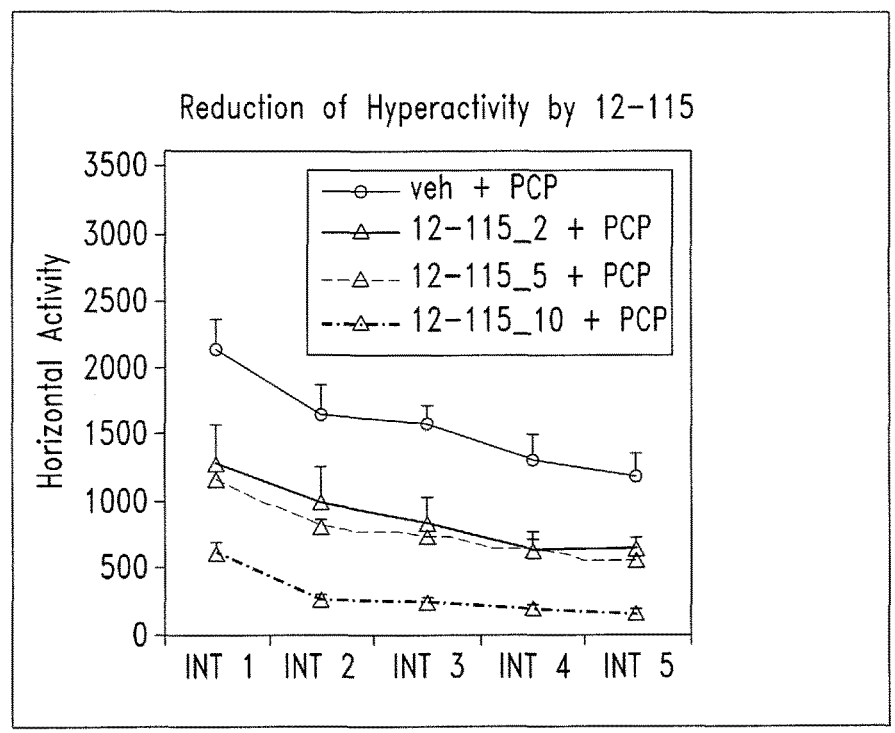
FIGS. 10A and 10B illustrate that Compound 12-115 of the present invention (as identified in Table 1 of Example 12) significantly reduces hyperactivity of mice in the PCP-induced model of psychosis, in a dose-dependent fashion, as compared to vehicle control (FIG. 10A) and significantly reduces a conditioned avoidance response (CAR) in mice trained in a CAR model of psychosis as compared to vehicle control (FIG. 10B).

Compound 12-115 (as identified in Table 1 of Example 12) was found to reduce PCP-induced hyperactivity, as shown in FIG. 10A. C57BL/6 male mice were administered either compound or vehicle via oral gavage. Twenty-five minutes later, the mice were injected with PCP (5 mg/kg) via the i.p. route. The mice were placed in the activity chambers 10 minutes after injection and their locomotor activity in the horizontal dimension was monitored by infrared beam breaks for 20 min (5 consecutive 4-minute intervals as indicated). FIG. 10A shows that Compound 12-115 significantly reduces hyperactivity at doses of 2 and 5 mg/kg p.o. (p=0.02 and 0.001, respectively), and abolishes hyperactivity at a p.o. dose of 10 mg/kg (p=1.5 E-5, n=8 per group, independent sample t-test).

Example 27

Reduction of Conditioned Avoidance Response by Compound 12-115

Figure 10B:
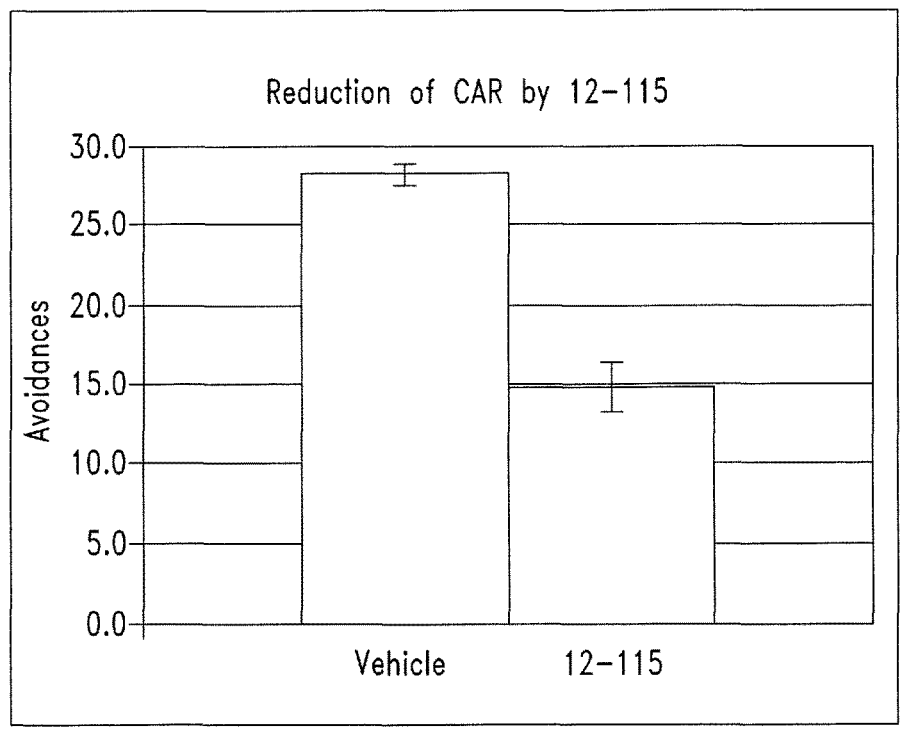

Compound 12-115 (as identified in Table 1 of Example 12) was found to reduce Conditioned Avoidance Responses (CAR), as shown in FIG. 10B. C57BL/6 male mice were trained in the CAR paradigm to predict and avoid the noxious stimulus (foot shock), reaching a plateau of approximately 25 avoidance responses per 30 trials each day. The mice were then given either vehicle (15 minutes prior to testing) or compound (25 minutes prior to testing) via oral gavage, and were tested for 30 trials in the CAR paradigm. Vehicle treatment and compound treatment were given to the same animals on alternating days, and the effect of compound in reducing avoidance response was analyzed through within-subject comparison (paired t-test). Vehicle exposure ("vehicle") does not alter the avoidance response of these trained animals. FIG. 10B shows that Compound 12-115 (10 mg/kg, p.o.) significantly reduces the number of avoidance response (p=1.2 E-5, n=7 per group, paired t-test).

Example 28

Reduction of PCP-Induced Hyperactivity by Compound 12-140

Figure 11A:
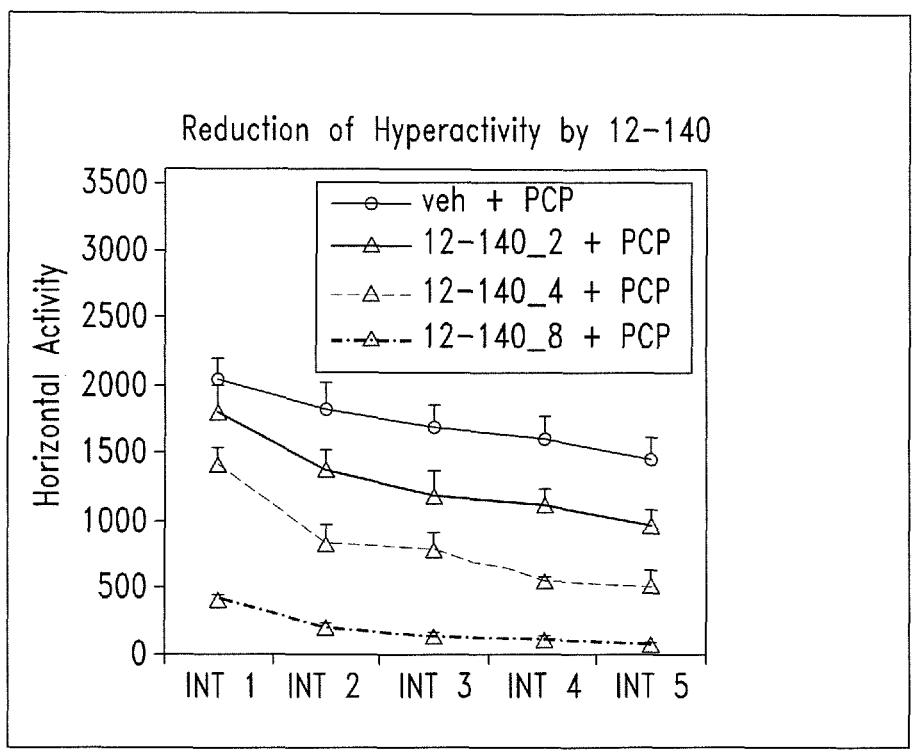
FIGS. 11A and 11B illustrate that Compound 12-140 of the present invention (as identified in Table 1 of Example 12) significantly reduces hyperactivity of mice in the PCP-induced model of psychosis, in a dose-dependent fashion, as compared to vehicle control (FIG. 11A) and significantly reduces a conditioned avoidance response (CAR) in mice trained in a CAR model of psychosis, in a dose-dependent fashion, as compared to vehicle control (FIG. 11B).

Compound 12-140 (as identified in Table 1 of Example 12) was found to reduce PCP-induced hyperactivity, as shown in FIG. 11A. C57BL/6 male mice were administered either compound or vehicle via oral gavage. Twenty-five minutes later, the mice were injected with PCP (5 mg/kg) via the i.p. route. The mice were placed in the activity chambers 10 minutes after PCP injection and their locomotor activity in the horizontal dimension was monitored by infrared beam breaks for 20 min (5 consecutive 4-minute intervals (INT) as indicated). FIG. 11A shows that Compound 12-140 significantly reduces or abolishes hyperactivity at doses of 4 and 8 mg/kg p.o. (p=0.004 and 5.9 E-8, respectively, n=8 per group, independent sample t-test).

Example 29

Reduction of Conditioned Avoidance Response by Compound 12-140

Figure 11B:
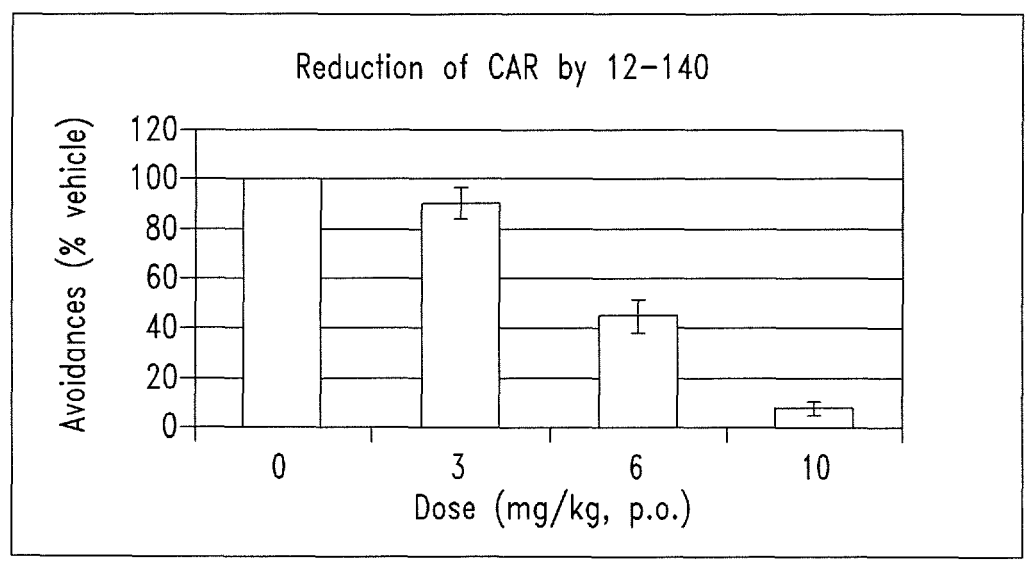

Compound 12-140 (as identified in Table 1 of Example 12) was found to reduce Conditioned Avoidance Responses (CAR), as shown in FIG. 11B. C57BL/6 male mice were trained in the CAR paradigm to predict and avoid the noxious stimulus (foot shock), reaching a plateau of approximately 25 avoidance responses per 30 trials each day. The mice were then given either vehicle (15 minutes prior to testing) or compound (25 minutes prior to testing) via oral gavage, and were tested for 30 trials in the CAR paradigm. Vehicle treatment and compound treatment were given to the same animals on alternating days, and the effect of compound in reducing avoidance response was analyzed through within-subject comparison (paired t-test). Vehicle exposure ("vehicle") does not alter the avoidance response of these trained animals. FIG. 11B shows that Compound 12-140 at doses of 6 and 10 mg/kg significantly reduces the number of avoidance response (p=0.00053 and 3.1 E-12, respectively, n=7 per group, paired t-test).

Example 30

Reduction of PCP-Induced Hyperactivity by Compound 12-142

Figure 12A:
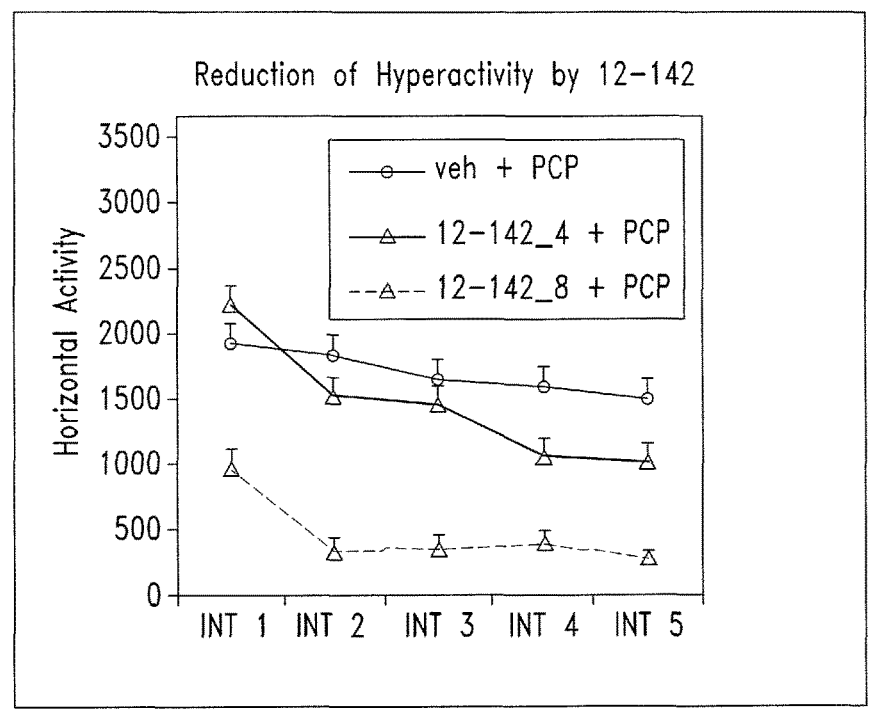
FIGS. 12A and 12B illustrate that Compound 12-142 of the present invention (as identified in Table 1 of Example 12) significantly reduces hyperactivity of mice in the PCP-induced model of psychosis as compared to vehicle control (FIG. 12A) and significantly reduces a conditioned avoidance response (CAR) in mice trained in a CAR model of psychosis as compared to vehicle control (FIG. 12B).
Figure 12B:
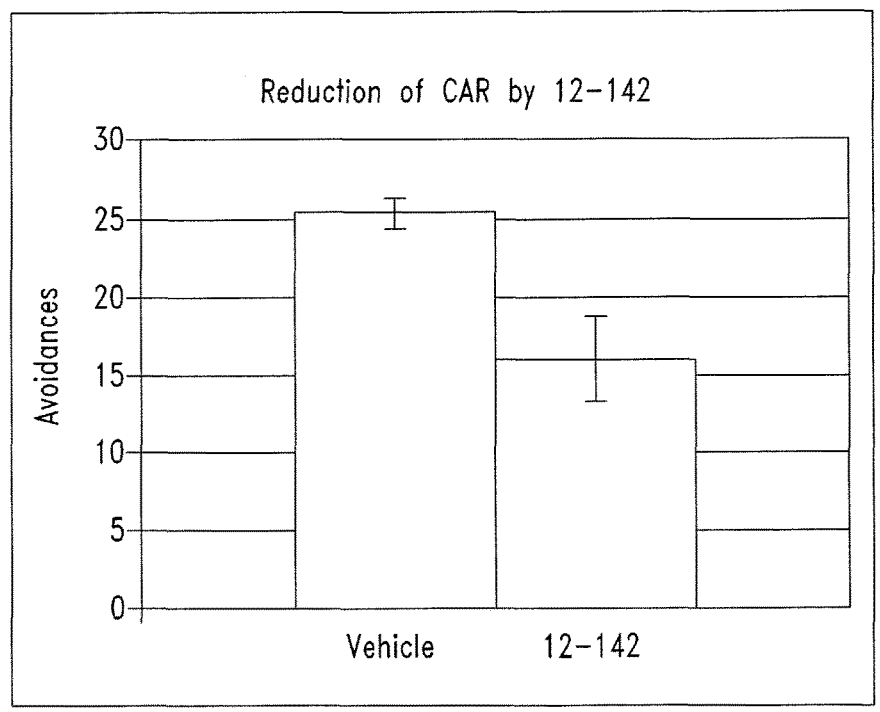

Compound 12-142 (as identified in Table 1 of Example 12) was found to reduce PCP-induced hyperactivity, as shown in FIG. 12A. C57BL/6 male mice were administered either compound or vehicle via oral gavage. Twenty-five minutes later, the mice were injected with PCP (5 mg/kg) via the i.p. route. The mice were placed in the activity chambers 10 minutes after PCP injection and their locomotor activity in the horizontal dimension was monitored by infrared beam breaks for 20 min (5 consecutive 4-minute intervals (INT) as indicated). FIG. 12A shows that Compound 12-142 essentially abolishes hyperactivity at a dose of 8 mg/kg p.o. (p=5.9 E-6, n=8 per group, independent sample t-test).

Example 31

Reduction of Conditioned Avoidance Response by Compound 12-142

Compound 12-142 (as identified in Table 1 of Example 12) was found to reduce Conditioned Avoidance Responses (CAR), as shown in FIG. 11B. C57BL/6 male mice were trained in the CAR paradigm to predict and avoid the noxious stimulus (foot shock), reaching a plateau of approximately 25 avoidance responses per 30 trials each day. The mice were then given either vehicle (15 minutes prior to testing) or compound (25 minutes prior to testing) via oral gavage, and were tested for 30 trials in the CAR paradigm. Vehicle treatment and compound treatment were given to the same animals on alternating days, and the effect of compound in reducing avoidance response was analyzed through within-subject comparison (paired t-test). Vehicle exposure ("vehicle") does not alter the avoidance response of these trained animals. FIG. 11B shows that Compound 12-142 at a dose of 5 mg/kg significantly reduces the number of avoidance response (p=0.033, n=7 per group, paired t-test).

It will be appreciated that, although specific embodiments of the invention have been described herein for purposes of illustration, various modifications may be made without departing from the spirit and scope of the invention. Accordingly, the invention is not limited except as by the appended claims.

What is claimed is:

1. A method for treating neurological disorders in a warm-blooded animal in need thereof, comprising administering to the animal an effective amount of a compound having the following structure (I):

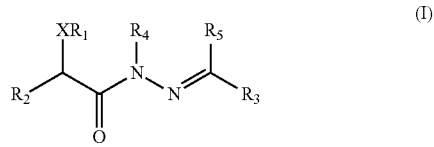

or a pharmaceutically acceptable salt, stereoisomer, solvate or prodrug thereof,
wherein:
X is —O— or —S—;
$R_1$ is $C_{1-6}$alkyl, $C_{1-6}$haloalkyl, $C_{1-6}$aralkyl, aryl, —$(CH_2)_nO(CH_2)_mCH_3$ or —$(CH_2)_nN(CH_3)_2$;
$R_2$ and $R_3$ are the same or different and independently substituted or unsubstituted heterocyclyl, or substituted or unsubstituted aryl; and
$R_4$ and $R_5$ are the same or different and independently hydrogen, $C_{1-6}$alkyl or $C_{1-6}$haloalkyl;
n is 1, 2, 3, 4, 5 or 6; and
m is 0, 1, 2, 3, 4, 5 or 6,
wherein the neurological disorder is Parkinson's disease, Huntington's disease, schizophrenia, or obsessive-compulsive disorder.

2. The method of claim 1 wherein the neurological disorder is schizophrenia.

3. The method of claim 1 wherein the neurological disorder is Huntington's disease.

4. The method of claim 1 wherein the compound has the following structure (II):

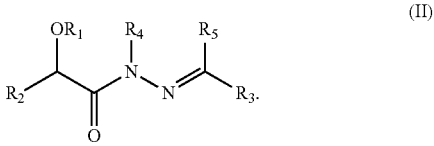

5. The method of claim 4 wherein $R_4$ and $R_5$ are the same or different and independently hydrogen or $C_{1-6}$alkyl.

6. The method of claim 4 wherein $R_4$ and $R_5$ are hydrogen.

7. The method of claim 4 wherein $R_1$ is $C_{1-6}$alkyl.

8. The method of claim 7 wherein $R_1$ is methyl.

9. The method of claim 7 wherein $R_1$ is ethyl.

10. The method of claim 7 wherein $R_1$ is isopropyl.

11. The method of claim 4 wherein $R_3$ is substituted phenyl.

12. The method of claim 11 wherein $R_3$ is 3,4,5-trimethoxyphenyl.

13. The method of claim 11 wherein $R_3$ is 4-bromo-3,5-dimethoxyphenyl.

14. The method of claim 4 wherein $R_2$ is substituted or unsubstituted phenyl.

15. The method of claim 14 wherein $R_2$ is 4-morpholinophenyl.

16. The method of claim 14 wherein $R_2$ is 4-(1H-pyrazol-1-yl)phenyl.

17. The method of claim 4 wherein $R_2$ is substituted or unsubstituted naphthyl.

18. The method of claim 4 wherein $R_2$ is substituted or unsubstituted heteroaryl.

19. The method of claim 1 wherein the compound has the following structure (III):

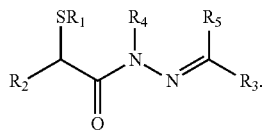

(III)

20. The method of claim 19 wherein $R_4$ and $R_5$ are the same or different and independently hydrogen or $C_{1-6}$alkyl.

21. The method of claim 19 wherein $R_4$ and $R_5$ are hydrogen.

22. The method of claim 19 wherein $R_1$ is $C_{1-6}$alkyl.

23. The method of claim 22 wherein $R_1$ is methyl.

24. The method of claim 22 wherein $R_1$ is ethyl.

25. The method of claim 22 wherein $R_1$ is isopropyl.

26. The method of claim 19 wherein $R_3$ is substituted phenyl.

27. The method of claim 26 wherein $R_3$ is 3,4,5-trimethoxyphenyl.

28. The method of claim 26 wherein $R_3$ is 4-bromo-3,5-dimethoxyphenyl.

29. The method of claim 19 wherein $R_2$ is substituted or unsubstituted phenyl.

30. The method of claim 29 wherein $R_2$ is 4-morpholinophenyl.

31. The method of claim 29 wherein $R_2$ is 4-(1H-pyrazol-1-yl)phenyl.

32. The method of claim 19 wherein $R_2$ is substituted or unsubstituted naphthyl.

33. The method of claim 19 wherein $R_2$ is substituted or unsubstituted heteroaryl.

* * * * *

UNITED STATES PATENT AND TRADEMARK OFFICE
CERTIFICATE OF CORRECTION

PATENT NO. : 9,783,521 B2
APPLICATION NO. : 13/742199
DATED : October 10, 2017
INVENTOR(S) : Neil S. Cutshall, Jennifer Lynn Gage and Thomas Neil Wheeler It is certified that error appears in the above-identified patent and that said Letters Patent is hereby corrected as shown below:

| Column | Line | Error |
| --- | --- | --- |
| 1 | 54 | "cGMIP" should read --cGMP-- |
| 13 | 36 | "PDE100" should read --PDE10-- |
| 16 | 3 | "(3-cyclodextrin" should read --β-cyclodextrin-- |
| 34 | 14 | "(E)-2-(4-(H-pyrazol-1-yl)phenyl)" should read --(E)-2-(4-(1$H$-pyrazol-1-yl)phenyl)-- |
| 89 | 50 | "assay volume was 1101" should read --assay volume was 110 μl-- |

Signed and Sealed this
Fourteenth Day of August, 2018

Andrei Iancu
*Director of the United States Patent and Trademark Office*